US005654170A

United States Patent [19]
Klinger et al.

[11] Patent Number: 5,654,170
[45] Date of Patent: Aug. 5, 1997

[54] POLYCYSTIC KIDNEY DISEASE GENE

[75] Inventors: Katherine W. Klinger, Sudbury; Gregory M. Landes; Timothy C. Burn, both of Northborough; Timothy D. Connors; William Dackowski, both of Hopkinton, all of Mass.; Gregory Germino; Feng Qian, both of Baltimore, Md.

[73] Assignees: Johns Hopkins University, Baltimore, Md.; Genzyme Corporation, Cambridge, Mass.

[21] Appl. No.: 323,443

[22] Filed: Oct. 12, 1994

[51] Int. Cl.$^6$ .......................... C12P 21/02; C12N 15/63; C07H 21/04
[52] U.S. Cl. ...................... 435/69.1; 435/320.1; 536/23.5
[58] Field of Search ........................... 435/69.1, 320.1; 536/23.5

[56] References Cited

PUBLICATIONS

Gabow, P.A., "Cystic Disease of the Kidney", In: Cecil Textbook of Medicine, Ed. J.B. Wyngaarden et al., Philadelphia: W.B. Saunders Company. 1988, pp. 644–647.
Wunderle et al. (1944) "Breakpoint break for consortium studying adult PKD" Cell 77: 785–786.
Gillespie et al. (1990) "Cosmid walking and chromosome jumping in the region of PKD1 . . . " Nucl. Acids Res. 18(23)7071–7075.
Harris, P.C. et al. (1995) "Polycystic kidney disease 1: Identification an analysis of the primary defect" J. Am. Soc. Nephr. 6(4):1125–1133 1995.
Peral, B. et al. (1996) "Screening of the 3' region of the polycystic kidney disease 1 (PKD 1) gene reveals six novel mutations" Am. J. Hum. Genet. 58(1):86–96 1996.
Peral, B. et al. (1995) "Splicing mutation of the polycystic kidney disease 1 (PKD 1) gene induced by intronic deletion" Hum. Molec. Genet. 4(4):569–574 1995.
Cotton, et al., (1988), Proc. Natl. Acad. Sci., USA., 85:4397.
European PKD Consortium, (1994), Cell, 77:881.
Gabow et al., (1989), Adv. Nephrol, 18:19–32.
Gabow, (1993), New Eng. J. Med., 329:332–342.
Guldberg et al., (1994), Nuc. Acids Res., 22:880.
Iglesias et al., (1983), Am. J. Kid. Dis., 2:630–639.
Nielsen et al., (1991), Science, 254:1497.
Parfrey et al., (1990), New Eng. J. Med., 323:1085–1090.
Peters et al., (1992). Contrib. Nephrol., 97:128–139.
Pierce et al., (1992), Proc. Natl. Acad. Sci., USA, 89:2056–2060.
Proc. European Dialysis and Transplant Assn., (1981), Robinson and Hawkins, eds., 17:20.
Ravnik–Glavac et al., (1994), Hum. Mol. Genet., 3:801.
Reeders et al., (1985), Nature, 317:542.
Saiki et al. (1988), Science, 239:487.
Striker et al., (1986), Am J. Nephrol., 6:161–164.
Tam, (1988), Proc. Natl. Acad. Sci., USA, 85:5409–5413.

Primary Examiner—Dian C. Jacobson
Assistant Examiner—Kawai Lau
Attorney, Agent, or Firm—Darby & Darby

[57] ABSTRACT

The present invention involves isolated nucleic acid encoding human PKD1, and sequences derived therefrom. The invention also encompasses vectors comprising these nucleic acids, host cells transformed with the vectors, and methods for producing PKD1 protein or fragments thereof. In another aspect, the invention involves isolated oligonucleotides that hybridize only to the authentic expressed PKD1 gene, and not to PKD1 homologues. In yet another aspect, the invention involves isolated mutant PKD1 genes, and their cDNA cognates. Further provided are isolated oligonucleotides that discriminate between normal and mutant versions of the PKD1 gene. Methods and compositions for treating APKD or disease conditions having the characteristics of APKD are also provided.

9 Claims, 31 Drawing Sheets

FIGURE 1

| FIGURE 1A |
| FIGURE 1B |
| FIGURE 1C |
| FIGURE 1D |
| FIGURE 1E |
| FIGURE 1F |
| FIGURE 1G |
| FIGURE 1H |
| FIGURE 1I |
| FIGURE 1J |
| FIGURE 1K |
| FIGURE 1L |
| FIGURE 1M |
| FIGURE 1N |
| FIGURE 1O |
| FIGURE 1P |
| FIGURE 1Q |
| FIGURE 1R |
| FIGURE 1S |
| FIGURE 1T |
| FIGURE 1U |
| FIGURE 1V |
| FIGURE 1W |
| FIGURE 1X |
| FIGURE 1Y |

FIGURE 1A

| | |
|---|---|
| CAGACTCTTTCCCATTAACACCTTTGCCTTAGGTTTATTTTCTGGTATCAATACTGGCACACTTACTTTGTTTGCA | 80 |
| GTTCCTGTCTTTTTTTTTTTTGAGACAGAGTCTCACTCTGTCACCCAGGCTGGAGTGAAGTGGCGGG | 160 |
| ATCTCGGCTCACTGCAACCTCTACCTCCTGGGTTCATGCGATTCTCCTGCCTCAGCTTCCCGAATAGCTGAGACCACAAC | 240 |
| TGTGTGCCACCATGCCCAGCCAATTTTGTATTTTTAGTAGACACGGGGTTTCACCATACTGGCCAGGATGGCTCAATCT | 320 |
| CTTGACCTCGTGATCCACCTGCCTCCGCCTCCCAAAGTGCTGGGATTACAGGCATGAGCCACTGTGCCTGGCCTTTTTT | 400 |
| TTCTTTTTGAGATGGAGTCTCACTCTGTCACCCAGGCTGGAGTGCAGTGGGTAACCTCAGGTCACTGCGACCTCCGCCT | 480 |
| CCCGGGTTCCAGTGATTCTCCTGCCTCAGCCTCCCGAGTAGCTGGGATTACAGGCACCACCACCATGCCTGGCTAATTT | 560 |
| TTGTATTTTTAGTAGAGACGGGGTTTGCCACGTTGGCCAGGTTGGTCTCGAACTCTTGGCCTCATGTGACCCGCCTGCC | 640 |
| TTGGCCTCCCAAAGTGCTGGGATTACAGGTGTGAGCCACTGTGCCTGGCCTGTTCTTGTTTCTTTCTCTCTCT | 720 |
| AGTTTCCCCCTTTAGGCTAACAATTATTCACTGTTAATAAAAACCCTCAGGTCTGTATTTTATCAAGAAACATTTCCT | 800 |
| CACGTCTCTTCCCTGAACCAAACAAGATCTCTGGCACATTTTATTTGCTCTGTCTCACCACATGGATTTGTTTTTTG | 880 |
| TTTCTTTGTTTTTGAGATGGAGTCTCACTCTGTTGCCCAGGCTGGAGTGCCATGGCACAATCTCAGCTCACTGCAACC | 960 |
| TCCACCTCCTGGGTTCAAGGCGATTCTCCTGTCTCAGCCTCCTGAGTAGCTGGGATTACAGGCGCGTGGCCACCACCCCAG | 1040 |
| CTAATTTTGTATTTTTAGTAGAGACGGGGTTTCACCATGTTGGTCAGGCTGGTCTCGAACTCCTGACCTTGTGATCTGC | 1120 |
| CCACCTTGGCCTCCCAAAGTGCTGGGATTACAGGCATGAGCCACCACGCCCGGCCCCCATGGTTTTTCAAATAGTTTAGA | 1200 |
| ATTTCATTTCCAGGTAACTAATTTGCTTCTTAAACATATGTCTTTCTATTTAAGAAATCCTTTCTAAACAATTGCATT | 1280 |

FIGURE 1B

```
TTATTCCACAACCGGCCTTCAAACAATCATTGAGACTTGGTTAATCTGTTTTGCTCATTTGGCAGCAGTTTCTTGTGGCTG     1360
TTTCTTCCCTCCACTGGAGTCCTTGAATCTTAAGTCTGTCATTTGACTGCAATTAAAAGCTGGGTTTGGAATACAATCGC     1440
AGCCTTACCACCATCCACCTGCTGTGTGACCTGGTAAATTTCTTTTTTTTGAGACGGAGTCTTGCTCTGTTGCCCAGG      1520
CTGGAGTGCAGTGGCACAACCTCTGCCTCCCAGGTTCAAGCGATTCTACTGCCTCAGGCTCCCTAGTAGCTGGGATTATA    1600
GGTGCCTGCCACCATGCCCAGCTGATTTTGTATTTTTAGTAGAGATGAGGTTTCACCATGTTGGCTAGGCTGGTCTGA      1680
ACTTCTGATCTTGTGATCTGCCCGCCTCGGCCTCCCAAAGTGCTGGGATTACAGGCATGAGCCACCACTCCCAGCCAGTT    1760
CTTTTTTCTTTTTTCCATTTTTTTTTCGAGACAGGATCTTACTCTTTGCCCAGGCGGAGTGCAGTGGCACAAT          1840
CACGGGCTCAGCGCAGCCACTGCCTACTGGGCTCTCACGCTCCTCCGGCCTCAGCCTCTCGAGTACCTGGGACTACAAGCG   1920
TGAGCCAGTTTGGCTAATTTTTGTAGAAACGGGGTCTCGCCATGTTGGCCAGGCTGGTCTCCAACTCCTG              2000
GACTCAAGGGATCCAGCACGCACCCAAGGAGACACTGTCCCGGCGAGGAGCCTGGAGCTGGGAAATACAAGGCATCAGA     2080
CTGGTCCCAAGACTCTCCCCAGCGGTGGGACAACTGTCTGCTTATCTAGTCCCCTCCGCCCTTTTCAATCCAACCCTG      2160
GGTCCTGGGCACCTCATAGTTCCAAACCCCTGTATGCACATCCCGGCTGTGATGCCTGGGACAGGTGTGTCACCTCTC      2240
CAAACCTGTTCCTCATCTGTGAATGCAAATCTCCACGGTCCCTATGCCTCGGATGGTCAGAGTCAGGATTCGGCATGA      2320
CGACCCCAACAGGAGCCTGGCACAGACCTGGCTCTGGGCAGCGTCCATAAAGGCCACCTGTTGTTTTATCTCCCGA        2400
AAGCGAACATGACAAGGCTTAACCCCCACGGCAATCCCCCCTCACCCCTGTTCTCAGGATAGCCTTGGAACCCAATAG      2480
CAGAGCGCCTGAGGCCCTTCATGACCCAGCCCCACCTCCCACCCGCGAGCCCACCCCCTGCCCTACCCCCTCACACCTCCCG  2560
```

FIGURE 1C

TGGCCAGCCTCCAGCTCACGGTCTTTGCTCACACCGTTCACCCCCTTCTTCTGGACCCACCTCATCGCCCCTTCCTAA 2640
GCATCAGCCCAATTCTTGCACATCCATCAAATCCTTTTCCAGACACCTCCTGGAACTCTTCCCTGCCGCCCCCTACAGCC 2720
ATCCCCACCTCTCCGGGTACCCCGCAGCCCCAGGCCGCATCCCAATTCCTCTCCAATTAGCGACTGTTTGTCCTCCCAGC 2800
TGAGCGCGGCCTCCGCGCCGCCCCCGCTGGCGTCTGAGAGCCCCCGGGTGGGACGTCTGTCTCCAGACCCGGGGTTTT 2880
TCGGCTCCCCGGGGCCGTGCCAACGCGGCTCCAGGCGTTCCTTATTTAGCAGGGCCGCGTGCCGCCGGAGCCTCGC 2960
CCTGGGAGCGTCTCTGGCCCCGCGTCCTGCTTCCCGTCCCAGGGAACCCGCCAGGGAACCCGCCCGTCCCGGCCTCT 3040
CCCGGGGTGCCGCTGGGCCCGCTACTCACAGGCGCTGTGCGTCCGCGGGATGCGCAGCGGGACCGAGCGTCCGCAGCC 3120
CGCGGGCCCGAGCAGTTGACGCGGCAGGCGGGAGCGCCGGGCGCTGGGCCGCAGCGGCCCAGCGCCCGGCCCGCAGC 3200
CGCGGCCCGGGGCCCCCGCCAGCCCGGCGGCGATGGCCCCGGCGGGCTGGATGGGCTGGGCCCGCGTGCCGAGGCCCAGCTCAGGCGGGGC 3280
GGCATCGTTAGGGCAGCGGCGCATGGCGGGCGGCCGGCCCGCTCGGACGCTGGCCGCTGCTGCTGCAGTGCGGCCCCGCCCGCCGGCGCTGGGGCCGAGCCCGCTCGGGGCTCGG 3360
CCGCGGACCGGCATGGCGGGCGGCCGGCCCGCTCGGACGCTGGCCGCTGCTGCTGCAGTGCGGCCCCGCCCGCCGGCGCTCCTCCTC 3440
GGCCAGGCCGCTCCGGAGCTCGGCCGCCCGCTCGGACGCTGGCCGCTGCTGCTGCAGTGCGGCCCCGCCCGCCGGCGCTCCTCCTC 3520
CTCCCCGCGCGGGGCGGCGCGGACGCGGGGTGCGAGGGGCGGGCGGGGGTGCAGGCTGCAGGCTCCGGCCCCCTTCGCCACAGGCGGACCG 3600
GGCCAGCAGCGATGAGGGACTGGCATCCGGAGGCTTCACCCTCCGCTCCGAGGCTTCACCCTCCGCTCCGGCAGCAGGTCGGCAGCAGGGCGGGGCCTCCGGAAGC 3680
TCCGCCCCACGCGTTCCCGGGGCGCATGCGACGTGGGGCGGGAGCGTCTGGAAGCACCGCGTCGCACTGCAGAGTCGGCC 3760
GAGGAGCACGAGCTATTTTTCACGCTCCGCCCCGCTGCAGGCTAAAGTGCGTGGGCGGGAAGCGGTGGGCAGGGTGCCAT 3840

FIGURE 1D

| | |
|---|---|
| CTGCTCCGCCCTTCTCCTGTGGTGGGCCAGGCGGCGGGGTTCCTCCTCCTGCAGCAGCCACAGGCTCCACCCTGATCCT | 3920 |
| TCTTCCGCGGTTGTGGATCCCTGGGGACGTGGCACATCCCCAGGCTTGCTAAACATTGGGTGGGTTCTGGCATTTGGTT | 4000 |
| TTGTAACGTTTCTGGGTCACTCCGCCTGTGGCCACCCTTCCTAGGGAGCCGTGTGTCCTTGGGCTTTGCTGGGTGG | 4080 |
| TCTCGAGGGTGGGAGAGAATGGGTTCTCCTGGACCAATGAGAGCCCGTGCCCCTCGGGGCCACATTGCTCCTCGCCTCCC | 4160 |
| TGACTGCGGACGCGTGTCTCGCGGCTGTCTCTCTGGAGATGGCCTCCTCCTGCCTGGCAACAGCACCCACAGAATTGC | 4240 |
| ATCAGACCTACCACCCGTTGTTTGTGATGCTGTAGCTGAGGGCTCTCTGTGCCAGGCCGGTCACTGGGGACTCTG | 4320 |
| TCCAGGGCCTGGTGGTTCCTGCTTCCCAGCACCTGATGGTGTCCATGAGAGCAGCCCCTCAGGAGCTGTCCGGGAGAA | 4400 |
| GGGCGCTGGTGGCTGCTGAGCGGAGAGCAAGGCCCGTGTTCTCCCAGGCCCTTGGCACAGCAGTGGAGCCCCGCCCCTGC | 4480 |
| CTTGTGTTGTCCTCTTAGGCTCTGTCCTGGGTTTGGAGGAGGGGACCCTGGGAGTTGGTGGCCTGTCCCAGCCTGAG | 4560 |
| CTGGCAAGATTCCGAATGCCAGGCCCGCGCTGGGCCCCAAGTGTGCAACAGGGCACAGGGTGACCTCATGTGGGCAGGTGGGTGCTGTT | 4640 |
| CTGTACACACCTGGGGCCTGGCTGGCCGCTGGAGAGTTCTGGAAGGTGGGTGAGGGGACCCATGGCAAACTAGGGCCTTAGGAA | 4720 |
| GGATGTGAAGGCCCCTGGGCTGGCCCAGGCCACCCTCTGTCTGTGGGAGAAGGGGTCAAGCTGGGAGAGGTGAAGGACACAGATCACAG | 4800 |
| AACTCCTCCTCGGGAGACGGCTGGGTTTCCCAGGAAGAGGGTCAAGCTGGGAGAGGTGAAGGACACAGATCACAG | 4880 |
| CTGCTGGCAGGTGTTCAAGGTCCAAGAGCGTTGCTGTCTGGGTGTCACCAGTAGCCTTCCTGGGGGCTCACGCAGGTG | 4960 |
| CCCTCTCCACTTGTGCTCCCTGCTCCCTGCTGAAGCTCAGCAGTGTCCAGTTCCAGGTGGAGGACAGCCGGGGC | 5040 |
| TTCTGAGGCCACAGCCTGCCTTGGGTTAATGATGCTGCCGAGAGGTGGTGGCTTTTGGAAAAGATGGGCTACTGCAAAAC | 5120 |

FIGURE 1E

| | |
|---|---|
| GTGCTGCTCTGCGTGGCTCGAAGCTTCGTGGGGAGAGCGTGGGCAGAGCCGTGGCTGACTCACAGACCCCCACCCAGAG | 5200 |
| CCTGCCCTGCCCTCCCTGCCCGACCCTTCTCCCTCCTGACCCATGTTTTTTTTTTTTTTTTTTGAGACAGA | 5280 |
| GTTCACTCTTGTTGCCAAGGCTGGAGTGCAATGGCACGATCTCGGCTCATGGCAACCTCCGCCTCCTGGGTTCAAGCGCT | 5360 |
| TTTCCTGCCTCAGCCTCCCGAGTAGCTGGGATTACAGGCGTGCACCACCACGCCTGGCTAATTTTGTATTTTTAGTAGA | 5440 |
| GACAGGGTTTCTCCATATGGTCAGGCTGGTCTTGAACTCCTGACCTCAGATGATCCGCCCGCCTCGGCCTCCCAAAGTG | 5520 |
| CTGGGATTACAGGCATGAGCCACCGCCCAGCCCTGACCCATGTTTTGAACCAAATTCCAGCCACCCTTTATCTGCAA | 5600 |
| GCATTTTGGAGGGCATCGCAATACTGCAGACCCACCTAACACAACAGACAGTTCCTTCATGCCACCGAAGGCCTGGTGTG | 5680 |
| TTCACATTTTGGTTTAATAGTTTGAATTAAGAGCCAAATAAGGTCCACACTGCAATAGTTGATGTCTTTTTTTTT | 5760 |
| TCTTTTTTTTTTTTTGAGACGGAGTCTTGCTCTTGTCTCCCAGGCCGCAGTGCAGTGGCATGATCTCAGCTCACCGC | 5840 |
| AACCTCCGACTCCCTGGTTCAAGCGATTCCTGCCTCAGCCTCCCGAGTACCTGGGTTACAGGCATGCACC | 5920 |
| ACCGTGCCCAGCTAATTTTTGTATTTTTAGTAGAGACGGGGTTTACTGTGTTGGCCAGGATGGTCTGATCTCCTGACC | 6000 |
| TCGTGATCTGCCCACCTCGGCCTCCCAAAGTGCTGGGATTACAGGCGTGAGCCACCGCCCAATGTCTTTAAAA | 6080 |
| ATATATACTTTTTTTTTTTGAGACGGAGTTTCGCTCTTGTCAGTGATTCTCCTGCCTCAGCCTCCCAGTAGCTGGGATTACAGGCATGCCAC | 6160 |
| ACGGCAACCTCCGCCCTCCGGGTTCAAGTGATTCTCCTGCCTCAGCCTCCCAGTAGCTGGGATTACAGGCATGCCAC | 6240 |
| CATGCCTGGCTAATTTTGTATTTTAGGAGAGACGGGGTTTCTCCACGTTGGTCAGGCTGGTCTCAAACTCCTGACCTCA | 6320 |
| GGTGATCCGCCTGCCTTGGCCTCCCAAAGTGTTGGGATTACAGGTGTGAGCCAACGCGCCCAGACAAAATATGTGTG | 6400 |

FIGURE 1F

TCTTTAAGGCTGGTCAAGCAAAGCAGTAGGACTGGAGAAAGAATGAAGAATTCTACCTGGCTGTGATCAATTCGTTGTGA 6480
ACACCACTGTGCTTGGACCAGTAGCTGATGTCTTTTGTTTTGTTTGTTTGAGACGGAGTCTGGCTCTGTCACCCAGGC 6560
TGGAGGACAAATGGTGTGATCTCGGCTCACTGCAGCCTCCATCTCCCGGGTTCAAGCGATTCTCCTGCCTCAGCCTCCTGA 6640
GTAGCTGGGATTAGAGGGCGGCGGCCACCACGCCCGGCTAATTTTTAAAAATATTTTAGTAGAGATGGGGTTTCACCATG 6720
TTGGTCAGGCTGGTCTTGAACTCTTGGCCTTAGGTGATCTGCTTGCCTCGGCCTCCCAAAGTGCTGGGATTACAGGTGTG 6800
AGTGATGTATTTATTTATTTATTTATTTATTTGAGATGGAGTCTCACTCTGTTGCCCAGGCTGGAG 6880
TGCAGCAGTGCCATCTCAGCTCACTGCAAGCTCCGCCTCCTGGGTTCACGCCATTCTCCTGCCTCAGCCTCCTGAGTAGC 6960
CTGGACTGGTGCCGCCACCATGCCCAGCTAATTTTTGTATTTTAGTAGAGACGGGGTTTCACCGTGTTAGCCAGGAT 7040
GGTCTGGATCTCCTGACCTCGTGATCCTCCCGCCTCAGCCTCCCAAAGTGCTGGGATTACAGGCTTGAGCCACCGCCTGT 7120
CTTTTAAATGTCCGATGATGTCTAGGAGCTTCCCTTCCCTCTCTTTTCCTTGTCAATTTGTTGAAGAAACTGGCTCCTG 7200
CAGCCTGGATTCTCGCTGTCTTGGGGGTGCCACCTCCATGGTGTCACCTCCGTGGTCCTGGTGAGTGTGTGCTTTGTG 7280
TTTCTTGTAAATTGGTCGTTGGAGCCGACATCCCATTGTCCCAGAGGTTGTCCTGGCTGGCACTGGCCTAGGTGTAGATG 7360
TCATCAGCTCAGGGCCCCCTGCTCTAAAGGCCACTTCTGGTGCTGGTTGCCACTCACCCTGGCTGGGGTCACCTGGGTC 7440
TGCTGCTGTCTCGCAAATGCTGGGGTCCAGGACTGGGCACATCGAGGGACTTGTAGGTGCTTGGTTCACTGATGTAAAA 7520
TATAGGAGCACCCGGGCCTTGCCCTTTCCCACCTGCATCCCTGAATGACACAGGAGAGTGTGGGAGAGTGTAGGGACAGCA 7600
GGCGCAGACCCGGGGCCCTGCCTGGGAATTGGCGTCGGGAAGACAGGCATTCTGGAGCGACCCCTAGGCCTGATGCCT 7680

FIGURE 1G

| | |
|---|---|
| TAGAGCGCAACTGCCAGAGAACACAGCTTCCTTGGGGGCTGGCCAGGCCACGGAGGGGCCCTGGCTGCTCCCATTTCTGGTCC | 7760 |
| CTGGATCCTGAGAGCGAGGACTAGGGATTGTCACCAAGGCCTCCATGAGCCCTCAGCAGAAGGAGGGCCACCCTCGAGGG | 7840 |
| CTCCGTTATCACTGGAGCCCGGCGTTCAACCAACACGCAGATGATTCTCCAAGGACAGAGATGGATGATGGGGAGGGGCT | 7920 |
| GGCCTGGAAGGACCCCAGTGCAGGTGACATTGAAGCCAGGTTTCAAAGCTCCCACGGGAGCTGCCCAGAGAGTCCC | 8000 |
| CAAGGGGCAAGGTGACTCGGGGGCAGGGGTAGGGCCCTGTCAGGAGAGCCTAGGAGAGGGCCTGTGTCTTCTAGGAAGAG | 8080 |
| CCCTGGCAGCCGAGCGGAGGCAGTGGTGAGGACCTGCATCCTGCAGCTGGCCTCACCCGGGTCCCTGAGCCGG | 8160 |
| GTCTTACGTGGCTCCCGCACTCGGGCGTTCAGAACGTGCCTGCGTGAGAAACGGTAGTTTCTTATTAGACGCGGATGCA | 8240 |
| AACTCGCCAAACTTGTGGACAAAAATGTGGACAAGAAGTCACACGCTCACTCCTGTACGCGATTGCCGGCCAGGGGTGGGG | 8320 |
| GAAGGGGATGGGGAGGCTTTGGTTGTGTCTCGCAGCAGTTGGGAATGTGGGGCACCCGAGCTCCCACTGCAGAGGCGACTGT | 8400 |
| GGAGACAGAGAGCACCTGCAGGTCATCCATGCAGTATCGGCTTGCATCCAGATCATACAGGGAACACTATGATTCAACAA | 8480 |
| CAGACAGGGACCCCGTTAAACATGGACACCAGCTGGCAACAGGGTGAGACCCCGGTCTCTAAAAAATAAAAGAACATTGG | 8560 |
| GATCGGCTTGAGCCCAGGAGTTTGACATCTGTGGTCCCAGCTATTCAGGAGACTGAGGTGGGACATCACTTGAGCCGAGGTCAAG | 8640 |
| CCGGGGTGGTGGTATGCATCTGTGATCACACCACTGCACTCCAGGCTGGGTCACAGAGCAAGACCCTGTCTCAAAAAAAAAAAAA | 8720 |
| GCTGCAGTGAGCTGTGATCACACCACTGCACTCCAGGCTGGGTCACAGAGCAAGACCCTGTCTCAAAAAAAAAAAAA | 8800 |
| AAAAAAAAAATCACAGGATCTGAACAGAGATTTCTCAAAGAAGACGCACAGTGGCCAACAGCGTGTGAGAAGATGGT | 8880 |
| CGGCCCTCATTAGTCATGAGGGAAACGTAAATCAAAACCACTGTCCAGCCTCAGCGGGCGCGGGTGCCTCACGCCTGTAATCCCAGC | 8960 |

FIGURE 1H

```
ACTTTAGGAGAGCAGATGGCTTGAGGCCAGGAGTTTGAGGCCAGCCTGGGCAACATAGCGAGACCAATAAATAGATATTA        9040
GTGGTGGCGCCTGTAGTCCCAGCTAGTTGGGAGGCTGAGGGGGAGGATTCCCTGAGTCTATGAGGTTGAGACTGCAGTT        9120
AGCTGTGATGGTGCCACTGCACTCCAGCCTGGGCGACTAGGAAACGGTCTTAAAAAAAAAAACAGGGTGGGC             9200
GCGGTGGTTCACGCCTGTAATCTCAGCACTTTGGGAGGCCAAGGTGGGGGATCACAAGGTCAGGAGTTTGTGACCAGCC        9280
TGACCAACATGGTGAAACCCCGTTCTACTAAAAATACAAAAATTAGCGAGGTGTGGTCGTGGGCGCCTGTAATCCCAGCT        9360
AATTAGGAGGCTGAGGCAGGAGAATCACTTGAACCCGGGAGGCGGAGGTTGCAGTGAGCCAATATCACACCACTGCACTC        9440
TAGCCTGGTCAACAGAGCGAGACTCTGTCTCAAAAAAAAAAATGCTGAGCGTGGTGGCGCATGCCTGTAGTCTCAGCTA        9520
CTTTGGGGGCTGAGGCAGGAGGAGAATCGCTTGAACCTGGGAGGCAGAGGTCGCAGTGAGCCAAGATTGCACCATTGCACTCC     9600
AGCCTGGGAGACAGAGTGAAACTCTGTCTCAAAAAGAAAAGGTCTAGGAAGAGTCCGCACCCTCCCCGCGGTGGCCAC         9680
GCCGGGCTCCGCTGAGCCCTCTGTCTTGTCTCTCCATACCTCATCACGGCACCCAGGGTTGCAGCCACTCCTGG            9760
TCTCATTTTACACACCAGGAAATTGAGGCTCTTTGAGAAGCCGTGGTGATGATTCATCAGCATGCTCTGGGGCAGACCC        9840
CTGCAGCCGCACAGGGTGCCTGGGGCCCACACTAGTGCCCTGGTTTATAGACAGACAGAGGTGGCAGTGGCGCTTCCGAG       9920
TCGGGCTGCGATGTGCTTGCACTCCCCGAGGGCTGAGGGCCCTGCGCCCTGAGGGCCCAGGTGCAGCTGCTTGGGTGCTGCCAGCCC  10000
CTCCCACCTCTCCCTGCCAGCCCTCCCACCTCTCCCTGCCAGCCCTCCCACCTCTCCCTGCCAGCC                   10080
CCTCCCACCTCTCCCTGCCAGCCCTCCCAGCCCTCCCACCTCTCCCTGCCAGCCCTCCCTGCCAGC                   10160
CCCTCCCACCTCTCCCTGCCAGCCCTCCCACCTCTCCCTGCCAGCCCTCCCACCTCTCCCTGCCAGC                  10240
```

FIGURE 1I

```
CCCTCCCCACCTCTCCCTCCCTGCCAGCCCCTCCCAGCCCCTCCCTGCCAGCCCCTCCCACCTCTCCCTCCCTGCCAG         10320
CCCTCCCACCTCTCCCTCCCTGCCAGCCCCTCCCAGCCCCTCCCTGCCAGCCCCTCCCACCTCTCCCTCCCTGGCT          10400
CATCCCTGCTGTCCCTTCTCTCTAGTTTCCTGTTCAGTTTCAGGAAGGAGGCTGGGAACCAGATGTAGGGAATTTGC          10480
GCCCTGGGAGTCAGACCTGGGTTCACGTCCCAGGCCTCCACCTCTGGTGTGACCTTGGTCCAGTCTCTCAGCCTCAGTTT       10560
CCTCACCTGTAAAGTGGGCTCCATGATTAGATGCACCCTGCAGGGCAGTGTAGCAGTGACCTGGCTCAGCCACTGGCAGC       10640
CCCAACAATCATACCTTGTTAAAGTAGCTCTGTGCGGTTCCCTCAGGGGTTCCGGGGCCCATTCCCCTGTCCTCCATGCA       10720
CTGTGAGACCTGCCCTGCCACAGAGCAGAGTGTAACAGCCTGAGGGTGAGACTCCTATGGAGCCAGACACTGTGCCTGTGCTTAGACCAG  10800
ACACTGGACGACGGGAGCCAGTGCAGCCTGGGCGGTGCAGGGCTCACAAGACCCGGCCCACTCCTGCTTGTGCCTACATCTGGGTGTTTGCCCTTCAG  10880
CGCAGGGCCGCGTGGCTTCTGGTGTGTGAGACGTGCGGGGCTGGGAAGTGTTGGCAGAGCCGCGAGTACCGTCCTCACTC        10960
TGCCTTTTGACGCGTTCTGGTAAGCTGGGCGAGTGGCCACTGCCTGAGTTCCGCTCAGTGCCGCCCTGATGTGCGGACCCCGCT   11040
CTTTGTTCTTTTGACGCGTTAGGTGGTGGCGGTGTGCGCTGTGCGCTGGGCACCGAGAGTCTTTGGGGAGGTTGT            11120
GCATTCTTGCTGTTAGGTGGTGGCGGTGTGCGCTGTGCGCTGGGCACCGAGAGTCTTTGGGGAGGTTGT                  11200
GCCAAGCCTGAGCCTGACGTCCCCCTTCCCGGCTTTCTGTTGCCTCTTCTGAGGCCAGGGCATCTCTATGAGGGCCTCC        11280
TGCTGGAGCCGTCTCTGTGATCTCCTCTGCCATCCTGCCCATGAGTGGGTGATGCGCTGGCCACCATCTGGTGACAGT         11360
GGCCGGGACCGCTGCCAAATGTGGGTCCCGCATCTGCAAGCCCCTCCCTGGGTCCCCTAGGGTATGGGGTGGTTCTGCC        11440
ACTGCCCTCGCTCCCCCACCTTGGGGTGCCTCTCCCCCCCTGCTCGTGGGGGAGACCCTGCCTGGGGATCTGCTTTCCAGCAA    11520
```

FIGURE 1J

| | |
|---|---|
| GGAATATACTTTGGAGGGAGACACACATGTTCTTTTCTGGAGCTCTGCAGTGGCCACGGCAGCCCAGCCCGCCAAGCACC | 11600 |
| CTGGAATGAAAACATCCCGCTGTCGTCTGGGCCTGGCCTGACACTCTGCTGCTGCCTCCAGTGGCTGCTGAGGCCGGGCAC | 11680 |
| GTCTGCGGGCACAGCAGCGGGGCGCCACAGTCTCCCTGCAGAGTGAGCGCAGCTGGAAAATGCAGCTCACGCCCTTTCC | 11760 |
| CAGAACACCTCGCTCTTCATGGCTTGGCAGCTGTCCTTGCCTAGGGGCCAGGGTGCCCAGGGCACTGGTGGCAGGAGAAGG | 11840 |
| GCTACATCTGGGGCTGAGGCGGGCTGGGTCCCTTTCTCCCTGCAGCTCCCGAGCTCCGAGGCCCAGCCCTGGCCCAGCCCTGGCATTC | 11920 |
| CTGACCTTAGCAGCGCCATGATCTGAAGACAGGCTGGCTTCTGTGAGGCCACCTCAGAAAGGGCTTGTGCCCAGGCAGA | 12000 |
| GGCGGAAGCCAGCTCTTCCTTCTGGTTGAGGCAGGAATGAGGCCAGCTGGGCAAGCCCATGCCCAGGGAACGTCACAG | 12080 |
| CTGTGGGAGTACAGGGGCTCCGGGTTCTGAGCCCGTCCACTGTGCATCGTGCCCTGGCCTCAGGATGGCTCGTACCATC | 12160 |
| ATTGGCTGTGCCCACAGCCGAGTGGGTGATGGAGCCCAGATGGCCCAGTTTGCTTGCCCCGCTGGATCTGTGCTGCCCTCTCCAGGGCAC | 12240 |
| TGCTGTGCCCGCACAGCGGGGCACAGCGGGGCCCAGATGGCCCAGTTTGCTTGCCCCGCTGGATCTGTGCTGCCCTCTCCAGGGCAC | 12320 |
| CCATTGACACACTGGACCCTGCTGGCTGCCCGGGGAGGTGTTGGGGGATGGTGTTGGGGGAGGAGGAGGCCCCTGAG | 12400 |
| CCTCAGTGTGCCCATCAGGAGCGTAAGGTCAGTGCAGCACCTGCCAGCACCAGGCTGTGAAGGGTGGAGTGGAGAGGGAT | 12480 |
| GCAAGGGGTCACAACGCCTGGCTCACGTCAGCTGCGTGCAGGAGCCGGCCCTCATTCTCCCCTTGAACT | 12560 |
| GGAAGGGTGGCCCGACCCCAGCGGGCAGGTAGCATACGTATGAAGCGCTCCTTCCTACACCCCACAGGTGGGCTCGTC | 12640 |
| TCCAGACGGCCCTTTTGAGCTGGCTGCTGTGTTTTTCCATCTGTGTAGGCAAGGACATCGCAGACTCCCTTTCTCATCTCC | 12720 |
| CTCGTTCAGCCTCCGAGGCCGGAGTCTCCATCCCTGTCCTGCCTGTGGGTCCCGGGAGGACCTGAGGCTGCCCATGTCA | 12800 |

FIGURE 1K

| | |
|---|---|
| CCCCCGGCATCTCATCCTGGGACAGTTCAGCCTGTGGGAGGATCTGTAAGGACAGAATGCGCTGAGCCTGGGGCTCCC | 12880 |
| CAGCTAGTCTCACACCCGTGTCTGGGACCCAGAGACCCTCGTGCAGGCTCTGTTGCTTGGGGCCTGGCAGCCTCGTCC | 12960 |
| TGTATCAGAGAGGCTGCCACCCCCACCCCTCGTGGGCCAGGTTGTGGCCGGCCTCCCTGGCCCTCCCATGAAGTGGTA | 13040 |
| GGCGGAGCCAGCAGCCATCTGCCCAGCCCCGGGGCTGCACTGTTTTTTTCAAATGAGCACCGTCCAAACTGCAGCCCGT | 13120 |
| TAATTTAAACAGGATCATTTCCGGCCCTGGAAGCCGCCTCACTCTCCTTAAATAGAAAGGAGCACAGCGCAGAGGGAAAC | 13200 |
| AGATGAGGTCATGGCTGGCTGGCCCAGCGAGGAAGGGCCGCAGTGGGGTGGCACTGCGCCTGTCCCCTGTCCTCTC | 13280 |
| CAGCGCGCCACACTGCAGCCCATTTCCTCACCCTGGGCCTGCTCTCGGGAGGACGGGCCTGGGGTCCTCTTGCTGGGCG | 13360 |
| GAGGGGAACCAGCTCCTCCAGGAGAGGACGGGCATGGGCCTCCCTGGGTCTCCTGGCGTCTCGTCCTGC | 13440 |
| CCCTGCCGAGGGAGGAGCCGGTTACATAAGCTCCGCCAGGGCCCCTCCGAGCCGGTCCCCCAGTTTCCAGTGAG | 13520 |
| GCGGCCAGCCGCGCGGGGTGCCGGGCCTGGCCGCCACACCCGCTGCTGACCACGTGTCTGGAATGTGCAGATGTTTCT | 13600 |
| TTGGGGGCTCCGTCCGGCCAGGTCTGGTTTGTCTGGGCCATTCCCTCTGTGGATTGGGAGGCCCCGGGAGCTGCCCACA | 13680 |
| TGAGACTCTGAGGCAGGTCTGGTTTGTCTGGGCCATTCCCTCTGTGGATTGGGAGGCCCCGGGAGCTGCCCACA | 13760 |
| CCCAGGAAGTTCTCCTCAGTCCCACTGTTGCATTCCCCGACCCGGCCTCAGGCTTCACCCACCCTCGGCGCAACTGTGGGGCAGAA | 13840 |
| GGCCCAGCCCAAGACTTCCCGGCCCTGCCAGCCTCAGGCTTCACCCACCCTCGGCGCAACTGTGGGCAGAGCCCAGGGG | 13920 |
| GAGGGCAGGAGAGCCCTGGCTGGGAACACCCTGAGGCTCCAGGGGCGAGGGCCCGACCTGGGGTTC | 14000 |
| ACACGCCCGGGTGGGGCAGACCGCTGCAGCCGTGCAGCATGAGACACGTGTCAGCTACCTCGGGCCCGGCCAGGCTGGCCCTGCTGC | 14080 |

FIGURE 1L

| | |
|---|---|
| CCACAGCCCTGGGACGTGGCCCCACCTGTGACGGGTGTGGAGGGCAGCCTCCAGGCCTGGCCACACCCTCTGCTGTTGC | 14160 |
| TGCTCCTGCTCCAGGATTGGCAAGGGTGCTGGGAAGGGTGAAGACCCGTACTGTGGCCACACACCTGGGACTTCCTTCT | 14240 |
| CCACCCAGTGGTGCCCCAGCAGCCGCTAAGGAGCCCGTGGTCCCACGCTAGGATGGTCCTAACTCCTCCCGCCTTCCA | 14320 |
| GATCGGGACGCTCGGCGCTGGGGACCCCTTGTGTCCCGGGCACCGTCCTGCCCCCATGGGGTGTACTCCTCCC | 14400 |
| GACAAGCTTGGCTTCAGCTTCCCTGGGAGCACATCCTGGCCCTCGGGCACCCATCAGGCTGTCCCTGTGCACCTGGCTCC | 14480 |
| CACCCTTCCAGCTCATAGCAGGAACTGGGGTGAGGAGTGCGTGGGGCAGCAAGGGCCTGGGACCCCAGAGGACCCTGCAC | 14560 |
| TCTGCTCTGTGCTCTTGCCTGGGCTTAGGGCCGCTCGGTGGTCCTGCTGCCAGATGCCTGGGCCCTGCTGTGTCCCCAT | 14640 |
| CTTGCAGGGAACCAGAACGTGGGGGCAGGGCATCAGACAGCGGCGATGATGTCACCTGGCGGGGTGCAGAGGAAGCCGAG | 14720 |
| GGGCGGGGTGGGGGCTGGCGGGCGGAGGCTGCCTGGCTAGGGACTCCACGGGGACCCCTGTGTTCCCTGAAGCCCACA | 14800 |
| AGACGTGAAAAAGTACGGAGCAAGCGAGGTGAGGACTCCACACCCAGGGGCACCTGAGTCCTACCCAGGGCAGAGCGCTTCCACACCCTG | 14880 |
| CCTGAGTCCTGCCCAGGGCAGATGCTTCCACACCAGGGGCACCTGAGTCCTACCCAGGGCAGAGCGCTTCCACACCCTG | 14960 |
| GGGGCTGGGGACTGCACCTGGCTCCTGTCTGGGCCCCAGCTTCATTCCACTGCCCTGGGCCCTGGGAGCTCGGCCGAGC | 15040 |
| GGGGGTCCCCAAGACCTTGCTGCATGGCCAGAACCGGTGACAGGCAGGGCTGCCTGGGGTGAGGCCGGGAGAAGGAGCCAGCCTGGAGCCTGG | 15120 |
| CACGCAGGAGTGCATGGCCAGAACCGGTGACAGGCAGGGCTGCCTGCGTGGAAGAAGTGTCCATGGCACCCCCAG | 15200 |
| GCCTGGTTCACAGTGGGATGGGCGGGGGAGCCGGGGGTCTGGGGGTCCTGGGCTGACCTGCCCCCACCCCTGCCCTGGC | 15280 |
| TTGTCAGCTCCCAGCAGCAGCCACTCTTGATGGATTTTCCAGAAAATGAGGTGTGGCCAAACATCTTCAGGCTTTTCCTT | 15360 |

FIGURE 1M

```
CTTTCCTTTCTCCCGTGGCCTGGGTGGGAGCTGCTCCCATGCCTGGGGCAGGTGCGAGAGCCTGTGCCCTCCCTGGG    15440
GCAGTTTCACAGCTGTGTCCCTTCCAGGGGCCTGCCTGTGTTCACCGTGGCCTCTGCAGCACCTCTCGGCCCTTAGGGC   15520
TCCTGCGCCTCGGGTCCCGGTGCCTCATTTCTCCCTAAAGCATTGGTTCTGCTGCCGCGCAGCCGCTGGAAAGTCCCTC   15600
CTCAGGTCTAACTGCAGTTCCTCACGGCACAGTGTTCCCCCTCGGGCATGGTGCTTGGGCAGTGGGTGTGAGTCCAGCTG  15680
CCTCACCCTGTCTCGAGAATGGCCTCTTGCTGGTCTCCCAGCACCACCCTGTCCCACCCACGGCGGGGATGGTGTGGA    15760
TGCCTAGCAGCGGGCTGTGGGCCCACCCATCCTTATGGGCAGTGGGGAGCACCTCAGCCCGTGTCCCTACCTTGGTGTA   15840
GAGGAGGGGACGGCAGAGAAGCAGGGTTCAGTTAGGGGAAGTGGTGGCCTGCCGGAGGGCGTTCCCTGTGTGCCT       15920
GGCCCCAGATCCTCTCCCCTCCCGGAGCCCAGGGCACAGGCATAGGCTCTCTGAGTGTCCCACAGCCCCTGGGGAAGG    16000
GAACTGCACCCCAACCGTGCCCTCCATCCGCAGATGGAAGGAGAAGCTCCGGGAGCCAGTGCCCAGCGTCTCATCTGTC   16080
TGGGCACCCAGCCCAGGTGAGGGCCTGGCTCCACCGTCCGTGGCTGCTTCCTGGCACGGAGAAGGCCTCGGCTG        16160
CTCTGTCCCCTCAGCTGGGGTGGCCTCTGGTCCCTCTGTGTTCCCTTCTCAAGCTCTTGCCCTGGCCCCGGGCC        16240
CCACCGGGCAGCCTGTGTGCGTCTCTCCTGCCCGGGTAGGCTCCTGTGGGAGCGGGAGCTCCGGTGGGAGGAGCAGGG    16320
CTGGAGGCTGGCAGGGCTGGGCGGGGTGTTCAGGGATGGAGGCCGCCCGGCGCTTGGGGCTGGCTGCCGGGTGGTCATTGC 16400
TGGGAAGAGCAAGTCTAGGCGGAGGCACCTGCTGGGTCACTCGTGGGGAGGGTGACACCTGGGAAGTAGAGGCCCGTGG   16480
CAGGAGGTGAGGCCTCGGGGTCCTGGGGAGCAGGGGTGTGTGCAGACCTGCCGGAGCCATAGTCCTGTGCCAGGAGCA    16560
CTACTGGGAGTGCGTGGGACCAGGGAGGGGTGCCCAGGGTGGGCGGCAGAGTGACCCCGAGGTGCTTGAGGCCGAGGGGA  16640
```

FIGURE 1N

| | |
|---|---|
| GGTGGAGTTCTCGGGTTTGCCCCAGCTCTCTGTCTACTCACCTCCGCATCACCAGCTCCAGGACCTGGTTTGTAACTCGGG | 16720 |
| CAGCTCTGAAAAGAGAGACATGCTGCCGGCCCTGTGGTTCTGTTGCTTTTCTTCACTGACTACTGACATGGGATGTTTT | 16800 |
| TCCTACGGCTGTGACCAATTGTGCTTCTTCTAATGCCTGGTTTTCTTTTTGTTTTGGAGTTTCTCTTTCTTCC | 16880 |
| TCCCTCCCTCTCACCCTCCACATCCTTTTTTTATTTTATTTTGAGATGGAGCTTCACTCTTGCAGGATGGGGTGC | 16960 |
| TGGAGTGCAGGGGTGCGATCTCAGCTCACTGCAACCTCTGCCTCCGGGGTTCAAGTGATTCTCCTGCCTAAGCCTCCTGA | 17040 |
| GTAGCTGGAATTACAGGTGCTTGCCACCACGCCCGACTAATTCTGTAGTTTTTAGTAGAGGAGGGTTTCACCCTGTTGGC | 17120 |
| CAGGATGGTCTCGATCTCTTGATCTCATGATCCACCCACCTTGGCCTCCCAAAGTTCTGGCATTACAGGAGTGAGCCACC | 17200 |
| GTGCCCGGCCATCTTTCTTGCTTCTCTTGTTTCTTGGAGACCGGGTCTTGCTCTGTCGCCCAGGCTGGACT | 17280 |
| GCAGTGGCACAATCATAGCTCACTGCAGCCTCGACTTCCCTGGCTCAAGGCGATCCTCCTCAGCCCCGAGTAGCT | 17360 |
| GGAACTACAGTTACACACTACCATGCCTGGCTGATTCTTTTTCCTTGTAGAGATGGGGTCTTGCTATGCTGTCCATCC | 17440 |
| TGGTCTCAAACTCCTGGCCTTCCCAAAGCACTGGGTTTACAGGCATAAGCCACCACACCCAGTTTCCTTTCTTCTTTTT | 17520 |
| AACTGGAATAGTTGACGTTTCTTATTAGCTGTGTGTCAGGAGGGTATTTTGGCCTTTAGTATGTCGTGTAAGTTGCT | 17600 |
| AGTGCTTTTCTGAGATTGTAGTTTGTTTTCTAATTTATTTATATTTGCGTAGAAGTTGTGTATTTAGATGGAGTTAG | 17680 |
| GTCGGCTGGTCTTTGATGTTTTATTTATTTAATTATGTATGTATTATTATTTTGAGGTAGAGTCTCGCCGTTTCACCC | 17760 |
| AGGCTGGAGTACAGTGATGCGATCTCAGCTCACCTTGACCTCTCGGGCTCAAGTGATTTTCTCTCCTCTACC | 17840 |
| TCCCGAGTACTTGGGACCCCAGGCGCCATGCCGCCATGCCTGGCTAATGTGTATTTTTTGTAGATACGGGGTCTCACTGTG | 17920 |

FIGURE 10

| | |
|---|---|
| TTGCCCAGGGTGGTTTCAAAATCCTGGGCCCAGGCGATCCTTCCGTCTCAGCTCCCACGGTGCTGTGTTACCGGCGTGTG | 18000 |
| CCCAGTGCCTGGCCGTCTTGGAGGTCTTGTTTCTCTGGGTTTATGCCTCGAGTCTGTGTGGGGCGGTGTGGACAGGGTTGG | 18080 |
| GAGACCTTGGCTCTGTGGGGACTGTGACAGGGGATGGGGCCTTGGCCCTGCGTGGACCTGGGTGGTTGGGGGTCCGTGCC | 18160 |
| CTTCCTGGCCCTGGGTGGACAGGTCCATGTGGCCATCGGCACTGGGCATAGGGCTGAGATGGGTGCAGAGGGCTGAGGCCCCCAGGC | 18240 |
| CTCTCCTGGCTTGGTTCCCCAGATGAGTGTTCATTTGGGTCTTCCATCAGAAAGTCCCCTCCTGACCTCTGGGAGTGGG | 18320 |
| GGGCTCAAGGGTGGGAGGCCATAGCTGGGGATGCTGGCAATGTGTGGGATGGGCCCAGGGAAGGCCTCTGGCCTACTAG | 18400 |
| GGGCTCTGGCCCTGACCCACGGCCACTCACTCCTCAGAGACGTCTCCCACAACCTGCTCCGGGCGCTGGACGTTGGGCTC | 18480 |
| CTGGGGAACCTCTCGGGCGCTGGCAGAGCTGTGAGTGTCCCCCAGTCGTGCCAGCATCGTGGGGCTCACTCCGGGTGGGCTG | 18560 |
| GCGGGCACCGCCCTCTTGCTGCTCAGCTGTGGGGGGCTTCCATCAGCTTTGCCGAATCCCCCGTCTCTTCCAGGGATATAAGC | 18640 |
| AACAACAAGATTTCTACGTTAGAAGAAGGAATATTTGCTAATTTATTTAATTTAAGTGAAATGTAAGTTGTGGTTCTTTG | 18720 |
| GGTGGGGTCCTGGCTGGACCCCAGGCCCCAGCCAGTTCACTGCCTGCTTGGAGCCCCCAGTGCCGGCTTGGTTGGGGCAGGGAGGGGTGCTGTC | 18800 |
| ACCAGATCCTGGGGCCAGTTCACTGCCTGCTTGGAGCCCCCAGTGCCGGCTTGGGTGGGGCAGGGAGGGGTGCTGTC | 18800 |
| ACCAGATCCTGGGGCCAGTTCACTGCCTGCTTGGAGCCCCCAGTGCCGGCTTGGTTGGGGCAGGGAGGGGTGCTGTC | 18880 |
| AGGGTGGCCAGGGCCTGGTTGCCAGTGGGGGCTGGCATAGACCCTTCCCACCAGACCTGGTCCCCAACACCTGCCCC | 18960 |
| TGCCCTGCAGAAACCTGAGTGGGAACCCGTTTGAGTGTGACTGTGCCTGGCGTGCCGCGATGGGCGGAGGAGCAG | 19040 |
| CAGGTGCGGGTGGTGCAGCCCGAGAGCAGCCACGTGTGCTGGGCTCCCCTGGCTCCCTGGCTCCCAGCCTCTGCTTGGCATCC | 19120 |
| CCTTGCTGCTGGACAGTGGCTGTGGTGAGTGCCTGTGGGTGAGCCAGCTCTGTCCTTCCCAGCCAGGTGGGACCTGGGCCCT | 19200 |

FIGURE 1P

| | |
|---|---|
| GCAGACACTGGGCAGGGCTCAGGAAGGCCTCTCTGGGGGGCCTCCGGGGGGCCTCCGGGGCCAAGGGAACAGCATGGGAGCCTGTGAGTG | 19280 |
| CGGCGGGGCGGGATGTGGGGCGTGGGGTGAGCCAGGAGGAGCAGAACCGGGTCCAGTGGCTGCCTCTTCTAGGTGAGG | 19360 |
| AGTTTGTGCCTGCCTCCCTGACAACAGCTCAGGCACCGTGGCAGCAGTGTCCTTTCAGCTGCCCACGAAGGCCTGCTT | 19440 |
| CAGCCAGAGGCCTGCAGCGCCTTCTGCTTCTCCACCGGCCCAGGCCCTCGGAGCAGGGCTGGTGCCTGTG | 19520 |
| TGGGGCGGGCCCAGCCCTCCAGTGCCTCTGTCCCTCTGCCTCCGGCCCCCGGCCCCCTCCTGCCCCCACCT | 19600 |
| GTAGGGGCCCCACCCTCCTCCAGTCACGTCTTCCCTGCCTCCCCAGGGCCACCCTGGTGGGCCCCACGGACCTTCTGC | 19680 |
| CTCTGGCCAGCTAGCAGCCTTCCACATGGTGCCCGCTCCCTGTCACTGCCACACGCTGGACTTCGGAAGTAGCTCCG | 19760 |
| CCGAGGTGGATGCCGGCTGGGCCGGCTGCCTCGCATCGGTATGTGCTGGGCGCTATCACGTGACGGCCGTGCTGCCC | 19840 |
| TGGGGGCCGGCTCAGCCCTGCGGGGGAAAAAATTTCAGGGGAAGGGCACCCGCGGTGGTTCAGGCTGGAGGCCGCCTACAGCATCGT | 19920 |
| TCGGTGCAGAGTGACGAGAGCCTCGACCTCAGCATCCAGAACCGGGTGGTTCAGGCTGGAGGCCGCCTACAGCATCGT | 20000 |
| GGCCCTGGGGCGGAGGAGCCGGCCGGGCCCGAGGTGAGTGTCTGCTGCCCACTCCCCCTTCCTCCCAGGGCCATCCAGATGGGGCAG | 20080 |
| AGCCTGGTACCCCGTCTTGGGCCACACTGACACCCTCGTTCCCACCGGTCTCCAGCGGTGCACCCGCTCTG | 20160 |
| CCCCTCGGACACGGAGATCTTCCCTGGCAACGGGCCACTGCTACCGGCCTGGTGGTGGAGAAGGGCCTGGTGCAGGCGC | 20240 |
| AGGAGCAGTGTCAGGCCTGGGCCGGGCCCCTGCCAATGGTGGAACAGTCCGCGTGCAGGCGCTTCCCTGGTCTCCC | 20320 |
| GGGTCACCAGGTGCCTGCCCCCACCCCCGAGGGGCCCATAGGTTGGGAGATCTCTGAAGCACTGGGGCACAGACTGCGGGC | 20400 |
| TGGGGAGTCTCAGGAGGAAGGAGGTGGGAGCTGGGCCCGGCCCGGTGGGCCGGTGGGCCGGTGGGGGCGTTCCTG | 20480 |

FIGURE 1Q

| | |
|---|---|
| TCAGCTCTGCAGATGCAGAGGTGGACATGAGCTGGGGGAGCCTCCGGACACTCCTGGCACGCCATACGGGAGGTGGCC | 20560 |
| TGCACGGGGATCCCTGCCGGTACCCACAGGCCCCGTGGGTGCTGCTGTGTGAGCCTGGGCTGTGGGCCCTGGTCTCC | 20640 |
| GGGCTCTGAGCCTCAGTTTCCCCATCTGGAAAGGGGGACAGTGATGGGCTCCCAGCGGGCTGCTGTGAGGGTGGGAGGA | 20720 |
| TGGAGGAGTGCCCTGAGCCCCTGCCATCCCACACCCCAGGAGCCTAGACGTGTGGATCGGCTTCTCGACTGTGC | 20800 |
| AGGGGGGTGGAGGTGGGCCCAGCGCCGCAGGGGCGAGGCCTTCAGCCTGGAGAGCTGCCAGAACTGGCTGCCCGGGGAGCCA | 20880 |
| CACCCAGCCACAGCCGAGCACTGCGTCCGGCTCGGGCCCACCGGGTGGTGTAACACCGACCTGTGCTCAGCGCCGCACAG | 20960 |
| CTACGTCTGCGAGCTGCAGCCCGGAGGTGTGCGGGGGCCAGGCAGGGCTGAGACGCTGGCTGTGTGGTTAGGGCCTGC | 21040 |
| CGAGCGCCCGCGGTGGAGCCTGGGCTGAGGAGGAGGGGCTGGTGGGGGGTTTCGGGCGCTCGGCTCCCCAGTCTGTT | 21120 |
| CGTCCTGGTGTCCTGGGCCCTGCCCGGCGCCTCACTGTGCACTGCGCCCAGCCCCAGTGCAGGATGCCGAGAACCT | 21200 |
| CCTCGTGGGAGCGCCAGTGGGGACTGCAGGGACCCTGACGCTCTCTGGCACAGCAGGACGGCCTCAGCCCGCAC | 21280 |
| GAGCCCGTGGAGGTAGTCGCGGCCCCCACGTTCTACAACCTGCCCTCCTGCCCCTGGAGGCCTTGCCTGCCCTGCCC | 21360 |
| ACTGTGGGTCTCGCCAAAAAACTTGGGGCCTTAATGTTGCTTGTGCCCAGTGAAGATGGTTGGGAAAATCCAGAGTGCA | 21440 |
| GAGAGGAAAGCGTTTACTCACATTACCTCCAGGCCTTTTCTCTGAGCGTGTGTGAGTTATTCCTGAAAGGCAGGTCAGGG | 21520 |
| GTCCTGCCCCCCATGGACAGTTTCCACCGGAGTCTTCCTCTCGAGGCACAGGAGCCAGGCCTGTGGGGTCTGATGGCTC | 21600 |
| GCTCTCCTTCCCTCCCCTCTTCCTGGAAGTTCGGGTAGGGGAGTCGGGCTTCAGGCTGGGATGGGGTCTGTGGAGCT | 21680 |
| GAGGCGGCCCCTGCCCACCAGGTCATGTATTCCCGGGCCTGCGTCTGAGCCGTGAAGCCTTCCTCACCACGGCCGAAT | 21760 |

FIGURE 1R

| | |
|---|---|
| TTGGGACCCAGGAGCTCCGGCGGCCGGCCCAGCTGCGGCTGCAGGTGTACCGGCTCCTCAGCACAGCAGGTGGGACTCTG | 21840 |
| GGTGGTGGGTGGTGGGGCGCCGGAGGACTCGGGGTGGCCTCTCTGAGCTTTCACGTCTGCTCGTGGTCCTGTGGCCA | 21920 |
| CCAGAGTGGTTCCCAGTCTTAGGTGGACAGAGCAGGGGTTCCAGAGACACCAGCTCATTCCAGGTGTCCTGGGGGTGGAT | 22000 |
| TGGGTGGGGGCCTGCCTGGGGTCAGTCGGCTGGGTCAGTCGGCTGGGGCCTGGGTCAGTCGGCTGGGGAGACGCAGCACTGGGCTGGGAGTGCTGCC | 22080 |
| CAGGTGGGGAGACCTGTCCTCACAGCAAGGCCAGGATTGCTGGTGCAGGCAGTTGGGCATCTCTGACGGTGCCTGTGGG | 22160 |
| CAAATCAGGGCCCAACACCCTCCCCTCCTCACAGGACCCCGGTGCAGGGGAGAAACGGAGCCTGAGAGCAGGTCCCGGACA | 22240 |
| ACAGGACCCAGCTGGCCCCCGCGTGCATGCAGGGGGACGCTGGTGCCCTGGAGCCAACATCTGCTTGCCGCTGGACGCC | 22320 |
| TCCTGCCACCCCAGGCCTGCGCCAATGGCTGCACGTCAGGGCCCAGGCTACCCGGGGCCCCTATGCGCTATGGAGAGA | 22400 |
| GTTCCTCTTCTCCGTTCCCGGGGCCCCCGGCGCAGTACTCGGTGTGTGGCCCTGACCTGGGTCTGTTCCCTGCATCTC | 22480 |
| CTCAGGCCACCTTCCTCTGTCTGCTCCAGGGTCTCTGGGTCTGTGTGCACCAGACACACCAGCCTGCAGGCCCCTCCACGTC | 22560 |
| CTTGCCACCTCTGACCTCGACCTCTGCCCTCTCCCAGTGGGAGAAGCTCTCGCCTGGCCCTTGGCAC | 22640 |
| GAGCTGTGCTCCTCTTCCTCTCTGCCTGTCCTGCCAGGTCTTGGCCTGTGTCCTCTCCCGTG | 22720 |
| TGTCCCCCGGTCTGCAACTGTCCTGCACCCTCATCCGTCGTGCGGGGTCCACGGGCCATGACCGTGAGGACGTGGCTGACGAAGC | 22800 |
| GGGGAGCCCTGCGTGCGTGTCCACCCTCATCCGTCGTGCGGGGTCCACGGGCCATGACCGTGAGGACGTGATGCAGCCCTGC | 22880 |
| CTCCCTCTCCACAGGTCACCCTCCACGGCCAGGATGTCCTCATGCTCCCTGGTGACCTCGTTGGCTTGCAGCACGACGCT | 22960 |
| GGCCNTGGCGCCCTCCTGCACTGNTCGCCGGNTCCCGGCCACCCTGGTCCCCGGCCCCGTACCTCTCCGCCAACGCCCTC | 23040 |

FIGURE 1S

| Sequence | Position |
|---|---|
| GTCATGGCTGCCCCACTTGCNAGCCCAGTGGAGGGCACTTGGGCCTGCCCTGCCTGTGCCCTGCGGCTGCTTGCAGCCA | 23120 |
| CGGAACAGCTCACCGTGCTGCTGGGCTTGAGGCCCAACCCTGGACTGCGGCTGCCTGGGGCGTATGAGGTCCGGGCAGAG | 23200 |
| GTGGGCAATGGCGTGTCCAGGCACAACCTCTCCTGCAGCTTGACGTGGTCTCCCCAGTGGCTGGGCTGCGGGTCATCTA | 23280 |
| CCCTGCCCCCCGGACGGGCCGCCTCTACGTGCCCACCAACGGCTCAGCCTTGGTGCTCCAGGTGGACTCTGGTGCCAACG | 23360 |
| CCACGGCCACGGCTGCGCTGGGCCTGGGGGCAGTGTCAGGCCCGCTTGAGAATGTCTGCCCTGCCCTGGTGGCCACCTTC | 23440 |
| GTGCCCGGCTGCCCCTGGGAGACCAACGATACCCTGTTCTCAGTGGTAGCACTGCCGTGGCTCAGTGAGGGGGAGCACGT | 23520 |
| GGTGGACGTGGTGGAAAACAGCGCCCAGCCCCGAGCCCGTGTACTGCAGGAGTCCTAGTGGTGAGTATGGCCGAGGCTCTA | 23600 |
| TCCGCGCCACGCCCAGCCCCGAGGGCCGTGTACTGCAGGGAGTCCTAGTGGTGAGTATGGCCGAGGCTCCACCACCAGCC | 23680 |
| CCCAGGCAGGTCGGCCCCGGGCAGGTCCTGCAGACAGGGTGCTGCAGGAGTCCTGCAGTGAGGGCAGCAGCCCAGTTACT | 23760 |
| GGGGACGTCGGCCCCGGGCAGGTCCTGCTGCTCCTCGGGCTACCTGTGTGGGCTTAAATTCCTGGAAAGTCACGG | 23840 |
| CTCTGACAGTGGCTCCGCTAACTCATTCCACTGTCTCATTTCACAAAATGAATTTAAAACTCTGCTCCCTGACCTCACAC | 23920 |
| GAGCCCCGTGAGTCTCTCACGCCCTCTGCTGTTCTCGCCTGGCTAAAGCGAGTGGCTTTGAGGTGGAGTCTGAACC | 24000 |
| CCTGATGGGAAACTGCGGGCTGCCCGGGTGCCACCATGCTGGGTGCCACCATGCTGGGTGTCTCCATCTTGCGGGTA | 24080 |
| CCTGCCTCTTCACCAGGGCCTTGGGAGGGGCCATCAGAAATGGCGTGACCTGTCCAGCCTGTCCTGGGTTCTGTAAGCC | 24160 |
| AGTGTAGGTGCCTCCCCTCACTGCTCCGAGCTCTCTGGGTGAGGAGCTGGGCAAGAGCGCGGAGGGTCTGAGAAGAC | 24240 |
| TCAGAGAGAGGTGGACTCTTTGTAGCTGGTACTAGGTTTGCTTTACAGATGGGAAACTGAGGCACAGAGAGGTTGAGGC | 24320 |

FIGURE 1T

```
ATTAGTAGTACTACATGGCTGGCTGGAGAGCGGACAGTGAGTGTCCAGCCCGGGCTTGGCTCCCATGGCATGCAGAGC         24400
CCCGGGCACCTCCTCCTCTGTGCCCCGGTGGGACTCTCCAGCCCGACGGGAGGTGTGTCCAGGAGGCGACAGGCTAA         24480
GGGCAGAGTCCTCCACAGAGCCCAGGCTGACACCATTCCCCCGCAGAGGTACAGCCCCGTGGTGGAGGCCGGCTCGGAC       24560
ATGGTCTTCCGGTGGACCATCAACGAGACAAGCAGTCCCTGACCTTCCAGAACGTGGTCTTCAATGTCATTTATCAGAGCGC    24640
GGCGGTCTTCAAGCTCTCAGTAGGTGGGCGGGGTGGGGAGGGGAGGGGATGGGGCAGGGGCGGGGGGCGGGGGCTCCA        24720
CCTTCACCTCTGCCTTCTGCTCTGCTTCATGCTGCCCGAGGACGCTGCCATGGCTGTGGGTGAGTGGAGGGAGGACGCC       24800
AATCAGGGCCAGGCCTCTCCACCTGGGCTCACTGACGCCTGTCCCTGCAGCTGACGGCCTCCAACCACGTGAGC            24880
AACGTCACCGTGAACTACAACGTAAACGTGGAGCGGATGAAACAGGATGCAGGGTCTGCAGTCTCCACAGTGCCGGCCGT      24960
GCTGTCCCCCAATGCCACGCTAGCACTGACGGGCGGGCGTGCTGGTGGACTCGGCCCGTGAGGTGGCCTTCCTGTGAGTGA    25040
CTCGGGGGCCGGTTTGGGGTGGGCACCAGGCTCTTGTCCCAGCCCCAGCCTCAGCCGAGGACCCCACATCACGGGGTT       25120
GCTTTTCTGAGCCTCGGGTTCCCTGTCTGTGTTGGGAGGTAACTGGGTGCACAGGAGCCCTGAGGCTGCACGGGAGCCGGGA   25200
GAGGCCTCAGCACAGCGGGGTGGGCCCTGAATGGAGGCCCGGGGCGTGACTGCAGAGTGGAGCCTCGGCTGGGTCCCAAG     25280
CACCCCCTGCCCCGGCACCGCCACCCCCACCCCTGTCCCGGTTCACTCACTGGTCTCCCACCGCCCGGGAGGTGGACCTTTGGGG 25360
ATGGGGAGCAGGCCCTCCACCAGTTCCAGCCTCCGTACAAGAGTCTTCCAGTTCAGACCCTCGTGCCAGGTGCTGGTGG       25440
AGCACATGTCACGGCACACCTACGCTGCCNNACTGGTNAGGNAGGCCNAGNNTNGGGGNGTGGACAGGAAGGTGGGC          25520
CCTGAACTGTGCTTTCCGCCCCTCCCCGGGCCTGGCTCTTGCTGCTCTGCCCGAGTGCAGCTGCACTTGGAGGCGGT         25600
```

FIGURE 1U

| | |
|---|---|
| GCCGTCCTCGCCAGGCAGCCCTCAGTGCTGCTACACCTGTGCTCCGTCCCGCACGTGGCTTGGGAGCCTGGGACCCTTAA | 25680 |
| GGCTGGGGCGCAGGTGCAGCCGTTCACCCCGGGGCTCCTCAGGCGGGGGCTTCTGCCGAGCGGGTGGGGAGCAGGTGGGG | 25760 |
| GTGCCGCGGCTGCCCCACTCGGGCCTGTCCCCACAGGTGAGTACCTCCTGACCGTGCTGGCATCTAATGCCTTCGAGAAC | 25840 |
| CTGACGCAGCAGGTGCCTGTGAGCGTGCGCGCCCTCCCTGCCCTCCGTGGCTGTGGGTGTGAGTGACGGCGTCCTGGTGGC | 25920 |
| CGGCCGGCCGTCACCTTCTACCCGCACCCGCTGCCCTCGCCTGGGGTGTTCTTTACACGTGGGACTTCGGGGACGGCT | 26000 |
| CCCCTGTCCTGACCCAGAGACCAGCCGGCTGCCAACCACACCTATGCCTCGAGGGGCACCTACCACGTGCGCCTGGAGGTC | 26080 |
| AACAACACGGTGAGGGTGCGGCGGCCCAGGCGGGATGTGCGCGTCTTGAGGAGCTCCGGGACTCAGCGTGGACATGAG | 26160 |
| CCTGGCCGTGGAGCAGGGCGCCCCGTGGTGTCAGCGCGGTGCAGACGGGCGACAACATCACGTGGACCTTCGACA | 26240 |
| TGGGGGACGGCACCGTGCTGTCGGGCCCCGGAGGCAACAGTGGAGCATGTGTACCTGCGGGGCACAGAACTGCACAGTGACC | 26320 |
| GTGGGTGCGGCCAGCCCCGGCCACCTGGCCCGGAGCCTGCCACGTGCTGGTCTTCGTCCTGGAGGTGCTGCGCGTTGA | 26400 |
| ACCCGCCGGCCTGCATCCCCACGAGCCTGCCAACACGAGCCTGACGGCGGGGGGGTGCCCGACGGTGACACAACTTCACGCGGAGCGGC | 26480 |
| ACTGGACCTTCGGGGATGGCTCCTCCAACACGAGCCTGACGGCGGGGGGTGCCCGACGGTGACACAACTTCACGCGGAGCGGC | 26560 |
| ACGTTCCCCCTGGCTGTCGTGTCCAGCCAGAGAGGCCATTACTTCACCAGCATCTGCGTGGAGCCAGAGGT | 26640 |
| GGGCAAGTCACCCTGCAGCCAGAGAGGCAGTTTGTGCAGCTCGGGGACGAGGCCTGGCTTGGCATGTGCCTGGCCCC | 26720 |
| CGTTCCCCTACCGGTCACCCTGGGACTTTGGCACCGAGGAAGCCGCCCCACCCGTGCCAGGGGCCCTGAGGTGACGTTC | 26800 |
| ATCTACGAGACCCAGGCTCCTATCTTGTGACAGTCACCGCGTCCAACAACATCTCTGCTGCCAATGACTCAGCCCTGGT | 26880 |

FIGURE 1V

```
GGAGGGTGCAGGAGCCCGTGCTGGTGCACCAGCATCAAGGTCAATGGCTCCCTTGGGCTGGAGCTGCAGCAGCCGTACCTGT      26960
TCTCTGCTGTGGGCCGTGGGGCGCCCCGCCCAGCTACCTGTGGGGACGGTGGGTGGCTCGAGGGTCCGAGGTC              27040
ACCCACGCTTACAACAGCACAGGTGACTTCACCGTTAGGTGGCCGGCTGGAATGAGGTGAGCCGCAGCGAGCCTGGCTC         27120
AATGTGACGGTGAAGCGGCGCCGTGCGGGGCTCGTCAATGCAAGCCCCACGGTGGTGCCCCTGAATGGGAGCGTGAG           27200
CTTCAGCACGTCGCTGGAGGCCGGCAGTGATGTGCGCTATTCCTGGTGCTCTGTGACCGCTGCACGCCCATCCCTGGGG         27280
GTCCTACCATCTCTTACACCTTCCGCTCCGTGGGCCACCTTCAATATCATCGTCACGGCTGAGAACGAGGTGGGTCCGCC        27360
CAGGACAGCATCTTCGTCTATGTCCTGCAGCTCATAGAGGGGCTGCAGGTGGTGGGCCGTGGCCGCTACTTCCCCACCAA        27440
CCACACGGTACAGCTGCAGGCCGTGGTTAGGGATGCACCAAACGTCTCCTACAGCTGGACTGCCTGGAGGACAGGGGCC         27520
CGGCCCCTGGCCGCAGGCGGGCAAAGGCTTCTCGCTCACCGTGCTCGAGGCCGGACCTCGTGGAGCCCTCGTGCGCGGCCACC     27600
AACATGCTGGGCAGCGCCTGGGCGACTGCCACCATGGACTTCGTGCCGAGCTGGTGCTGATGGTGCGCCTCCCC             27680
GAACCCAGCTGCCGTCAACACAAGCGTCACCCTCAGTGCCGAGCTGGCCATTTACCACCCATAGCTTCCCCACACCGGCTGCACTTGGTCCT 27760
TGGAGGAGGGCTGAGCTGGGAGCTCCGAACCCCGCTGGGAGACCTCCAGCAGTTCGTGGGCGGCCGGGTCCTCTGTGCCCTTTTGGGGCAGTGGCCTCACC 27840
ATGACGGCAGGAACCCGCTGGGCGAGCCCGGAGGCAGCTTCGTGGGCGGGCCAGGAGCAAGCGTGGCCCTCATGTCACCATGTCTTCCCGGATGCTGGGCTGTGAGTGGCCTCAGCAT 27920
CAGGGCCAGCGAGCCCGAGCCCGGAGGCAGCCCGGAGCAGCTTCGTGCCCTTTGGGGCAGCTGGCCACGGCACCA           28000
ATGTGAGCTGGTGCTGGGCTGTGCCGGCGGGGTGGCCCAGCAAGCGTGGCCCTCATGTCACCATGTCTTCCCGGATGCTGGCA    28080
CCTTCTCCATCGGCTCAATGCCTCCAACGCAGTCAGCTCGGGTCTCAGCCACGTACAACCTCACGGCGGAGGAGCCCATC       28160
```

FIGURE 1W

| | |
|---|---|
| GTGGGCCTGGTGCTGTGGGCCAGCAGCAAGGTGGTGGGCGCCCGGGCAGCTGGTCCATTTTCAGATCCTGCTGGCTGCCGG | 28240 |
| CTCAGCTGTCACCTTCCGCCTGCAGGTCGGCGGGGGCCAACCCGAGGTGCTCCCCCGGGCCCCGTTTCTCCCACAGCTTCC | 28320 |
| CCCGCGTCGGAGACCACGTGGTGAGCGTGCGGGGCAAAAACCACGTGAGCTGGGCCCAGGCGCAGGTGCGGCATCGTGGTG | 28400 |
| CTGGAGGCCGTGAGTGGGCTGCAGGTGCCCAACTGCTGCGAGCCTGGCATCGCCACGGGCACTGAGAGGAACTTCACAGC | 28480 |
| CCGCGTGCAGCGGNCTCTCGGGTCGCCTACGCCTGGTACTTCTCGCTGCAGAAGGTCCAGGGCGACTGCTGGTCATCCT | 28560 |
| GTCGGGCCGCGACGTCACCTACACGCCCGTGGCCGCGGGGCTGTTGGAGATCCAGGTGCGCGCCTTCAACGCCCTGGGCA | 28640 |
| GTGAGAACCGCACGGTCTGGTGCTGGAGGTTCAGGAGCCGTCCAGTATGTGGCCCTGCAGAGCGGCCCCTGCTTCACCAAC | 28720 |
| CGCTCGGCGCAGTTTGAGGCCGCCACCAGCCCCAGCCCGCGTGTGGCCTACCACTGGGACTTTGGGGATGGGTCGCC | 28800 |
| AGGGCAGGACACAGATGAGCCCAGGCCACGGTGACCGTCCAGGTGCTGCCGGGAGCCGGAGGTGGACGTGGTC | 28880 |
| ACCTGGTGAGCTTCTTCGTGGGCAGCCTGGATCCAGGCCAACTACTTGGAGGCCCACGTTGACCTGCGCGACTGCGTCACCA | 28960 |
| CTGCCCCTGCAGGTGCTGATGCGGCGAAGGTGTATCGCACGGCCAGCTGCCAGCGCCGTGTGGCCCTGCCCG | 29040 |
| CCAGACTGAGTACCGCTGGAGGTGCTGCCGGCGCTGGGGCACTACTGCTTTGTGTTGTCGTG | 29120 |
| GCGTGGACGTGAGCCGGCCCTCGGCTGCTGCCGGCATCCAGGCCAATGTGACGGTGGCCCCCGAGGCCTGGTGCCATCATTGA | 29200 |
| TCATTTGGGGACACGCCACTGACACACCGGCCTGGTGCAGACACGGGACCTGGTGCTGGATGGGAGCGAGTCCTACGACCCCAACCTGGAGG | 29280 |
| GGGTGGCTCATACCGCTGTGTCAGACACGGGACCTGGTGCTGGATGGGAGCGAGTCCTACGACCCCAACCTGGAGG | 29360 |
| ACGGCGACCAGAGCGCCGCTCAGTTCCACTGGGCCTGTGTGGCTTCGACACAGGTCAGTGCGTGGCAGGGCCGTCCTCCA | 29440 |

FIGURE 1X

| | |
|---|---|
| TGCCCCTCACCGTCCACACCGTCCACACCCAGCTTGCCACCAGGGTGGCCCGTCCTCAGTGCCTGGTG | 29520 |
| GGCCCGTCCCAGCATGGGGAGGGGTCTCCCGGCTCTCCCTGGGCCGGCTCTGCTTAAAACTGGATGGGGCTCTC | 29600 |
| AGGCCACGTCGCCCCTTGTTCTCGGCCTGCAGAGGAGGCTGGCGGGTGTGCGCTGAACTTTGGGCCCCGGGGAGCAGC | 29680 |
| ACGGTCACCATTCCAACGGGGAGCGGCTGGCGGCTGGGCGTGGAGTACACCTTCAGCCTGACCGTGTGGAAGGCCGGCCGCAA | 29760 |
| GGAGGAGGCCACCAACCAGACGGTGCCGCCCGGCCCCTCGGCCACTGCCTTGGACAGCCCAGCCTCCCTGGTCATC | 29840 |
| TACTGTTTCGTGTTTAGTGCTGGTGGAGGCCGCACGCTCTCCCCTCTGTTTCTGATGCAAATTCTATGTAACACG | 29920 |
| ACAGCCTGCTTCAGCTTTGCTTCCTTCCAAACCTGCCACAGTTCCACGTACAGTCTTCAAGCCACATATGCTCTAGTGGC | 30000 |
| AAAAGCTACACAGTCCCCTAGCAATACCAACAGTGAGGAAGAGCCCCTTCCCACCCAGAGGTAGCCACTGTCCCCAGCC | 30080 |
| CATGTCCCTGTTGCTGGATGTGGGCCGGTTCTCACCCTCACGNTCCCTCCTCTGGACCGGCCAGGAGGCTGGTGACC | 30160 |
| CTGAGCCCGTGGTGGCTGNNNNNNNNNNNNNNNAGGGCGGNCTGATTGGGGGTCTTCCCAGAGGGGTCGTCTGAGGGGA | 30240 |
| GGGTGTGGGAGCAGGTTCCATCGCGGTCCTCACACCCACATAGCTCTCTTCTCACACGCATCCCCCAGGGGCCCTCAGTGAGCAT | 30320 |
| CCTACGTGGCAGCTGCGGTCCTGCAGGTCCAGTACACCAGAAACGCACACTCCAGTGTCCTCTGCCCTGTGTGAGTCAGG | 30400 |
| TGCCTGCCTCCTGCTAGGGTCCAGTGGGTCCAGTACACCAGAAACGCACACTCCAGTGTCCTCTGCCCTGTATGCCCT | 30480 |
| TCCGCCGTCCAAGTTGGAAGGTGGCAAACGGATGAGTATCCTGGGAGGGAGTGAGCTCACCGGCAGTGGCCAGGCCCCT | 30560 |
| GGGAAACCTGGAGTTTGGGAGCAGCAGCATCCTCCATGGGTCCCCCAGTCCTTCCAGCAGGCCAAATAGACCTGTTGGAGG | 30640 |
| TAACCCCACTCCCAGCGCCAGGTGCTGATCCGGNGTGGCGGGNTGCCNATTGNNNNNNNNNNNNNNTAGGGCGAGTGTGTGT | 30720 |

FIGURE 1Y

```
CCTGCAAGCACAGGGCCGTGTACGAAGTGAGCCGCAGCTCCTACGTGTACTTGGAGGGCCGCTGCCTCAATTGCAGCAGCG   30800
GCTCCAAGCGAGGGGTGAGTGTTGAGCGGGGTGTGTGGGCGGATGGTCCCATGGCCGAGGGACGGGGACGGGGCCTGCA     30880
GGCAGAAGTGGGGCTGACAGGGCAGAGGGTTGCGCCCCTCACCACCCTTCTGCCTCTGCAGCGGTGGCTGCACGTACGT     30960
TCAGCAACAAGACGCTGGTGCTGGATGAGACCACCACATCCACGGGCAGTGCAGGCATGCGACTGGTGCTGCGGCGGGGC   31040
GTGCTGCGGGACGGGCGAGGAGGATACACCTTCACGCTCACGGTGCTGGGCGCTCTGGCGAGGAGGAAGGCTGCGCCTCCAT 31120
CCGCCTGTCCCCCAACCGCCCGCTGGGGGCTCTTGCCGCCTCTTCCCACTGGGCGCTGTGCACGCCCTCACCACCA       31200
AGGTGCACTTCGAATGCACGGGTGAGTGCAGGCCTGCGTGGGGGAGCAGCGGATCCCCGACTCTGTGACGTCACGGA      31280
GCCCTCCCGTGATGCCGTGGGACCGTCCCTCAGGCTGGCATGACGCGGAGGATGCTGGCGCCCCGCTGGTGTACTNCCT   31360
GCTGCTGCGGGCTGTCGCCCAGGGCCACTTCGAGGTGGGCCTGGCCGTGTGGTGCAGGACCAGCTGGGAGCCGTGC      31440
TGCCCCGGGTTTCAGGCCACACTTCGAGGTGGGCCTGGCCCGTGGTGGTGCAGGACCAGCTGGGAGCCGTGTGGTCGCC    31520
CTCAACAGGTGAGCCAGCCGTGGGAGGGCCCCCGAGACTGCCACCTGC                                    31571
```

```
GGTGTGAGGGGTAGGGGCAGGGTGGGAGGTGGGCTCGCGGGTGGGCTGGG       50
GTCATGAAGGGCCTCAGGCGCTCTGCTATTGGGTTCCAAGGCTATCCTGA      100
GAACAGGGGTGAGGGGGATTGCCGTGGGGGTTAAAGCCTTGTCATGTT        150
CGCTTTCGGGAGATAAAAACAAACAGGTGGCCTTTATGGAGACGCTGCCCA     200
GAGCCAGGTCTGTGCCAGGCTCCTGTTGGGGTCGTCATGCGGAATCCTG       250
ACTCTGACCATCCGAGGCATAGGGACCGTGGAGATTTGCATTTCACAGAT      300
GAGGAAACAGGTTTGGAGAGGTGACACGACCTGTCCCAGGCATCACAGCC      350
GGGATGTGCATAGCAGGGGTTTGGAACTATGAGGTGCCAGGACCCAGGG       400
TTGGATTGAAAAGGGCGGAGGGACTAAGATAAGCAGACAGTTGTCCCCA       450
GCGCTGGGGAGAGTCTTGGACCAGTCTGATGCCTTGTATTTCCCAGGCT       500
CCAGGCTCCCTCGCCGGGACAGTGTCTCCTTGGCTGCTGGATCCCTG         550
GGGGACGTGGCACATCCCCAGGCTTGCTAAACATTGGGTGGGTTCTGGCA      600
TTTGGTTTTGTAACGTTTCTGGGTCACTCCCGCCTGTGCCACCCTTCCT       650
TAGGGGAGCCGTGTGTCCTTGGGCTTTGCTGTCTCGAGGGTGGG            700
AGAAGAATGGGTTCTCCTGGACCAATGAGCCCGTGCCCCTCGGGGCCAC       750
ATTGCCTGCGCTCCCTGACTGCCGGACGCGTGTCTCGCGGCTGTCTC         800
TGTGGAGATGGCCTCCTCCTGCCTGGCAACAGCACCCACAGAATTGCATC      850
AGACCTACCCCACCCGTTGTTTGATGCTGTAGCTGTGAGGGCTC            894
```

```
Homologue  5' GGAAACAGGT TTGGAGAGGT GACACGACCT GTCCCAGGCA TCACAGCCAG
Authentic  5' GGAAACAGGT TTGGAGAGGT GACACGACCT GTC::::::: :::::::::

GACAGGACCT GTCCAGGCAT CACAGCCGGG ATGTGCATAG CAGGGGTTTG
           ::::::::: ::CCAGGCAT CACAGCCGGG ATGTGCATAG CAGGGGTTTG

GAACTATGAG GTGCCCAGGA CCCAGGGTTG GATTGAAAAG GGCGCAGGGG ACTAAGATAA-3'
           GAACTATGAG GTGCCCAGGA CCCAGGGTTG GATTGAAAAG GGCGCAGGGG ACTAAGATAA-3'
```

FIGURE 3B

5'-AGGGACCTGTCCAGGCATC*-3'

POLYCYSTIC KIDNEY DISEASE GENE

FIELD OF THE INVENTION

The present invention pertains to the diagnosis and treatment of polycystic kidney disease in humans, using DNA sequences derived from the human PKD1 gene and the protein or proteins encoded by that gene.

BACKGROUND OF THE INVENTION

Autosomal dominant polycystic kidney disease (APKD), also called adult-onset polycystic kidney disease, is one of the most common hereditary disorders in humans, affecting approximately one individual in a thousand. The prevalence in the United States is greater than 500,000, with 6,000 to 7,000 new cases detected yearly (Striker et al., *Am. J. Nephrol.*, 6:161–164, 1986; Iglesias et al., *Am. J. Kid. Dis.*, 2:630–639, 1983). The disease is considered to be a systemic disorder, characterized by cyst formation in the ductal organs (kidney, liver, pancreas), as well as by gastrointestinal, cardiovascular, and musculoskeletal abnormalities (including colonic diverticulitis, berry aneurysms, hernias, and mitral valve prolapse) (Gabow et al., *Adv. Nephrol*, 18:19–32, 1989; Gabow, *New Eng. J. Med.*, 329:332–342, 1993).

The most prevalent and obvious symptom of APKD, however, is the formation of kidney cysts, which result in grossly enlarged kidneys and a decrease in renal-concentrating ability. Hypertension and endocrine abnormalities are also common in APKD patients, appearing even before symptoms of renal insufficiency. In approximately half of APKD patients, the disease progresses to end-stage renal disease; accordingly, APKD is responsible for 4–8% of the renal dialysis and transplantation cases in the United States and Europe (*Proc. European Dialysis and Transplant Assn.*, Robinson and Hawkins, eds., 17:20, 1981). Thus, there is a need in the art for diagnostic and therapeutic tools to reduce the incidence and severity of this disease.

APKD exhibits a transmission pattern typical of autosomal dominant inheritance i.e. each offpsring of an affected individual has a 50% chance of inheriting the causative gene. Linkage studies indicated that a causative gene is present on the short arm of chromosome 16, near the α-globin cluster; this locus was designated PKD1 (Reeders et al., *Nature*, 317:542, 1985.) Though other PKD-associated genes exist e.g. PKD2, PKD1 defects appear to cause APKD in about 85–90% of affected families (Parfrey et al., *New Eng. J. Med.*, 323:1085–1090, 1990; Peters et at., *Contrib. Nephrol.*, 97:128–139, 1992).

The PKD1 gene has been localized to chromosomal position 16p13.3. Using extensive linkage analysis, in conjunction with the identification of new markers and restriction enzyme analysis, the gene has been further localized to an interval of approximately 600 kb between the markers ATPL and CMM65 (D16S84). The region is rich in CpG islands that are thought to flank transcribed sequences, and it has been estimated that this interval contains at least 20 genes. The precise location of the PKD1 gene was pinpointed by the finding of a PKD family whose affected members carry a translocation that disrupts a 14 kb RNA transcript associated with this region (European PKD Consortium, *Cell*, 77:881, 1994). This article discloses approximately 5 kb of DNA sequence corresponding to the 3' end of the putative PKD1 cDNA sequence.

Notwithstanding knowlege of the partial PKD1 3' cDNA sequence, several significant impediments stand in the way of determining the complete sequence of the PKD1 gene. For the most part, these impediments arise from the complex organization of the PKD1 locus. One serious obstacle is that sequences related to the PKD1 transcript are duplicated at least three times on chromosome 16 proximal to the PKD1 locus, forming PKD1 homologues. Another obstacle is that the PKD1 genomic interval also contains repeat elements that are present in other genomic regions. Both of these types of sequence duplications interfere with "chromosome walking" techniques that are widely used for identification of genomic DNA. This is because these techniques rely on hybridization to identify clones containing overlapping fragments of genomic DNA; thus, there is a high likelihood of "walking" into clones derived from PKD1 homologues instead of clones derived from the authentic PKD1 gene. In a similar manner, the PKD1 duplications and chromosome 16-specific repeats also interfere with the unambiguous determination of a complete cDNA sequence that encodes the PKD1 protein. Thus, there is a need in the art for genomic and cDNA sequences corresponding to the authentic PKD1 gene. This includes identification of segments of these sequences that are unique to the expressed PKD1 and not are present in the duplicated homologous sequences also present on chromosome 16.

SUMMARY OF THE INVENTION

The present invention involves an isolated normal human PKD1 gene having the sequence set forth in FIG. 1, an isolated intronless nucleic acid having the PKD1 cDNA sequence set forth in FIG. 2, and sequences derived therefrom. The PKD1 gene is a genomic DNA sequence whose altered, defective, or non-functional expression leads to adult-onset polycystic kidney disease. The invention also encompasses DNA vectors comprising these nucleic acids, cells transformed with the vectors, and methods for producing PKD1 protein or fragments thereof.

In another aspect, the invention involves isolated oligonucleotides that hybridize only to the authentic expressed PKD1 gene, and not to PKD1 homologues.

In yet another aspect, the invention involves isolated mutant PKD1 genes, and their cDNA cognates, which contain alterations in nucleotide sequence relative to the normal PKD1 gene, and whose presence in one or more copies in the genome of a human individual is associated with adult-onset polycystic kidney disease.

In still another aspect, the invention involves isolated oligonucleotides that discriminate between normal and mutant versions of the PKD1 gene.

In still another aspect, the invention involves methods for identifying a human subject carrying a mutant PKD1 gene in a human subject, comprising:

a) obtaining a sample of biological material from the subject, and b) detecting the presence of the mutant gene or its protein product.

BRIEF DESCRIPTION OF THE DRAWINGS

FIG. 1 depicts the arrangement of FIGS. 1A through 1Y which show the DNA sequence of 31,571 bases comprising the 5' region of the normal human PKD1 gene.

FIG. 2 shows the partial DNA sequence of 894 bases comprising the 5' region of normal human PKD1 cDNA SEQ. ID. NO. 2.

FIG. 3A shows a comparison of the DNA sequence of the 5' region of cDNAs derived from the authentic PKD1 gene and PKD1 homologues SEQ. ID. NO. 3. A 29-base pair gap must be introduced into the sequence of the authentic gene to align the two sequences. In addition, the authentic PKD1 cDNA and the PKD1 homologue cDNA differ at position 418. FIG. 3B shows the DNA sequence of an oligonucleotide SEQ. ID. NO. 8 that can be used to discriminate between the authentic PKD1 sequence and PKD1 homologues. The star denotes a polymerization-blocking modification.

DETAILED DESCRIPTION OF THE INVENTION

Figure 4:
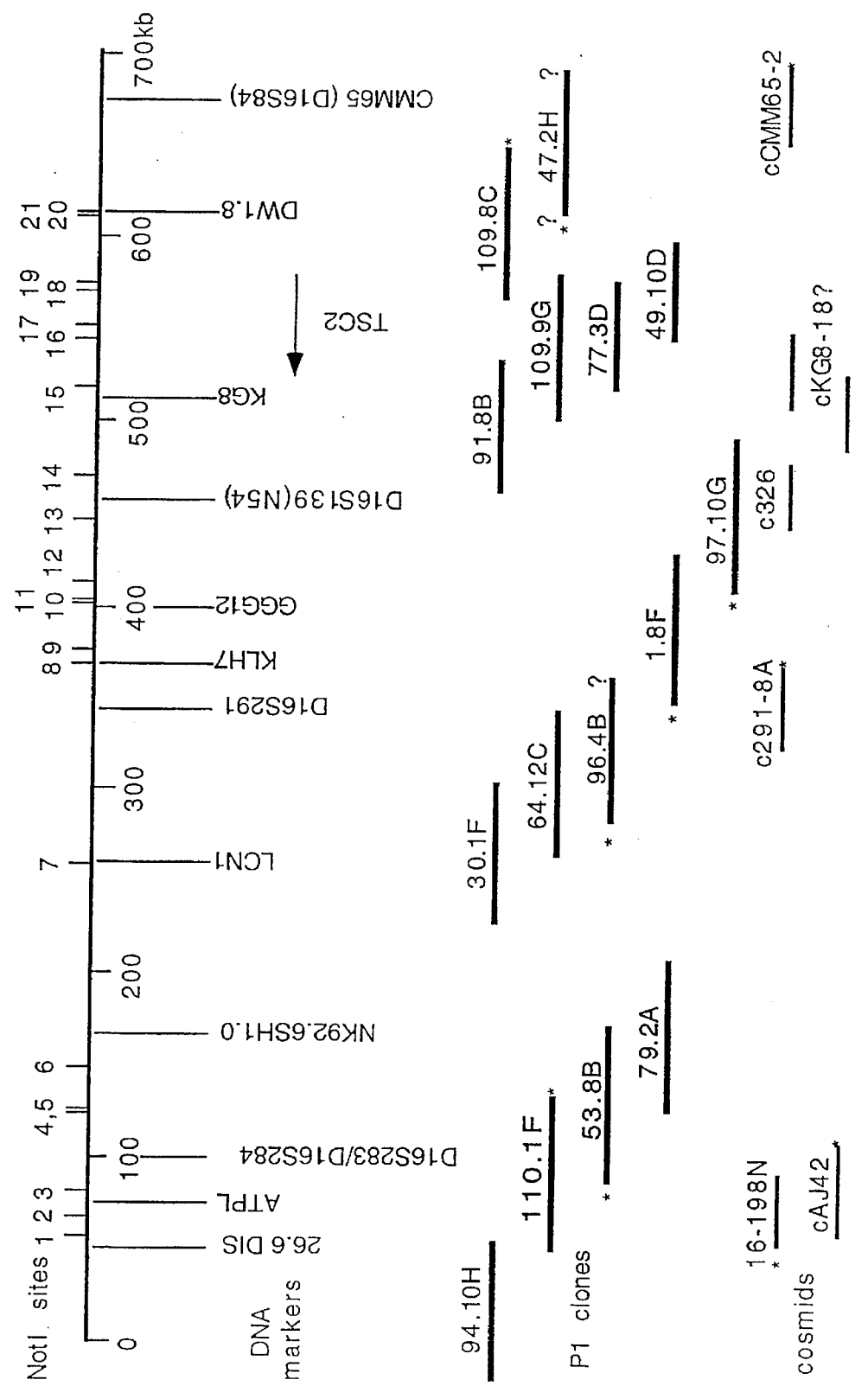
FIG. 4 shows the region of chromosome 16 containing the PKD1 locus. The upper panel shows NotI restriction sites, as well as previously identified genetic markers in this region. The bottom panel shows P1 clones covering this region.

All patent applications, patents, and literature references cited in this specification are hereby incorporated by reference in their entirety. In case of conflict or inconsistency, the present description, including definitions, will control.

Definitions

1. "APKD" as used herein denotes adult-onset polycystic kidney disease, which is characterized by the development of renal cysts and, ultimately, renal failure, and may alternatively or in addition involve cysts in other organs including liver and spleen, as well as gastrointestinal, cardiovascular, and musculoskeletal abnormalities.

2. The term "PKD1 gene" refers to a genomic DNA sequence which maps to chromosomal position 16p13.3 and gives rise to a messenger RNA molecule encoding the PKD1 protein. The PKD1 gene encompasses the sequence shown in FIG. 1, which includes introns and putative regulatory sequences. The term "authentic" is used herein to denote the genomic sequence at this location, as well as sequences derived therefrom, and serves to distinguish these authentic sequences from "PKD1 homologues" (see below.)

3. "PKD1 complementary DNA (cDNA)" is defined herein as a single-stranded or double-stranded intronless DNA molecule that is derived from the authentic PKD1 gene and whose sequence, or complement thereof, encodes the PKD1 protein.

4. A "normal" PKD1 gene is defined herein as a PKD1 gene whose altered, defective, or non-functional expression leads to adult-onset polycystic kidney disease. A normal PKD1 gene is not associated with disease and thus is considered to be a wild-type version of the gene. Included in this category are allelic variants in the PKD1 gene, also denoted allelic polymorphisms i.e. alternate versions of the PKD1 gene, not associated with disease, that may be represented at any frequency in the population. Also included are alterations in DNA sequence, whether recombinant or naturally occurring, that have no apparent effect on expression or function of the PKD1 gene product.

5. A "mutant" PKD1 gene is defined herein as a PKD1 gene whose sequence has been modified by transitions, transversions, deletions, insertions, or other modifications relative to the normal PKD1 gene, which modifications cause detectable changes in the expression or function of the PKD1 gene product, including causing disease. The modifications may involve from one to as many as several thousand nucleotides, and result in one or more of a variety of changes in PKD1 gene expression e.g. decreased or increased rates of expression, or expression of a defective RNA transcript or protein product. Mutant PKD1 genes encompass those genes whose presence in one or more copies in the genome of a human individual is associated with APKD.

6. A "PKD1 homologue" is a sequence which is closely related to PKD1, but which does not encode the authentic expressed PKD1 gene product. Several examples of such homologues that map to chromosomal location 16p13.1 have been identified and sequenced by the present inventors.

7. A "PKD1 carrier" is defined herein as an individual who carries at least one copy of a disease-producing mutant PKD1 gene. Since the disease generally exhibits an autosomal dominant pattern of transmission, PKD1 carriers have a high probability of developing some symptom of PKD. Thus, a PKD1 carrier is likely to be a "PKD patient."

8. As referred to herein, a "contig" is a continuous stretch of DNA or DNA sequence, which may be represented by multiple, overlapping clones or sequences.

9. As referred to herein, a "cosmid" is a DNA plasmid that can replicate in bacterial cells and that accomodates large DNA inserts of from about 30 to about 45 kb in length.

10. The term "P1 clones" refers to genomic DNAs cloned into vectors based on the P1 phage replication mechanisms. These vectors generally accomodate inserts of about 80 to about 120 kb (Pierce et al., *Proc. Natl. Acad. Sci., USA*, 89:2056–2060, 1992).

11. As used herein, the term "exon trapping" refers to a method for isolating genomic DNA sequences that are flanked by donor and acceptor splice sites for RNA processing.

12. The term "single-strand conformational polymorphism analysis" (SSCP) refers to a method for detecting sequence differences between two DNAs, comprising hybridization of the two species with subsequent mismatch detection by gel electrophoresis. (Ravnik-Glavac et al., *Hum. Mol. Genet.*, 3:801, 1994.)

13. "HOT cleavage" is defined herein as a method for detecting sequence differences between two DNAs, comprising hybridization of the two species with subsequent mismatch detection by chemical cleavage (Cotton, et al., *Proc. Natl. Acad. Sci., USA*, 85:4397, 1988).

14. "Denaturing gradient gel electrophoresis" (DDGE) refers to a method for resolving two DNA fragments of identical length on the basis of sequence differences as small as a single base pair change, using electrophoresis through a gel containing varying concentrations of denaturant (Guldberg et al., *Nuc. Acids Res.*, 22:880, 1994.)

15. As used herein, "sequence-specific oligonucleotides" refers to related sets of oligonucleotides that can be used to detect allelic variations or mutations in the PKD1 gene.

16. As used herein, "PKD1-specific oligonucleotides" refers to oligonucleotides that hybridize to sequences present in the authentic expressed PKD1 gene and not to PKD1 homologues or other sequences.

17. "Amplification" of DNA as used herein denotes a reaction that serves to increase the concentration of a particular DNA sequence within a mixture of DNA sequences. Amplification may be carded out using polymerase chain reaction (PCR; Saiki et al., *Science*, 239:487, 1988), ligase chain reaction (LCR), nucleic acid-specific based amplification (NSBA), or any method known in the art.

18. "RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

19. A PKD1 gene or PKD1 cDNA, whether normal or mutant, that "consists essentially of" a particular sequence, is understood to include alterations in the particular sequence that do not change the inherent properties of the sequence. It will be understood that additional nucleotides may be added to the 5' and/or 3' terminus of the disclosed sequence, as part of routine recombinant DNA manipulations. Furthermore, conservative DNA substitutions i.e. changes in the sequence of the protein-coding region that do not change the encoded amino acid sequence, may also be accomodated.

The present invention encompasses the human gene for PKD1. Mutations in this gene are associated with the occurrence of adult-onset polycystic kidney disease. A "normal" version of the genomic sequence, corresponding to 31,571 bases of the 5' end of the PKD1 gene is shown in FIG. 1.

The PKD1 gene sequence was determined using the strategy described in Example 1. Briefly, a series of cosmid and P1 DNA clones was assembled containing overlapping human genomic DNA sequences that collectively cover a 750 kilobase segment of chromosome 16 known to contain the PKD1 locus. To identify transcribed sequences within this 750 kb segment, including those sequences encoding PKD1, both exon trapping and cDNA selection techniques were employed. At the same time, direct DNA sequencing of the human DNA sequences contained in the genomic clones was performed, using techniques that are well-known in the art. These included the isolation of subclones from particular cosmid or P1 clones. Nested deletions were then created from selected subclones, and the nested deletions were then subjected to direct DNA sequencing using the ALF™ automated sequencer (Pharmacia, Uppsala, Sweden).

A partial sequence of PKD1 cDNA is shown in FIG. 2. This 5' cDNA fragment, comprising 894 bases, spans nucleotides 3393 to 4287 of the sequence shown in FIG. 1.

The present invention encompasses isolated oligonucleotides corresponding to sequences within the PKD1 gene, or within PKD1 cDNA, which, alone or together, can be used to discriminate between the authentic expressed PKD1 gene and PKD1 homologues or other repeated sequences. These oligonucleotides may be from about 12 to about 60 nucleotides in length, preferably about 18 nucleotides; may be single- or double-stranded, and may be labelled or modified as described below. An example of an oligonucleotide that can be used in this manner is shown in FIG. 3B. The discrimination function of this oligonucleotide is based on a comparison of the sequence of the authentic PKD1 gene with three cDNAs derived from the PKD1 homologues, which revealed that homologue cDNAs contain a 29 bp insertion relative to the authentic PKD1 sequence (FIG. 3A). The oligonucleotide shown in FIG. 3B is modified at its 3' terminus so that it does not support polymerization reactions, and is designed to hybridize specifically to the homologue sequence and not to the authentic PKD1 sequence. When this oligonucleotide is included in amplification reactions, it selectively prevents the amplification of PKD1 homologue sequences. In this manner, authentic PKD1 sequences are selectively amplified and PKD1 homologues are not. These oligonucleotides or their functional equivalents thus provide a basis for testing for the presence of mutations in the authentic PKD1 gene in a human patient (see Example 3 below.)

The present invention encompasses isolated DNA and RNA sequences, including sense and antisense sequences, derived from the sequences shown in FIGS. 1, 2, and 3. The particular sequences may represent "normal" alleles of PKD1, including allelic variants, or "mutant" alleles, which are associated with disease symptoms. PKD1-derived sequences may also be associated with heterologous sequences, including promoters, enhancers, response elements, signal sequences, polyadenylation sequences, and the like. Furthermore, the nucleic acids can be modified to alter stability, solubility, binding affinity, and specificity. For example, PKD1-derived sequences can be selectively methylated.

The DNA may comprise antisense oligonucleotides, and may further include nuclease-resistant phosphorothioate, phosphoroamidate, and methylphosphonate derivatives, as well as "protein nucleic acid" (PNA) formed by conjugating bases to an amino acid backbone as described in Nielsen et al., 1991, Science, 254: 1497. The DNA may be derivatized by linkage of the a-anomer nucleotide, or by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in e.g. *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The invention also provides vectors comprising nucleic acids having PKD1 or PKD1-related sequences. A large number of vectors, including plasmid and fungal vectors, have been described for expression in a variety of eukaryotic and prokaryotic hosts, and may be used for gene therapy as well as for simple protein expression. Advantageously, vectors may also include a promoter operably linked to the PKD1 encoding portion, particularly when the PKD1-encoding portion comprises the cDNA shown in FIG. 2 or derivatives or fragments thereof. The encoded PKD1 may be expressed by using any suitable vectors, such as pRSET or pREP (Invitrogen, San Diego, Calif.), and any suitable host cells, using methods disclosed or cited herein or otherwise known to those skilled in the relevant art. The particular choice of vector/host is not critical to the operation of the invention.

Recombinant cloning vectors will often include one or more replication systems for cloning or expression, one or more markers for selection in the host, e.g. antibiotic resistance, and one or more expression cassettes. The inserted PKD1 coding sequences may be synthesized, isolated from natural sources, or prepared as hybrids, etc. Ligation of the PKD1 coding sequences to transcriptional regulatory elements and/or to other amino acid coding sequences may be achieved by known methods. Suitable host cells may be transformed/transfected/infected by any suitable method including electroporation, CaCl$_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *E. coli, B. Subtilis, Saccharomyces cerevisiae,* SF9 cells, C129 cells, 293 cells, *Neurospora,* and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced PKD1.

Nucleic acids encoding PKD1 polypeptides may also be introduced into cells by recombination events. For example, such a sequence can be microinjected into a cell, and thereby effect homologous recombination at the site of an endogenous gene encoding PKD1, an analog or pseudogene thereof, or a sequence with substantial identity to a PKD1-encoding gene. Other recombination-based methods such as nonhomologous recombinations or deletion of endogenous gene by homologous recombination, especially in pluripotent cells, may also be used.

The present invention also encompasses an isolated polypeptide having a sequence encoded by the authentic PKD1 gene, as well as peptides of six or more amino acids derived therefrom. The polypeptide(s) may be isolated from human tissues obtained by biopsy or autopsy, or may be produced in a heterologous cell by recombinant DNA methods as described above. Standard protein purification methods may be used to isolate PKD1-related polypeptides, including but not limited to detergent extraction, and chromatographic methods including molecular sieve, ion-exchange, and affinity chromatography using e.g. PKD1-specific antibodies or ligands. When the PKD1-polypeptide to be purified is produced in a recombinant system, the recombinant expression vector may comprise additional sequences that encode additional carboxyterminal amino acids; these extra amino acids act as "tags" for immunoaffinity purification using commercially available antibodies.

Peptides comprising PKD1-specific sequences may be derived from isolated larger PKD1 polypeptides described above, using proteolytic cleavages by e.g. proteases such as trypsin and chemical treatments such as cyanogen bromide that are well-known in the art. Alternatively, peptides up to 60 residues in length can be routinely synthesized in milligram quantities using commercially available peptide synthesizers.

The present invention encompasses antibodies that specifically recognize PKD1 polypeptide encoded by the gene shown in FIG. 1 or the cDNA shown in FIG. 2, and/or fragments or portions thereof. The antibodies may be polyclonal or monoclonal, may be produced in response to the native PKD1 polypeptide or to synthetic peptides as described above. Such antibodies are conveniently made using the methods and compositions disclosed in Harlow and Lane, *Antibodies, A Laboratory Manual,* Cold Spring Harbor Laboratory, 1988, other references cited herein, as well as immunological and hybridoma technologies known to those in the art. Where natural or synthetic PKD1-derived peptides are used to induce a PKD1-specific immune response, the peptides may be conveniently coupled to an suitable carrier such as KLH and administered in a suitable adjuvant such as Freunds. Preferably, selected peptides are coupled to a lysine core carrier substantially according to the methods of Tam, *Proc. Natl. Acad. Sci, USA* 85:5409–5413, 1988. The resulting antibodies may be modified to a monovalent form e.g. Fab, FAB', or FV. Anti-idiotypic antibodies may also be prepared using known methods.

In one embodiment, normal or mutant PKD1 polypeptides are used to immunize mice, after which their spleens are removed, and splenocytes used to form cell hybrids with myeloma cells and obtain clones of antibody-secreted cells according to techniques that are standard in the art. The resulting monoclonal antibodies are screened for specific binding to PKD1 proteins or PKD1-related peptides.

In another embodiment, antibodies are screened for selective binding to normal or mutant PKD1 sequences. Antibodies that distinguish between normal and mutant forms of PKD1 may be used in diagnostic tests (see below) employing ELISA, EMIT, CEDIA, SLIFA, and the like. Anti-PKD 1 antibodies may also be used to perform subcellular and histochemical localization studies. Finally, antibodies may be used to block the function of the PKD1 polypeptide, whether normal or mutant, or to perform rational drug design studies to identify and test inhibitors of the function (e.g. using an anti-idiotypic antibody approach.)

Identification of Disease-Causing Mutations in PKD1

In practicing the present invention, the isolated and sequenced PKD1 gene is utilized to identify new mutant versions of the PKD1 gene. First, human subjects with inherited polycystic kidney disease are identified by clinical testing, pedigree analysis, and linkage analysis, using standard diagnostic criteria and interview procedures, and DNA or RNA samples are obtained from the subjects (see below).

A variety of techniques are then employed to pinpoint new mutant sequences. First, PKD1 DNA may be subjected to direct DNA sequencing, using methods that are standard in the art. Furthermore, deletions may be detected using a PCR-based assay, in which pairs of olignucleotides are used to prime amplification reactions and the sizes of the amplification products are compared with those of control products. Other useful techniques include Single-Strand Conformation Polymorphism analysis (SSCP), HOT cleavage, denaturing gradient gel electrophoresis, and two-dimensional gel electrophoresis.

A confounding and complicating factor in the detection of a PKD1 mutation is the presence of PKD1 homologues at several sites on chromosome 16 proximal to the transcribed gene. In analysis of mutations in PKD1, it is critical to distinguish between sequences derived from the authentic PKD1 gene and sequences derived from any of the homologues. Thus, an important feature of the present invention is the provision of oligonucleotide primers that discriminate between authentic PKD1 and the homologues. A detailed comparison of the sequences of the authentic PKD1 gene and the homologues enables the design of primers that discriminate between the authentic PKD1 gene or cDNA and the homologues. Primers that conform to this criterion, such as those disclosed in FIG. 3B, may be used in conjunction with any of the analytical methods described below.

For SSCP, primers are designed that amplify DNA products of about 250–300 bp in length across non-duplicated segments of the PKD1 gene. For each amplification product, one gel system and two running conditions are used. Each amplification product is applied to a 10% polyacrylamide gel containing 10% glycerol. Separate aliquots of each amplimer are subjected to electrophoresis at 8 W at room temperature for 16 hours and at 30 W at 4° C. for 5.4 hours. These conditions were previously shown to identify 98% of the known mutations in the CFTR gene (Ravnik-Glavac et at., *Hum. Mol. Genet.*, 3:801, 1994.)

For "HOT" cleavage, amplification reactions are performed using radiolabelled PKD1-specific primers. Each radiolabelled amplification product is then mixed with a 10-fold to 100-fold molar excess of unlabelled amplification products produced using the identical primers and DNA from APKD-affected or -unaffected subjects. Heteroduplex formation, chemical cleavage, and gel analysis are then performed as described (Cotton, et at., *Proc. Natl. Acad. Sci., USA*, 85:4397, 1988). Bands on the gel that are smaller than the homoduplex result from chemical cleavage of heteroduplexes at base pair mismatches involving cytidine or thymidine. Once a mutation has been identified by this procedure, the exact location of the mismatch(es) is determined by direct DNA sequencing.

Mutations are also identified by "broad range" DDGE (Guldberg et al., *Nuc. Acids Res.*, 22:880, 1994.) The use of GC-clamped PCR primers and a very broad denaturant gradient enables the efficient detection of mutant sequences. This method can also be combined with non-denaturing size fractionation in a two-dimensional system. An apparatus is used that permits automated two-dimensional electrophoresis, and the second dimension considerably increases the resolution of mutations.

After the presence of a mutation is detected by any of the above techniques, the specific nucleic acid alteration comprising the mutation is identified by direct DNA sequence analysis. In this manner, "novel" i.e. previously unidentified PKD1 mutations may be defined.

Once a novel PKD1 mutation is defined, methods for detecting the particular mutation in other affected individuals can be devised, using a variety of methods that are standard in the art. For example, oligonucleotide probes may be prepared that allow the detection and discrimination of the particular mutation. It will be understood that such probes may comprise either the mutant sequence itself, or, alternatively, may flank the mutant sequence. Furthermore, the oligonucleotide sequence can be used to design a peptide immunogen comprising the mutant amino acid sequence. These peptides are then used to elicit antibodies that distinguish between normal and mutant PKD1 polypeptides.

Diagnostic Tests for PKD1 Mutations

Mutant PKD1 genes, whether identified by the methods described above or by other means, find use in the design and operation of diagnostic tests. Tests that detect the presence of mutant PKD1 genes, including those described below and in Example 4, can be applied in the following ways:

(1) To determine donor suitability for kidney transplants. In general, it is desirable to use a close relative of the transplant recipient. When the recipient is a patient suffering from familial APKD, it is important to ascertain that the donor relative does not also carry the familial mutant PKD1 gene.

(2) To screen for at-risk individuals in APKD-affected families. Presymptomatic individuals who have a high probability of developing APKD can be identified, allowing them to be monitored and to avail themselves of preventive therapies.

(3) To target hypertensive patients for antihypertensive treatment. Hypertension is also linked to APKD. Screening of hypertensive patients for the presence of mutant PKD1 genes can be used to identify patients for pre-emptive regulation of blood pressure to prevent later kidney damage.

(4) To perform prenatal screening. Most PKD1-linked PKD is of the adult-onset type. In a small subset of families carrying a mutation in PKD1 genes, however, juvenile onset is common and signifies a more severe form of the disease. In these families, prenatal screening can be useful for genetic counselling purposes.

In general, the diagnostic tests according to the present invention involve obtaining a biological sample from a subject, and screening the sample for the presence of one or more mutant versions of the PKD1 gene or its protein product. The subject may be a fetus in utero, or a human patient of any age.

In one embodiment, a sample of genomic DNA is obtained from a human subject and assayed for the presence of one or more disease-associated PKD1 mutations. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, amniotic fluid, and tissue exudates at the site of infection or inflammation. DNA is extracted from the cell source or body fluid using any of the numerous methods that are standard in the art. It will be understood that the particular method used to extract DNA will depend on the nature of the source. The minimum amount of DNA to be extracted for use in the present invention is about 25 pg (corresponding to about 5 cell equivalents of a genome size of $4 \times 10^9$ base pairs).

In this embodiment, the assay used to detect the presence of mutations may comprise restriction enzyme digestion, direct DNA sequencing, hybridization with sequence-specific oligonucleotides, amplification by PCR, single-stranded conformational polymorphism analysis, denaturating gradient gel electrophoresis (DDGE), two-dimensional gel electrophoresis, in situ hybridization, and combinations thereof.

In a preferred embodiment, RNA is isolated from a PKD1-expressing cell or tissue, preferably lymphocytes, using standard techniques including automated systems such as that marketed by Applied Biosystems, Inc. (Foster City, Calif.). The RNA is then subjected to coupled reverse-transcription and PCR amplification (RT-PCR). The resulting DNA may then be screened for the presence of mutant sequences by any of the methods outlined above (see Example 3 below).

As discussed above, any nucleic-acid-based screening method for PKD1 mutations must be able to discriminate between the authentic PKD1 gene present at chromosome location 16p13.3 and PKD1 homologues present at 16p13.1 and other locations. The oligonucleotides shown in FIG. 3 are examples of primers that discriminate between the authentic and homologue sequences, and these oligonucleotides or their equivalents form an important part of any such diagnostic test.

In another embodiment, the assay used to detect the presence of a mutant PKD1 gene involves testing for mutant gene products by an immunological assay, using one of many methods known in the art e.g. radioimmunoassay, ELISA, immunfluorescence, and the like. In this embodiment, the biological sample is preferably derived from a PKD1-expressing tissue such as kidney. The PKD1 polypeptide may be extracted from the sample. Alternatively, the sample may be treated to allow detection or visualization of specifically bound antibodies in situ as occurs in e.g. cryosectioning followed by immunofluorescent staining.

The antibodies may be monoclonal or polyclonal, may be raised against intact PKD1 protein, or natural or synthetic peptides derived from PKD1. In a preferred embodiment, the antibodies discriminate between "normal" and "mutant" PKD1 sequences, and possess a sufficiently high affinity for PKD1 polypeptides so that they can be used in routine assays.

It will be understood that the particular method or combination of methods used will depend on the particular application. For example, high-throughput screening methods preferably involve extraction of DNA or RNA from an easily available tissue, followed by amplification of particular PKD1 sequences and hybridization of the amplification products with a panel of specific oligonucleotides.

Therapeutic Applications

The present invention encompasses the treatment of PKD using the methods and compositions disclosed herein. The intact normal PKD1 gene disclosed above can be delivered to kidney cells or other affected cells using a variety of known methods, including e.g. liposomes, vital vectors, recombinant viruses, and the like. The gene can be incorporated into DNA vectors that additionally comprise tissue-specific regulatory elements, allowing PKD1 expression in a tissue-specific manner. This approach is feasible if a particular mutant PKD1 allele, when present in a single copy, merely causes the level of the PKD1 protein to diminish below a threshold level necessary for normal function; in this case, increasing the gene dosage by supplementing with additional normal copies of the PKD1 gene should correct the functional defect. Alternatively, it may be desired to limit the expression of a mutant PKD1 gene, using e.g. antisense sequences. In this embodiment, antisense oligonucleotides may be delivered to kidney or other cells.

For therapeutic uses, PKD1-related DNA may be administered by any convenient way, e.g. parenterally, in a physiologically acceptable carrier, e.g., phosphate buffered saline, saline, deionized water, or the like. Typically, the compositions are added to a retained physiological fluid such as blood or synovial fluid. The amount administered will be empirically determined using routine experimentation. Other additives may be included, such as stabilizers, bactericides, and the like, are present in conventional mounts.

The following examples are intended to illustrate the invention without limiting its scope thereof.

Example 1: Cloning and Sequencing of the Human PKD1 gene

Figure 5:
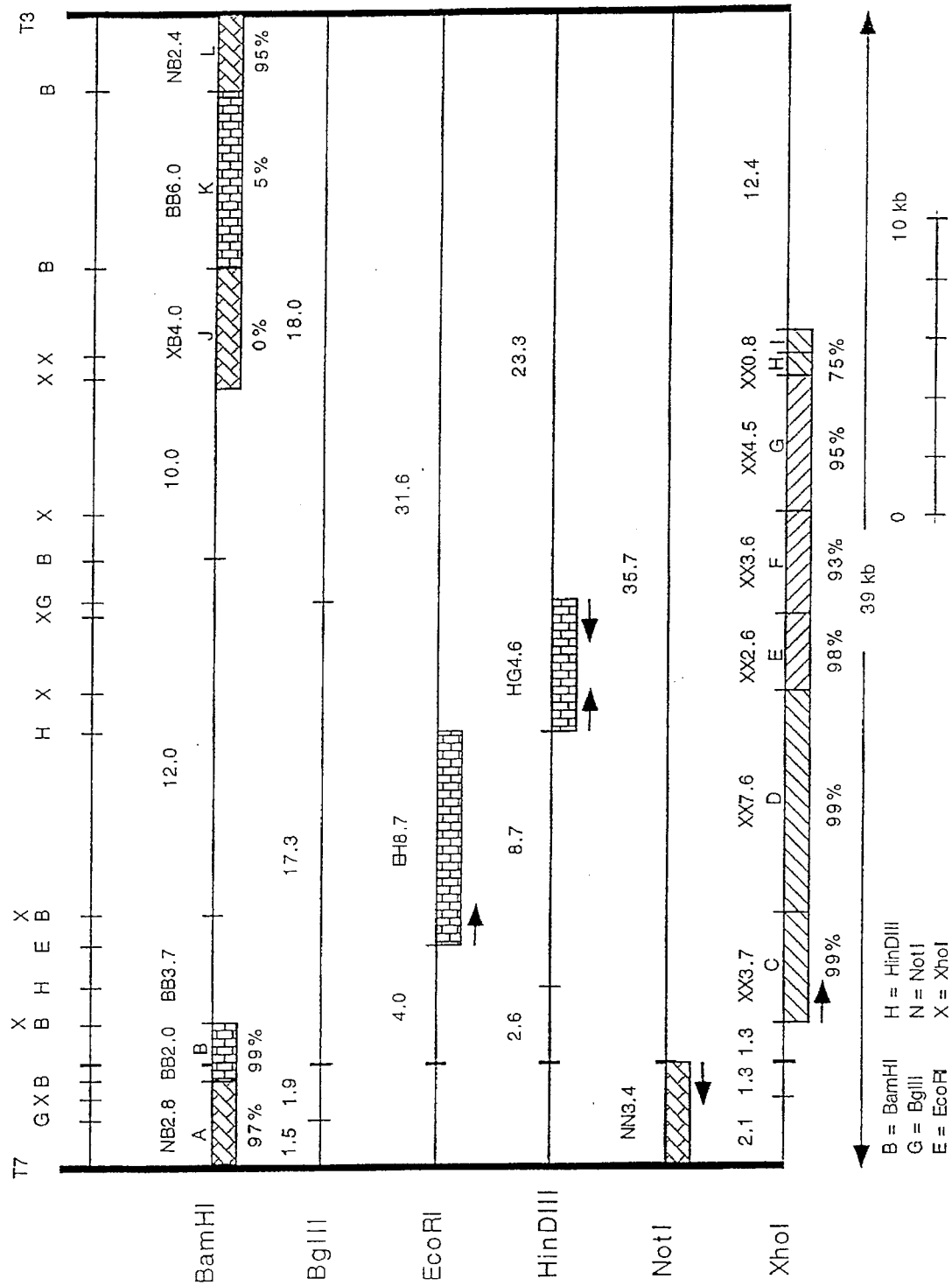
FIG. 5 shows a restriction map of a cosmid clone designated cGGG10.2, which contains the major portion of the authentic PKD1 gene, as well as subclones derived therefrom.

A 700 kbp region of chromosome 16 containing the PKD1 locus is shown in FIG. 4 (top panel.) A contig covering this region was assembled from overlapping P1 clones (shown in the middle panel); clone 91.8B contains the entire PKD1 gene. The contig was assembled by unidirectional chromosomal walking from the ends of the interval (ATPL and D16S84) and bidirectional walking from several internal loci (D16S139 and KG8). The PKD1 sequence is also contained within a cosmid clone designated cGGG10.2, which is represented schematically in FIG. 5. A partial restriction map of the insert contained within this clone is diagrammed on the top line of the figure. Based on the restriction map, individual fragments (labelled A through K2 as indicated in FIG. 5) were isolated and subcloned into vectors so that the inserted sequences are flanked on either end by defined sequencing primer sequences e.g. T3 or T7.

In a second step, each subclone was used to create nested set of deletion subclones, using standard procedures for generating deletions such as exonuclease digestion followed by religation. Finally, the inserts contained in each deletion subclone were subjected to automated DNA sequencing using e.g. T3 and T7-specific sequencing primers and the ALF™ automated sequencing system (Pharmacia, Uppsala, Sweden).

In a second phase, ambiguities and gaps in the above sequence were resolved by an additional round of sequencing using oligonucleotide primers corresponding to nearby sequences identified in the previous step. Finally, the sequences were compared to sequences obtained from cDNA selection and exon trapping techniques (see below), and were analyzed for known sequences and sequence motifs (at both the DNA and protein level) using various commercially available search programs.

In this manner, the sequence of PKD1 genomic DNA shown in FIG. 1 was obtained.

Example 2: PKD1 cDNA Sequences Obtained Through Exon Trapping and cDNA Selection Techniques The 700 kbp interval of chromosome 16 that includes the PKD1 gene appears to be particularly rich in CpG islands and, by association, is most likely rich in expressed sequences as well. To purify and sequence expressed PKD1 sequences, an exon-rescue vector, pSPL3, was used to recover sequences from cosmids that contain both a splice acceptor and splice donor element; this method is designated "exon trapping." The application of this method, in conjunction with standard subcloning, amplification, and DNA sequencing methods, allowed the determination of PKD1 cDNA sequence as shown in FIG. 2.

Exon trapping is a highly efficient method for isolating expressed sequences from genomic DNA. The procedure utilizes the pSPL3 plasmid, which contains rabbit 6-globin coding sequences separated by a portion of the HIV-tat gene, or improved derivatives of SPL3 lacking cryptic (interfering) splice sites. Fragments of cloned PKD1 genomic DNA were cloned into the intron of the tat gene, and the resulting subclones were transfected into COS-7 cells. SV40 sequences in the vector allow for both relaxed episomal replication of the transfected vectors, as well as transcription of the cloned genomic DNAS. Exons within the subcloned genomic DNAs spliced into the globin/tat transcript were recovered using RT-PCR, using primers containing tat splice donor and acceptor sequences. A major advantage of exon trapping is that expression of the cloned DNA is directed by a vital promoter; thus, developmental or tissue-specific expression of gene products is not a concern.

PKD1-containing genomic clones, in the form of either cosmid or P1 DNA, were either double digested with BamHI and BglII or partially digested with Sau3A and shotgun cloned into BamHI-digested and dephosphorylated pSPL3 (GIBCO BRL, Bethesda, Md.) or its derivatives. Plasmid minipreps were electroporated into COS-7 cells, and trapped exons were recovered by RT-PCR, followed by subcloning, using standard procedures.

Figure 6:
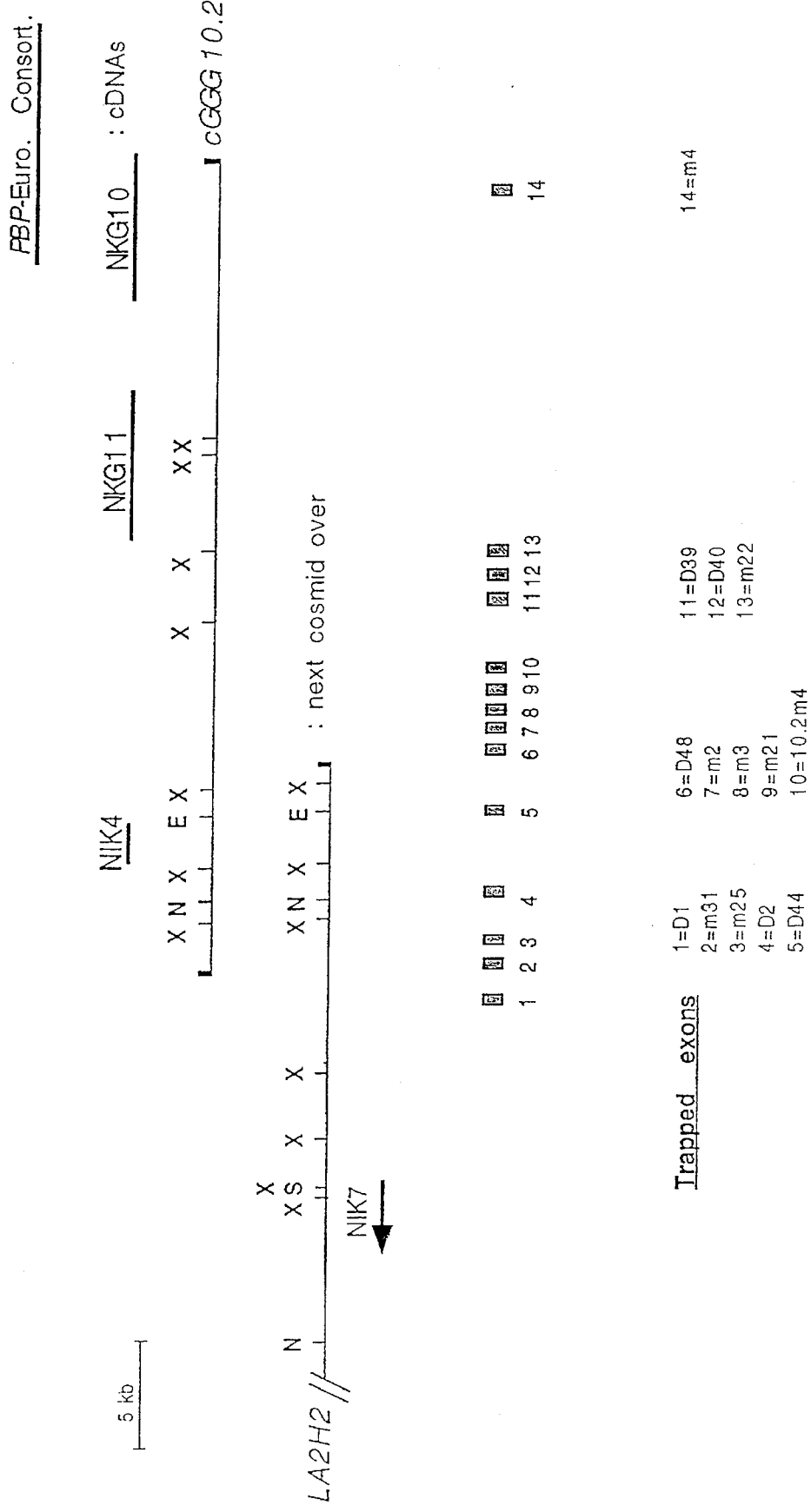
FIG. 6 shows the results of exon trapping within the PKD1 locus.

Trapped exons from the PKD1 locus are shown in FIG. 6 (bottom). The trapped exons were subjected to automated DNA sequencing as above, allowing their alignment with the genomic PKD1 DNA.

Example 3: Diagnostic Test for PKD1 Mutations

Whole blood samples collected in high glucose ACD VacutainersTM (yellow top) were centrifuged and the buffy coat collected. The white cells were lysed with two washes of a 10:1 (v/v) mixture of 14 mM $NH_4Cl$ and 1 mM $NaHCO_3$, their nuclei were resuspended in nuclei-lysis buffer (10 mM Tris, pH 8.0, 0.4M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.)

0.2–1 μg of DNA (in 1–2 μl) was then added to a PCR reaction mixture containing the following components:

| | |
|---|---|
| 10X Taq buffer | 8 μl |
| dNTPS (2 mM each) | 7 μl |
| Forward primer (100 μM) | 1.5 μl |
| Reverse primer (100 μM) | 1.5 μl |
| Blocking oligo (2 mM) | 1.5 μl |
| Taq DNA polymerase | 1 μl |
| water | to 80 μl |

Thirty cycles of amplification are then performed, using a standard DNA thermal cycler the following protocol for each cycle: 94° C., 30 seconds; 55° C., 30 seconds; and 72° C., 30 seconds. It will be understood that the enzymes and nucleotides used in the above reactions may be obtained from any manufacturer, such as GIBCO-BRL, Promega, New England Biolabs, and the like.

The forward primer used in the reaction described above comprises an oligonucleotide that hybridizes to both authentic and PKD1-specific sequences. An example of such a primer is: 5'-CAGGACCTGTCCCAGGCAT-3' SEQ. ID. NO. 4. The reverse primer comprises a sequence derived from a 3' region of the authentic PKD1 gene, which may or may not be present in the PKD1 homologues. Examples of suitable reverse primers are: 5'-CTGGCGGGCGAGGAGAT-3' SEQ. ID. NO. 5, 5'-CTTTGACAAGCACATCT-3' SEQ. ID. NO. 6, and 5'-CAACTGGCTGGACAACA-3' SEQ. ID. NO. 7.

The blocking oligonucleotide comprises: 5'-AGGACCTGTCCAGGCATC-3' SEQ. ID. NO. 8. Importantly, this oligonucleotide must be incapable of supporting polymerization. One example is an oligonucleotide in which the 3' terminal nucleotide comprises a dideoxynucleotide. It will be understood that any modification that achieves this effect may be used in practicing the invention. Under appropriate conditions, the blocking oligonucleotide hybridizes efficiently to PKD1 homologues but inefficiently to the authentic PKD1 sequence. Thus, the amplification products in this diagnostic test are derived only from the authentic PKD1 gene.

The RT-PCR products obtained above are analyzed for the presence of specific PKD1 mutations as follows:

8 μl of the amplified prepared as describe above are added to 50 μl of a denaturing solution (0.5 mM NaOH, 2.0M NACl, 25 mM EDTA) and spotted onto nylon membrane filters (INC Biotrans). The DNA is then fixed to the membranes by baking the filters at 80° C. for 15 minutes under vacuum.

Oligonucleotides that detect PKD1 mutations are chemically synthesized using an automated synthesizer and radio-labelled with $^{32}P$ with polynucleotide kinase, using methods that are standard in the art.

Hybridizations are carried out in plastic bags containing the filters prepared as in Example 1D above, to which one or more labelled oligonucleotides are added in a hybridization buffer (3.0M Tetramethylammonium chloride (TMAC), 0.6% SDS, 1 mM EDTA, 10 mM sodium phosphate pH 6.8, 5X Denhardt's Solution, and 40 μg/ml yeast RNA). Oligonucleotide concentrations in the pools rouge from 0.03 to 0.15 pmol/ml hybridization solution.

Hybridizations are allowed to proceed overnight at 52° C., with agitation. The membranes are then removed from the bags and washed for 20 min at room temperature with wash buffer (3.0M TMAC, 0.6% SDS, 1 mM EDTA, 10 mM sodium phosphate pH 6.8), followed by a second wash in the same buffer for 20 min at 52° C. The membranes are then dried and exposed to Kodak X-OMAT film.

What is claimed:

1. Isolated nucleic acid comprising the sequence set forth in SEQ ID NO:1 or its complement.

2. Isolated nucleic acid according to claim 1 wherein said nucleic acid is RNA.

3. Isolated nucleic acid comprising an intronless sequence derived from the sequence of claim 1 wherein said nucleic acid is cDNA.

4. A recombinant cloning vector comprising the nucleic acid of claim 3.

5. The vector of claim 4 further comprising a transcriptional regulatory element operably linked to said nucleic acid, said element having the ability to direct the expression of genes of prokaryotic or eukaryotic cells and their viruses or combinations thereof.

6. A cell comprising the vector of claim 5.

7. A method for producing a recombinant protein, said method comprising:

(a) culturing the cell of claim 6 in a medium and under conditions suitable for expression of said protein, and (b) isolating said expressed protein.

8. An isolated nucleic acid comprising the sequence set forth in SEQ ID NO:2.

9. An isolated nucleic acid comprising 5'AGGACCTGTCCAGGCATC-3' SEQ ID NO:8.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 31571 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: PKD1 GENOMIC ( x i ) SEQUENCE DESCRIPTION: SEQ ID NO:1:

```
CAGACTCTTT    TCCCATTTAA    CACCTTTTGC    CTTAGGTTTA    TTTTCTGGT    ATCAATACTG        60

GCACACTTAC    TTTGTTTGCA    GTTCCTGTC    TTTTTTTTT    TTTTTTTTT    TTTGAGACA        120
```

```
GAGTCTCACT CTGTCACCCA GGCTGGAGTG AAGTGGCGGG ATCTCGGCTC ACTGCAACCT    180
CTACCTCCTG GGTTCATGCG ATTCTCCTGC CTCAGCTTCC CGAATAGCTG AGACCACAAC    240
TGTGTGCCAC CATGCCCAGC CAATTTTGT ATTTTAGTA GACACGGGGT TTCACCATAC      300
TGGCCAGGAT GGCTCAATCT CTTGACCTCG TGATCCACCT GCCTCCGCCT CCCAAAGTGC    360
TGGGATTACA GGCATGAGCC ACTGTGCCTG GCCTTTTTT TTCTTTTTGA GATGGAGTCT     420
CACTCTGTCA CCCAGGCTGG AGTGCAGTGG GGTAACCTCA GGTCACTGCG ACCTCCGCCT    480
CCCGGGTTCC AGTGATTCTC CTGCCTCAGC CTCCCGAGTA GCTGGGATTA CAGGCACCCA    540
CCACCATGCC TGGCTAATTT TTGTATTTTT AGTAGAGACG GGGTTTGCC ACGTTGGCCA     600
GGTTGGTCTC GAACTCTTGG CCTCATGTGA CCCGCCTGCC TTGGCCTCCC AAAGTGCTGG    660
GATTACAGGT GTGAGCCACT GTGGCCTGGC CTGGCTTTCT TGTTTCTTTT CTCCTCTTCT    720
AGTTTCCCCC TTTTAGGCTA ACAATTATTC ACTGTTAATA AAACCCTCA GGTCTGTATT     780
TTATCAAGAA ACATTTCCCT CACGTCTTCT TCCCTGAACC AAACAAGATC TCTGGCACAT    840
TTTATTTGCT CTGTCTCACC ACATGGATTT TGTTTTTTG TTTCTTTGTT TTTTGAGATG     900
GAGTCTCACT CTTGTTGCCC AGGCTGGAGT GCCATGGCAC AATCTCAGCT CACTGCAACC    960
TCCACCTCCT GGGTTCAAGC GATTCTCCTG TCTCAGCCTC CTGAGTAGCT GGGATTACAG   1020
GCGCGTGGCA CCACCCCCAG CTAATTTTTG TATTTTTAGT AGAGACGGGG TTTCACCATG   1080
TTGGTCAGGC TGGTCTCGAA CTCCTGACCT TGTGATCTGC CCACCTTGGC CTCCCAAAGT   1140
GCTGGGATTA CAGGCATGAG CCACCACGCC CGGCCCCAT GGTTTTCAA ATAGTTTAGA     1200
ATTTCATTTC CAGGTAACTA ATTTGCTTCT TTAAACATAT GTCTTTTCTA TTTAAGAAAT   1260
CCTTTCTAAA CAATTGCATT TTATTCCACA ACCGCCTTCA ACAATCATT GAGACTTGGT    1320
TAATCTGTTT TGCTCATTTG GCAGCAGTTT CTTGTGGCTG TTTCTTCCCT CCACTGGAGT   1380
CCTTGAATCT TAAGTCTGTC ATTTGACTGC AATTAAAAGC TGGGTTTGGA ATACAATCGC   1440
AGCCTTACCA TCCACCTGCT GTGTGACCTG GTAAATTTCT TTTTTTTTT TTGAGACGGA    1500
GTCTTGCTCT GTTGCCCAGG CTGGAGTGCA GTGGCACAAC CTCTGCCTCC CAGGTTCAAG   1560
CGATTCTACT GCCTCAGGCT CCCTAGTAGC TGGGATTATA GGTGCCTGCC ACCATGCCCA   1620
GCTGATTTTT GTATTTTAG TAGAGATGAG GTTTCACCAT GTTGGCTAGG CTGGTCTCGA    1680
ACTTCTGATC TTGTGATCTG CCCGCCTCGG CCTCCCAAAG TGCTGGGATT ACAGGCATGA   1740
GCCACCACTC CCAGCCAGTT CTTTTTTTCT TTTTTCCATT TTTTTTTTT TCGAGACAGG    1800
ATCTTACTCT TTTGCCCAGG CGGGAGTGCA GTGGCACAAT CACGGCTCAG CGCAGCCACT   1860
GCCTACTGGG CTCACACGCT CCTCCGGCCT CAGCCTCTCG AGTACCTGGG ACTACAAGCG   1920
TGAGCCAGTT TGGCTAATTT TGGCTAATTT TTGTAGAAAC GGGGTCTCGC CATGTTGGCC   1980
AGGCTGGTCT CCAACTCCTG GACTCAAGGG ATCCAGCACG CACCCAAGGA GACACTGTCC   2040
CGGCGAGGAG CCTGGAGCCT GGGAAATACA AGGCATCAGA CTGGTCCCAA GACTCTCCCC   2100
AGCGCTGGGG ACAACTGTCT GCTTATCTTA GTCCCCTCCG CCCTTTTCAA TCCAACCCTG   2160
GGTCCTGGGC ACCTCATAGT TCCAAACCCC TGCTATGCAC ATCCCGGCTG TGATGCCTGG   2220
GACAGGTCGT GTCACCTCTC CAAACCTGTT TCCTCATCTG TGAAATGCAA ATCTCCACGG   2280
TCCCTATGCC TCGGATGGTC AGAGTCAGGA TTCCGCATGA CGACCCCAA CAGGAGCCTG    2340
GCACAGACCT GGCTCTGGGC AGCGTCTCCA TAAAGGCCAC CTGTTGTTTT TATCTCCCGA   2400
AAGCGAACAT GACAAGGCTT TAACCCCCCA CGGCAATCCC CCTCACCCC TGTTCTCAGG    2460
ATAGCCTTGG AACCCAATAG CAGAGCGCCT GAGGCCCTTC ATGACCCCAG CCCACCCGCG   2520
```

```
AGCCCACCTC CCACCCTGCC CCTACCCCTC ACACCTCCCG TGGCCAGCCT CCAGCCTCAC    2580
GGTCTTTGCT CACACCGTTC ACCCCCTTC  TTCTGGACCC ACCTCATCGC CCCTTCCTAA    2640
GCATCAGCCC AATTCTTGCA CATCCATCAA ATCCTTTTCC AGACACCTCC TGGAACTCTT    2700
CCCTGCCGCC CCCTACAGCC ATCCCACCT  CTCCGGGTAC CCCGCAGCCC CAGGCCGCAT    2760
CCCAATTCCT CTCCAATTAG CGACTGTTTG TCCTCCCAGC TGAGCGCGGC CTCCGCGCCC    2820
GCCCCCGCTG GCGTCTGCAG AGCCCCGGG  TGGGACGTCT GTCTCCAGAC CCGGGGTTTT    2880
TCGGCTCCCC GGGGCCGTGC CAACCGCGGC TCCAGGCGTT CCTTATTTAG CAGGGCCGCC    2940
GTGCCGCGCC GGAGCCTCGC CCTGGGAGCG TCCTGGCCCG CGTCCTGCTT CCCGTCCCGG    3000
GCCAGGGAAC CCGCCCACGC CCGCCCGTCC CGCGGCCTCT CCCGGGTGCC GCTGGGCCCG    3060
CTACTCACAG CGCTGTGGCG TCCGCGGGGA TGCGCAGCGC GGGACCGAGC GTCCGCAGCC    3120
CGCGGCCCGA GCAGTTGACG CGGCAGGCGG AGCGCCGGGC GCTGGGCCGC AGAGGCAGGG    3180
GGGCTCGCAG GGCCCGCAGC CGCGCCCGGG GCCCCCGCC  AGCGCCCCGA GCCACAGGCC    3240
CAGGCCCAGG GCCAGCGCCA GGCGGGCGGG CGCGGCGGGC GGCATCGTTA GGGCAGCGCG    3300
CGCATGGCCC CGCCGTCCCC AGGTCCGCC  CGCGTGCGGA GGCCGCAGCT CAGGCGGGGC    3360
CCGCGGACGG CATGGCGGGC GCGGGCTGGA TGGGGCTGCG GCCGCGACCT GCTGCTGAGC    3420
GACGCCCGCT CGGGGCTCGG GGCCAGGCCG CTCCGGGAGC TCGGCCGCCC GCTCGGACGC    3480
TGGCGCTGCA GTGCGGGCCC CGCCGCGGCT CCTCCTCCTC CTCCCCGCGC GGCGCGGGCG    3540
GACGGGGCGA GGGGGGGCGG GGCGGGTGCA GGCTCCGCCC CCTTCGCCAC AGCGCGACCG    3600
GGCCAGCGAT GAGGGACTGG CATCCGGAGG CTTCACCCTC CGCTCCACAG GGTCGGCAGC    3660
AGGGCGGGGC CTCCGGAAGC TCCGCCCCAC GCGTTCCCGG GGCGCATGCG ACGTGGGGCG    3720
GAGCGTCTGG AAGCACCGCC GTCGCACTGC AGAGTCGGCC GAGGAGCACG AGCTATTTTT    3780
CACGCTCCGC CCCGCTGCAG GCTAAAGTGC GTGGGCGGGA AGCGGTGGGC AGGGTGCCAT    3840
CTGCTCCGCC CTTCTCCTGT GGTGTGGGCC AGGCGGCGGG TTCCTCCTCC TGCAGCAGCC    3900
ACAGGCTCCA CCCTGATCCT TCTTCCGCGG TTGTGGATCC CTGGGGACG  TGGCACATCC    3960
CCAGGCTTGC TAAACATTGG GTGGGTTCTG GCATTTGGTT TTGTAACGTT TCTGGGTCAC    4020
TCCCGCCTGT GGCCACCCTT CCTTAGGGGA GCCGTGTGTC CTTGGGGCTT TGCTGGGTGG    4080
TCTCGAGGGT GGGAGAAGAA TGGGTTCTCC TGGACCAATG GAGCCCGTGC CCTCGGGGC    4140
CACATTGCTC CTGCGCTCCC TGACTGCGGA CGCGTGTGTC TCGCGGCTGT CTCTGTGGAG    4200
ATGGCCTCCT CCTGCCTGGC AACAGCACCC ACAGAATTGC ATCAGACCTA CCCCACCCGT    4260
TGTTTGTGAT GCTGTAGCTG AGGGCTCCTC TGTCTGCCAG GCCGGTCACT GGGGACTCTG    4320
TCCAGGGCCT GGTGGTTCCT GCTTCCCAGC ACCTGATGGT GTCCATGAGA GCAGCCCCTC    4380
AGGAGCTGTC CGGGAGAGAA GGGCGCTGGT GGCTGCTGAG CGGAGAGCAA GGCCCGTGTT    4440
CTCCAGGCCC TTGGCACAGC AGTGGAGCCC CCGCCCTGC  CTTGTGTTGT CCTCTTAGGC    4500
TCTGGTCCTG GGGTTTGGAG GAGGGGACC  CTGGGAGTTG GTGGCCTGTC CAGCCTGAG    4560
CTGGCAAGAT TCCGAATGCC AGGCCCCCA  AGTGTGCAAC AGGGCACAGG GTGACCTCAT    4620
GTGGGCAGGT GGGTGCTGTT CTGTACACAC CTGGGGCCGC CGCTGGGAGA GTTCTGGAAG    4680
GTGGGGTGAG GGGACCCATG GCAAACTAGG GCCTTAGGAA GGATGTGAAG GCCCTGGCTG    4740
GCCCCCCAGG CCACCCTCTG TGCTGTGGGG CAGCCCAGCC ATTTTGCTGT CTACCCTGCA    4800
AACTCCTCCT CGGGGAGACG GCTGGGTTTT CCCCAGGGAA GAGGGGTCAA GCTGGGAGAG    4860
GTGAAGGACA CAGATCACAG CTGCTGGCAG GTGTTCAAGG GTCCAAGAGC GTTGCTGTCT    4920
```

```
GGGTGTCACC AGTAGCCTTC CTGGGGGGCT CACGCAGGTG CCTCTCCACT TGTGGCTCCC    4980
TGGCTGCTGA AGCTCAGCAG GGACAGCTGT GTCCAGTTCC AGGTGGAGGA CAGCCGGGGC    5040
TTCTGAGGCC ACAGCCTGCC TTGGGTTAAT GATGCTGCCG AGAGGTGGTG GCTTTTGGAA    5100
AAGATGGCGT ACTGCAAAAC GTGCTGCTCT GCGTGGCTCG AAGCTTCGTG GGGAGACGTG    5160
GGCAGAGCCG TGGCTGACTC ACAGACCCCC CACCCAGAG CCTGCCCTGC CCTCCCTGCC    5220
CCGACCCTTC TCCCTCCTGA CCCATGTGTT TTTTTTTTT TTTTTTTTT TTGAGACAGA     5280
GTTCACTCTT GTTGCCAAGG CTGGAGTGCA ATGGCACGAT CTCGGCTCAT GGCAACCTCC    5340
GCCTCCTGGG TTCAAGCGCT TTTTCCTGCC TCAGCCTCCC GAGTAGCTGG GATTACAGGC    5400
GTGCACCACC ATGCCTGGCT AATTTGTAT TTTAGTAGA GACAGGGTTT CTCCATATTG      5460
GTCAGGCTGG TCTTGAACTC CTGACCTCAG ATGATCCGCC CGCCTCGGCC TCCCAAAGTG    5520
CTGGGATTAC AGGCATGAGC CACCACGCCC AGCCTGACC CATGTTTTGA ACCAAATTCC     5580
AGCCACCCTT TTATCTGCAA GCATTTGGA GGGCATCGCA ATACTGCAGA CCCACCTAAC     5640
ACAACAGACA GTTCCTTCAT GCCACCGAAG GCCTGGTGTG TTCACATTTT TGGTTTAATA    5700
GTTGAATTA AGAGCCAAAT AAGGTCCACA CACTGCAATT AGTTGATGTC TTTTTTTTTT    5760
TCTTTTTTTT TTTTTTTTG AGACGGAGTC TTGCTCTTGT CTCCAGGCCG CAGTGCAGTG    5820
GCATGATCTC AGCTCACCGC AACCTCCGAC TCCCTGGTTC AAGCGATTCT CCTGCCTCAG    5880
CCTCCCGAGT ACCTGGTAGC TGGGTTTACA GGCATGCACC ACCGTGCCCA GCTAATTTTT    5940
GTATTTTTAG TAGAGACGGG GTTTTACTGT GTTGGCCAGG ATGGTCTCGA TCTCCTGACC    6000
TCGTGATCTG CCCACCTCGG CCTCCCAAAG TGCTGGGATT ACAGGCGTGA GCCACCGCAC    6060
CCGGCCAATG TCTTTTAAAA ATATATACTT TTTTTTTTT TTGAGACGG AGTTTCGCTC      6120
TTGTTGCCCA GGCTGGAGTG CAGTGGCGCG ATCTCACCTC ACGGCAACCT CCGCCTCCCG    6180
GGTTCAAGTG ATTCTCCTGC CTCAGCCTCT CCAGTAGCTG GGATTACAGG CATGTGCCAC    6240
CATGCCTGGC TAATTTTGTA TTTTTAGGAG AGACGGGGTT CTCCACGTT GGTCAGGCTG     6300
GTCTCAAACT CCTGACCTCA GGTGATCCGC CTGCCTTGGC CTCCCAAAGT GTTGGGATTA    6360
CAGGTGTGAG CCAACGCGCC CAGACAAAAA TATATGTGTG TCTTTAAGGC TGGTCAAGCA    6420
AAGCAGTAGG ACTGGAGAAA GAATGAAGAA TTCTACCTGG CTGTGATCAA TTCGTTGTGA    6480
ACACCACTGT GCTTGGACCA GCTAGCTGAT GTCTTTTGTT TTGTTTTGTT TGAGACGGAG    6540
TCTGGCTCTG TCACCCAGGC TGGAGGACAA TGGTGTGATC TCGGCTCACT GCAGCCTCCA    6600
TCTCCCGGGT TCAAGCGATT CTCCTGCCTC AGCCTCCTGA GTAGCTGGGA TTAGAGGCGC    6660
GCGCCACCAC GCCCGGCTAA TTTTAAAAA TATTTTAGT AGAGATGGGG TTTCACCATG      6720
TTGGTCAGGC TGGTCTTGAA CTCTTGGCCT TAGGTGATCT GCTTGCCTCG GCCTCCCAAA    6780
GTGCTGGGAT TACAGGTGTG AGTGATGTAT TTATTTATT TATTTATTTA TTTATTTTA     6840
TTATTTGAGA TGGAGTCTCA CTCTGTTGCC CAGGCTGGAG TGCAGCAGTG CCATCTCAGC    6900
TCACTGCAAG CTCCGCCTCC TGGGTTCACG CCATTCTCCT GCCTCAGCCT CCTGAGTAGC    6960
CTGGACTGGT GCCCGCCACC ATGCCCAGCT AATTTTTTGT ATTTTAGTA GAGACGGGGT     7020
TTCACCGTGT TAGCCAGGAT GGTCTGGATC TCCTGACCTC GTGATCCTCC CGCCTCAGCC    7080
TCCCAAAGTG CTGGGATTAC AGGCTTGAGC CACCGCCTGT CTTTTAAATG TCCGATGATG    7140
TCTAGGAGCT TCCCTTCCTC TCTTTTTCCT TGTGCAATTT GTTGAAGAAA CTGGCTCCTG    7200
CAGCCTGGAT TTCTCGCTGT GTCTTGGGGG TGCCACCTCC ATGGTGTCAC CTCCGTGGTG    7260
CTGTGAGTGT GTGCTTTGTG TTTCTTGTAA ATTGGTCGTT GGAGCCGACA TCCCATTGTC    7320
```

-continued

```
CCAGAGGTTG  TCCTGGCTGG  CACTGGCCTA  GGTGTAGATG  TCATCAGCTC  AGGGCCCCCT   7380
GCTCTAAAGG  CCACTTCTGG  TGCTGGTTGC  CACTCACCCT  GGCTGGGGGT  CACCTGGGTC   7440
TGCTGCTGTC  TCGCAAATGC  TGGGGTCCAG  GACTGGGCAC  ATCGAGGGAC  TTGGTAGGTG   7500
CTTGGTTCAC  TGATGTAAAA  TATAGGAGCA  CCCGGGGCCT  TGCCCTTTCC  CACCTGCATC   7560
CCTGAATGAC  AGGAGAGTGT  GGGAGAGTGT  AGGGACAGCA  GGCGCAGACC  CCGGGGCCCC   7620
TGCCTGGGAT  TGGCGTCGGG  GAAGACAGGC  ATTCTGGAGC  GACCCCTAGG  CCTGATGCCT   7680
TAGAGCGCAA  CTGCCAGAGA  CACAGCTTCC  TTGGGGGCT   GGCCAGGCCA  CGGAGGGGCC   7740
CTGGCTCCCA  TTTCTGGTCC  CTGGATCCTG  AGAGCGAGGA  CTAGGGATTG  TCACCAAGGC   7800
CTCCATGAGC  CCTCAGCAGA  AGGAGGGCCA  CCCTCGAGGG  CTCCGTTATC  ACTGGAGCCC   7860
GCGTTCAACC  AACACGCAGA  TGATTCTCCA  AGGACAGAGA  TGGATGATGG  GGAGGGGCT    7920
GGCCTGGAAG  GACCCCCAGT  GCAGGTGACA  TTGAAGCCAG  GTTTCAAAGC  TCCCACAGGG   7980
AGCTGCCCAG  AGAGAGTCCC  CAAGGGGCAA  GGTGACTCGG  GGGCAGGGGT  AGGGCCTCTG   8040
TCAGGAGAGC  CTAGGAGAGG  CCTGTGTCTT  CTAGGAAGAG  CCCTGGCAGC  CGAGCGGAGG   8100
CAGTGGTGAG  GACCTGCATC  CTGCATGTCC  AGCTGGCCTC  ACCCGGGGTC  CCTGAGCCGG   8160
GTCTTACGTG  GCTCCCGCAC  TCGGGCGTTC  AGAACGTGCC  TGCGTGAGAA  ACGGTAGTTT   8220
CTTTATTAGA  CGCGGATGCA  AACTCGCCAA  ACTTGTGGAC  AAAAATGTGG  ACAAGAAGTC   8280
ACACGCTCAC  TCCTGTACGC  GATTGCCGGC  AGGGGTGGGG  GAAGGGATGG  GGAGGCTTTG   8340
GTTGTGTCTG  CAGCAGTTGG  GAATGTGGGG  CACCCGAGCT  CCCACTGCAG  AGGCGACTGT   8400
GGAGACAGAG  AGCACCTGCA  GGTCATCCAT  GCAGTATCGG  CTTGCATCCA  GATCATACAG   8460
GGAACACTAT  GATTCAACAA  CAGACAGGGA  CCCCGTTTAA  ACATGGACAA  GGGGTCACTC   8520
ACGCCTGGAA  TCCAGCAGT   TTGGGAGGCC  AGGGTGGGTG  GATCGCTTGA  GCCAGGAGT    8580
TTGACACCAG  CCTGGGCAAC  AGGGTGAGAC  CCCGGTCTCT  AAAAAATAAA  AGAACATTGG   8640
CCGGGCGTGG  TGGTATGCAT  CTGTGGTCCC  AGCTATTCAG  GAGACTGAGG  TGGGACATCA   8700
CTTGAGCCGA  GGAGGTCAAG  GCTGCAGTGA  GCTGTGATCA  CACCACTGCA  CTCCAGGCTG   8760
GGTCACAGAG  CAAGACCCTG  TCTCAAAAAA  AAAAAAAAAA  AAAAAAAAA   ATCACAGGAT   8820
CTGAACAGAG  ATTTCTCCAA  AGAAGACGCA  CAGATGGCCA  ACAGCGTGTG  AGAAGATGGT   8880
CGGCCTCATT  AGTCATGAGG  GAAACGTAAA  TCAAACCAC   TGTCCAGCCG  GGCGCGGTGC   8940
CTCACGCCTG  TAATCCCAGC  ACTTTAGGAG  AGCAGATGGC  TTGAGGCCAG  GAGTTTGAGG   9000
CCAGCCTGGG  CAACATAGCG  AGACCAATAA  ATAGATATTA  GTGGTGGCGC  CTGTAGTCCC   9060
AGCTAGTTGG  GAGGCTGAGG  GGGGAGGATT  CCCTGAGTCT  ATGAGGTTGA  GACTGCAGTT   9120
AGCTGTGATG  GTGCCACTGC  ACTCCAGCCT  GGGCGACTAG  GAAACGGTCT  TTAAAAAAA    9180
AAAAAAAAA   CAGGGTGGGC  GCGGTGGTTC  ACGCCTGTAA  TCTCAGCACT  TTGGGAGGCC   9240
AAGGTGGGGG  GATCACAAGG  TCAGGAGTTT  GTGACCAGCC  TGACCAACAT  GGTGAAACCC   9300
CGTTCTACTA  AAAATACAAA  AATTAGCGAG  GTGTGGTCGT  GGGCGCCTGT  AATCCCAGCT   9360
AATTAGGAGG  CTGAGGCAGG  AGAATCACTT  GAACCCGGGA  GGCGGAGGTT  GCAGTGAGCC   9420
AATATCACAC  CACTGCACTC  TAGCCTGGTC  AACAGAGCGA  GACTCTGTCT  CAAAAAAAA    9480
AAATGCTGAG  CGTGGTGGCG  CATGCCTGTA  GTCTCAGCTA  CTTTGGGGGC  TGAGGCAGGA   9540
GAATCGCTTG  AACCTGGGAG  GCAGAGGTCG  CAGTGAGGCA  AGATTGCACC  ATTGCACTCC   9600
AGCCTGGGAG  ACAGAGTGAA  ACTCTGTCTC  AAAAGAAAA   GGTCTAGGAA  GAGTCCGCAC   9660
CCTCTCCCCG  CGGTGGCCAC  GCCGGGCTCC  GCGCTGAGCC  CTCTGTGTTC  TTGTCTCTCC   9720
```

| | | | | | |
|---|---|---|---|---|---|
| ATACCTCATC | ACGGCACCGC | AGGGTTGCAG | CCACTCCTGG | TCTCATTTTA | CACACCAGGA | 9780 |
| AATTGAGGCT | CTTTGAGAAG | CCGTGGTGAT | GATTTCATCA | GCATGCTCTG | GGGCAGACCC | 9840 |
| CTGCAGCCGC | ACAGGGTGCC | TGGGGCCCAC | ACTAGTGCCC | TGGTTTATAG | ACAGACAGAG | 9900 |
| GTGGCAGTGG | CGCTTCCGAG | TCGGGCTGCG | ATGTGCTTGC | ACTCCCGAG | GGGCTGAGGG | 9960 |
| GCCCTGCGCC | CAGGTGCAGC | TGCTTGGGTG | CTGCCAGCCC | CTCCCACCTC | TCCCTCCCTG | 10020 |
| CCAGCCCCTC | CCACCTCTCC | CTCCCTGCCA | GCCCTCCCA | CCTCTCCCTC | CCTGCCAGCC | 10080 |
| CCTCCCACCT | CTCCCTCCCT | GCCAGCCCCT | CCCACCTCTC | CCTCCCTGCC | AGCCCCTCCC | 10140 |
| ACCTCTCCCT | CCCTGCCAGC | CCCTCCCACC | TCTCCCTCCC | TGCCAGCCCC | TCCCACCTCT | 10200 |
| CCCTCCCTCC | AGCCCCTCCC | ACCTCTCCCT | CCCTGCCAGC | CCCTCCCACC | TCTCCCTCCC | 10260 |
| TGCCAGCCCC | TCCCACCTCT | CCCTCCCTGC | AGCCCCTCC | CACCTCTCCC | TCCCTGCCAG | 10320 |
| CCCCTCCCAC | CTCTCCCTCC | CTGCCAGCCC | CTCCCACCTC | TCCCTCCCTG | CCAGCCCCTC | 10380 |
| CCACCTCTCC | CTCCCTGGCT | CATCCCTGCT | GTGTCCCTTC | TCTCTAGTTT | CCTGTTCAGT | 10440 |
| TTCAGGAAGG | AGGCTGGGAA | CCCAGATGTA | GGGAATTTGC | GCCCTGGAGT | CAGACCTGGG | 10500 |
| TTCACGTCCC | AGCGCCTCCA | CCTCTGGTGT | GACCTTGGTC | CAGTCTCTCA | GCCTCAGTTT | 10560 |
| CCTCACCTGT | AAAGTGGGCT | CCATGATTAG | ATGCACCCTG | CAGGGCAGTG | TAGCAGTGAC | 10620 |
| CTGGCTCAGC | CACTGGCAGC | CCCAACAATC | ATACCTTGTT | AAAGTAGCTC | TGTCGGTTCC | 10680 |
| CTCAGGGGTT | CCGGGGCCC | ATTCCCTGT | CCTCCATGCA | CTGTGAGACC | TGCCCTGCCA | 10740 |
| CAGAGCAGAG | TGTAACAGCC | TGAGGGTGAG | AGCCAGACAC | TGTGCCTGTG | CTTAGACCAG | 10800 |
| ACACTGGACG | ACGGGAGCCA | GTGCAGCCTG | GGCGGGTGGA | CTCCTATGGA | CCCCTCAGCA | 10860 |
| CCCAGCCTCG | GTGCCTTCAG | CGCAGGGCCG | CGTGGCTGTG | GGGCTCACA | AGACCCGGCC | 10920 |
| CACTCCTGCT | TGTGCCTACA | TCTGGGTGTT | TGCCCATTGG | TGCCTTTTGA | CGCGTTCTGG | 10980 |
| TGTGTGTGAG | ACGTGCGGGG | CTGGGAAGTG | TTGGCAGAGC | CGCGAGTACC | GTCCTCACTC | 11040 |
| CTTTTGTTCT | TTTGACGTAA | GCTGGCGAGT | GGCACTGCCT | GAGTTCCGCT | CAGTGCCCGC | 11100 |
| CCTGATGTGC | GGACCCCGCT | GCATTCTTGC | TGTTAGGTGG | TGGCGGTGTG | CGCTGTCGCT | 11160 |
| GGTGGGCACC | GAGAGTCTTT | GGGAGCTTTG | GGGAGGTTGT | GCCAAGCCTG | AGCCTCGACG | 11220 |
| TCCCCCTTCC | CGGCTTTCTG | TTGGCTCTTC | TGAGGCCAGG | GCATCTCTAT | GAGGGCCTCC | 11280 |
| TGCTGGAGCC | GTCTCTGTGG | ATCTCCTCTG | CCATCCTGGC | CCATGAGTGG | GTGATGCGCT | 11340 |
| GGCCACCATC | TGGTGACAGT | GGCCGGGCAC | CGCTGCCAAA | TGTGGGTCCC | GCATCTGCAA | 11400 |
| GCCCCTCCCT | GGGTCCCCTA | GGGTATGGGG | TGGTTCTGCC | ACTGCCCTCG | CTCCCCCACC | 11460 |
| TTGGGGTGCC | TCTCCCCCTG | CTCGTGGGGG | AGACCCTGCC | TGGGATCTGC | TTTCCAGCAA | 11520 |
| GGAATATACT | TTGGAGGGAG | ACACACATGT | TCTTTTCTGG | AGCTCTGCAG | TGGCCACGGC | 11580 |
| AGCCCAGCCC | GCCAAGCACC | CTGGAATGAA | AACATCCCGC | TGCTGTCTGG | GCCTGGCCTG | 11640 |
| CACTCTGCTG | CCTGCGCTCC | AGCTGGCTGA | GGCCGGGCAC | GTCTGCGGGC | ACAGCAGCGG | 11700 |
| GGGCGCCACA | GTCTCCCTGC | AGAGTGAGCG | CAGCTGGAAA | ATGCAGCTCA | CGCCCTTTCC | 11760 |
| CAGAACACCT | CGCTCTTCAT | GGCTTGGCAG | CTGTCCTTGC | CTAGGGCCA | GGGTGCCCAG | 11820 |
| GCACTGGTGG | CAGGAGAAGG | GCTACATCTG | GGCTGAGGC | GGCTGGGTC | CTTTTCTCCC | 11880 |
| TGCAGCTCCC | GAGGCCCAGC | CCTGGCCCAG | CCTGGCATTC | CTGACCTTAG | CAGCGCCATG | 11940 |
| ATCTGAAGAC | AGGCTGGCTT | CTGTGAGGCC | ACCTCAGAAA | GGGCTTTGTG | CCCAGGCAGA | 12000 |
| GGCGGAAGCC | AGCTCTTCCT | TCTGGTTGAG | GCAGGAATGA | GGCCAGCGCT | GGGCAAGCCC | 12060 |
| ATGCCCAGGG | AACGTCACAG | CTGTGGGAGT | ACAGGGGCTC | CGGGTTCTGA | GCCCGTCCAC | 12120 |

```
TGTGCATCGT GGCCCTGGCC TCAGGATGGC TCGTACCATC ATTGGCTGTG CCCACAGCCG    12180
AGTGGGTGAT GGGATTCCGG CTGCCCCGCT GGATCTGTGC TGCTGCCCTC TCCAGGGCAC    12240
TGCTGTGCCC GCACAGCCGG GCGCAGATGG CCAGTTTGCT TGCCCCCCCC CCACCATCC     12300
TCTTCCTACC TTGGCTTCCT CCATTGACAC ACTGGACCCT GCTGGCTGCC CGGGGAGGTG    12360
TTTGGGGGAT GGTGTTGGGG GAGGAGGAGG GCCCCTTGAG CCTCAGTGTG CCCATCAGGA    12420
GCGTAAGGTC AGTGCAGCAC CTGCCCACAC AGGCTGTGAA GGGTGGGAGT GGAGAGGGAT    12480
GCAAGGGGGT CACAACGCCT GGCTCCATGT CAGCTGCGTG CAGGGGCACC AGGAGCCGGC    12540
CCTCATTCTC CCCTTGAACT GGAAGGGTGG CCCCGACCCC AGCGGCAGGT AGCATACGTA    12600
TGAAGCGCTC TCCTTCCTAC ACCCCACAGG TGGGCTCGTC TCCAGACGGC CCTTTTTGAG    12660
CTGGCTGTGT TTTCCATCT GTGTAGGCAA GGACATCGCA GACTCCCCTT TCTCATCTCC     12720
CTCGTTCAGC CTCCGAGGCC GGAGTCTCCA TCCCTGTGCC TGCCTGTGGG TCCCGGGAGG    12780
ACCTGAGGCT GCCCATGTCA CCCCCGGCAT CTCATCCTGG GACAGTTCA GCCGTGGGAG     12840
GGATCTGTAA GGACAGAATG CCGCTGAGCC TGGGGCTCCC CAGCTAGTCT CACACCCCGT    12900
GTCTGGGACC CAGAGACCCT CGTGCAGGGC TCTGTTGCTT GGGGCCTGGC AGCCTCGTCC    12960
TGTATCAGAG GCTGCCACCC CCACCCCTCG TGGGGCCAGG GTTGTGGCCG GCCTCCCTGG    13020
CCCTCCCCAT GGAAGTGGTA GGCGGAGCCA GCAGCCATCT GCCCAGCCCG GGGCTGCACT    13080
GTTTTTTTTC AAATGAGCAC CGTCCCAAAC TGCAGCCCGT TAATTTAAAC AGGATCATTT    13140
CCGGCCCTGG AAGCCGCCTC ACTCTCCTTA AATAGAAAGG AGCACAGCGC AGAGGGAAAC    13200
AGATGAGGTC ATGGCTCGGC TGGCCCAGCG AGGAAGGGGC CGCAGTGGGG GTGGCACTGC    13260
CGCCTGTCCC CTGTCCTCTC CAGCGCCCAC ACTGCAGCCC ATTTCCTCAC CCTGGGCCTG    13320
CTCTCGGGAG GGACGGGCCT GGGGGTCCTC TTGCTGGGCG GAGGGGAACC AGCTCCTCCA    13380
GGAGAGGACG GGGCCTGGCA GGGGGCATGG GGCCTCCCTG GGTCTGGCGT CCTGTCCTGC    13440
CCCTGCCGAG GGAGGAGCGG TTACATAAGC TCCGCAGGCG GCCCCTCCGA GCCGGTCCCC    13500
CCAGCCCAGT TTCCAGTGAG GCGGCCAGCG CGGGCGGGGG TGCCGGGCCT GGCGCACACC    13560
CGCTGCTGAC CACACGTGTC TGGAATGTGC AGATGTTTCT TTGGGGGCTC CGTCCGGCCC    13620
CCAGACCCCA CTCAGCATCT GGTCTGGGGA GTGGGCGCCT GGGGCACTCA GCTCTGAGTG    13680
TGAGACTCTG AGGCAGGTCT GGTTTGTCTG GGGCCATTCC CTCTGCTGTG GATTGGGAGG    13740
GCCCCGGGAG CTGCCCCACA CCCAGGGAAG TTCTCCTCAG TCCCACTGTT GCATTCCCCG    13800
ACCCCGGCTC CCCCGGCCCA GGAGCGCCTG TGGGCAGAA GGCCCAGCCC CAAGACTTCC     13860
CGGCCCTGCC AGCCTCAGGC TTCACCCACC CTCGCGCCAA CTGTGGGCAG AGCCCAGGGG    13920
GAGGGCAGGA GAGCCAGCGC CTGGCTGGGA ACACCCTGAG GGGCCGAGGC TCCAGGGCGA    13980
GGGGGCCCGA CCTGGGGTTC ACACGCCCGG GTGGCGGGCA GACCCGCTGC AGCATGAGAC    14040
ACGTGTCAGC TACCTCGGGC CGGCAGGCTG GCCCTGCTGC CCACAGCCCT GGGACGTGGC    14100
CCCACCTGTG ACGGGTGTGG AGGGGCAGCC TCCAGGCCTG GCCACACCCT CTGCTGTTGC    14160
TGCTCCTGCT CCAGGATTGG CAAGGGTGCT GGGAAGGGGT GAAGACCCGT ACTGTGGCCA    14220
CACACCTGGG ACTTCCTTCT CCACCCAGTG GTGCCCAGC AGCCGCTAAG GAGCCCGCTG     14280
GGTCCACGC TAGGATGGTC CTAACTCCTC CCGCCTTCCA GATCGGACGC TCGGCGCTGG     14340
GGACCCCTTG TGTCCCGGGG CTGGGGCACC GTCCTGCCCC CATGGGGGTG TACTCCTCCC    14400
GACAAGCTTG GCTTCAGCTT CCCTGGGAGC ACATCCTGGC CCTCGGGCAC CCATCAGGCT    14460
GTCCCTGTGC ACCTGGCTCC CACCCTTCCA GCTCATAGCA GGAACTGGGG TGAGGAGTGC    14520
```

```
GTGGGGCAGC AAGGGCCTGG GACCCCAGAG GACCCTGCAC TCTGCTCTGT GCTCTTGCCT    14580
GGGCTTAGGG CCGCTCGGTG GTCCTGCTGC CAGATGCCTG GGCCCTGCTG TGTCCCCCAT    14640
CTTGCAGGGA ACCAGAACGT GGGGGCAGGG CATCAGACAG CGGCGATGAT GTCACCTGGC    14700
GGGTGCAGAG GAAGCCCGAG GGCGGGGTG GGGGCTGGC GCGAGGCTGC CTGGCTAGGC    14760
CTTGGCGTTC CCCAGAACG GCGATGGCAA AAGCAGATGG AGACGTGAAA AAGTACGGGA    14820
GCAAGCGAGG TGAGGACTCC ACGGGACCC CTGTGCTGTT CCCTGTCCCT GAAGCCCACA    14880
CCTGAGTCCT GCCCAGGGCA GATGCTTCCA CACCCAGGGG GCACCTGAGT CCTACCCAGG    14940
GCAGACGCTT CCACACCCTG GGGCTGGGG GACTGCACCT GGCTCCTGTC TGGGCCCCAG    15000
CTTCATTCCA CTGCCCTGGG CCCTGGGAGC TCGGCCGAGC GGGGTCCCC AAGACCTTGC    15060
TGCATTTCTG GGCCTTGGGC TGGGGTGAGG GCCGGGAGAA GGAGCCAGCC TGGAGCCTGG    15120
CACGCAGGGA GTGCATGGCC AGAACGGTG ACAGGCAGGG CTGCCTGCTG GCGTGGAAGA    15180
AGTGTCCATG GCACCCCAG GCCTGGTTCA CAGTGGGATG GGCGGGGAG CCGGGGGGT    15240
CTGGGGTCCT CGGCTGACCT GCCCCACCC CTGCCCTGGC TTGTCAGCTC CCAGCAGCAG    15300
CCACTCTTGA TGGATTTTCC AGAAAATGAG GTGTGGCCAA ACATCTTCAG GCTTTTCCTT    15360
CTTTCCTTTC TCCCGTGGCC TGGGTGGGAG CTGCTCCCCA TGCCTGGGGG CAGGTGCGAG    15420
AGCCTGTGCC CCTCCCTGGG GCAGTTTCAC AGCTGTGTCC CTTCCAGGGG GCCTGCCTGT    15480
GTTCACCGTG GCCTCTGCAG CACCTCTCGC CCCTTAGGGC TCCTGCGCCT CGGGTCCGG    15540
TGCCTCATTT CTCCCTAAAG CATTGGTTCT GCTGCCGCCG CAGCCGCTGG AAAGTCCCTC    15600
CTCAGGTCTA ACTGCAGTTC CTCACGGCAC AGTGTTCCCC CTCGGGCATG GTGCTTGGGC    15660
AGTGGGTGTG AGTCCAGCTG CCTCACCCTG TCTCGAGAAT GGCCTCTTGC TGGTCTCCA    15720
GCCACCACCC TGTCCCACCC CACGGCGGGG ATGGTGTGGA TGCCTAGCAG CGCGGCTGTG    15780
GGCCCACCCA TCCTTATGGG CAGTGGGGAG CACCTCAGCC CGTGTCCCTA CCTTGGTGTA    15840
GAGGAGGGGA CGGCAGAGAA GCAGGGTTCA GTTAGGGGGG AAGTGGTGGC CCTGCCGGAG    15900
GGGCCGTTCC CTGTGTGCCT GGCCCCAGA TCCTCTCCCC TCCCGGAGCC CAGGGCACAG    15960
GCATAGGCTC TCTGAGTGTC CCACAGCCCC TGGGGAAGG GAACTGCACC CCCAACCGTG    16020
CCCTCCATCC GCAGATGGAA CGAGAAGCTC CGGGAGCCAG TGCCCAGCGT CTCATCTGTC    16080
TGGGCACCCA GCCCAGGTGA GGGCCTGGCT CCACCGTCCG TGGCTGGTGC TGCTTCCTGG    16140
CACGGAGAAG GCCTCGGCTG CTCTGTCCCC TCAGCTGGGG TGGCCTCTGG TCCCCTTCTT    16200
TGTTGGTTCC CTTCTCAAGC TCTTGCCCTG GCCCCGGGCC CCACCGGGCA GCCTGTGTGT    16260
GCGTCTCTCC TGCGCCGGGT AGGCTCCTGT GGGAGCGGAG CTCCGGTGGG AGGAGCAGGG    16320
CTGGAGGCTG GCAGGGCTG GCGGGTGTT CAGGGATGGA GGCCGCCCCG GCTTGGGGCT    16380
GGCTGCCGGG TGGTCATTGC TGGGAAGAGC AAGTCTAGGC GGAGGCACCT GCTGGGTCAC    16440
TCGTGGGGAG GGTGACACCT GGGGAAGTAG AGGCCCGTGG CAGGAGGTGA GGCCTCGGGG    16500
TCCTGGGGAG CAGGGGGGTG GTGTGCAGAC CTGCGGAGCC ATAGTCCTGT GCCAGGAGCA    16560
CTACTGGGAG TGCGTGGGAC CAGGAGGGGT GCCCAGGGTG GGCGGCAGAG TGACCCCCGA    16620
GGTGCTTGAG GCCGAGGGGA GGTGGAGTTC TCGGTTTGCC CCAGCTCTCT GTCTACTCAC    16680
CTCCGCATCA CCAGCTCCAG GACCTGGTTT GTAACTCGGG CAGCTCTGAA AAGAGAGACA    16740
TGCTGCCGCC CTGTGGTTTC TGTTGCTTTT TCTTCACTGA CTACTGACAT GGGATGTTTT    16800
TCCTACGGCT GTGACCAATT GTGCTTCTTC TAATTGCCTG GTTTTCTTT TTTGTTTTT    16860
GGAGTTTTCT CTTTCTTTCC TCCCTCCCTC TCACCCTCCA TCCTTTTTTT TTTATTTTT    16920
```

```
ATTTTTTGAG ATGGAGCTTC ACTCTTGCAG GATGGGGTGC TGGAGTGCAG GGGTGCGATC    16980
TCAGCTCACT GCAACCTCTG CCTCGCGGGT TCAAGTGATT CTCCTGCCTA AGCCTCCTGA    17040
GTAGCTGGAA TTACAGGTGC TTGCCACCAC GCCCGACTAA TTCTGTAGTT TTTAGTAGAG    17100
GAGGGTTTCA CCCTGTTGGC CAGGATGGTC TCGATCTCTT GATCTCATGA TCCACCCACC    17160
TTGGCCTCCC AAAGTTCTGG CATTACAGGA GTGAGCCACC GTGCCCGGCC ATCTTTCTTT    17220
CCTTGCTTTC TCTTTGTTTT CTTTCGAGAC CGGGTCTTGC TCTGTCGCCC AGGCTGGACT    17280
GCAGTGGCAC AATCATAGCT CACTGCAGCC TCGACTTCCC TGGCTCAAGC GATCCTTCCT    17340
CCTCAGCCCC CCGAGTAGCT GGAACTACAG TTACACACTA CCATGCCTGG CTGATTCTTT    17400
TTTTCCTTGT AGAGATGGGG TCTTGCTATG CTGTCCATCC TGGTCTCAAA CTCCTGGCCT    17460
TCCCAAAGCA CTGGGTTTAC AGGCATAAGC CACCACACCC AGTTTCCTTT TCTTCTTTTT    17520
AACTGGAATA GTTGACGTTT TCTTTATTAG CTGTGTGTCA GGAGGGTATT TTTGGCCTTT    17580
AGTATGTCGT GTAAGTTGCT AGTGCTTTC TGAGATTGTA GTTTGTTTTC TAATTTTATT      17640
TATATTTTGC GTAGAAGTTG TGTATTTTAG ATGGAGTTAG GTCGGCTGGT CTTTGATGTT    17700
TTATTTATTA ATTATGTATG TATTTATTTA TTTTTGAGGT AGAGTCTCGC CGTTTCACCC    17760
AGGCTGGAGT ACAGTGATGC GATCTCAGCT CCCTGTAGCC TTGACCTCTC TGGGCTCAAG    17820
TGATTTTTCT CTCCTCTACC TCCCGAGTAC TTGGGACCCC AGGCGCATGC CGCCATGCCT    17880
GGCTAATGTG TATTTTTTGT AGATACGGGG TCTCACTGTG TTGCCCAGGG TGGTTTCAAA    17940
ATCCTGGGCC CAGGCGATCC TTCCGTCTCA GCTCCCACGG TGCTGTGTTA CCGGCGTGTG    18000
CCCAGTGCCT GGCCGTCTTG GAGGTCTTGT TTCTCTGGGT TTATGCCTCG AGTCTGTGTG    18060
GGGGCTGTGG ACAGGGTTGG GAGACCTTGG CTCTGTGGGG GACTGTGGAC AGGGGATGGG    18120
GGGCCTTGGC CCTGCGTGGG ATGGGTTGGG GGTCCGTGCC CTTCCTGGCC CTGGGTGGAC    18180
AGGTCCATGT GGCACTCGGC ATAGGGCTGA GATGGGTGCA GAGGGCTGAG GCCCCAGGC     18240
CTCTCCTGGC TTGGTTTCCC CAGATGAGTG TTCATTTGGG TCTTCCATCA GAAAGTCCCC    18300
TCCTGACCTC TGGGAGTGGG GGGCTCAAGG GTGGGAGGCC ATAGCTTGGG GATGCTGGCA    18360
ATGTGTGGGA TGGGCCCAGG GAAGGCCTCT GGCCTACTAG GGGCTCTGGC CCTGACCCAC    18420
GGCCACTCAC TCCTCAGAGA CGTCTCCCAC AACCTGCTCC GGGCGCTGGA CGTTGGGCTC    18480
CTGGCGAACC TCTCGGCGCT GGCAGAGCTG TGAGTGTCCC CCAGTCGTGC CAGCATGCGG    18540
GGCTCACTCC GGGTGGGCTG GCGGCACCGC CTCTTGCTGC TCAGCTGTGG GGGCTTCCAT    18600
CAGCTTTGCC GAATCCCCCG TCTCTTCCAG GGATATAAGC AACAACAAGA TTCTACGTT     18660
AGAAGAAGGA ATATTTGCTA ATTTATTTAA TTAAGTGAA ATGTAAGTTG TGGTTCTTTG     18720
GGTGGGGTCC TGGCTGGACC CCAGGCCCCC AATATCCCTT CTGCCCTCCC AGTTGGTCCG    18780
TGTCCCCTTC CAGGCTTGAG ACCAGATCCT GGGGGCAGTT CACTGCCTGC TTGGAGCCCC    18840
CCAGTGCCGG CTTGGTTGGG GCAGGGAGG CGGTGCTGTC AGGGTGGCTC AGGGCCTGG      18900
TTGCCAGTGG GGGGCTGGCA TAGACCCTTC CCACCAGACC TGGTCCCCAA CACCTGCCCC    18960
TGCCCTGCAG AAACCTGAGT GGGAACCCGT TGAGTGTGA CTGTGGCCTG GCGTGGCTGC     19020
CGCGATGGGC GGAGGAGCAG CAGGTGCGGG TGGTGCAGCC CGAGAGCAGC CACGTGTGCT    19080
GGGCCTGGCT CCCTGGCTGG CCAGCCTCTG CTTGGCATCC CCTTGCTGGA CAGTGGCTGT    19140
GGTGAGTGCC TGTGGGTGGG GCCAGCTCTG TCCTTCCCAG CCAGGTGGGA CCTGGGCCCT    19200
GCAGACACTG GCAGGGCTC AGGAAGGCCT CTCTGGGGGG GGCCTCCGGG CCAAGGGAAC     19260
AGCATGGGAG CCTGTGAGTG CGGCGGGCGG ATGTGGGGGC GTGGGGTGGA GCCAGGAGGA    19320
```

-continued

| | | | | | | |
|---|---|---|---|---|---|---|
| GCAGAACCCG | GGGTCCAGTG | GCTGCCTCTT | CTAGGTGAGG | AGTTTGTCGC | CTGCCTCCCT | 19380 |
| GACAACAGCT | CAGGCACCGT | GGCAGCAGTG | TCCTTTTCAG | CTGCCCACGA | AGGCCTGCTT | 19440 |
| CAGCCAGAGG | CCTGCAGCGC | CTTCTGCTTC | TCCACCGGCC | AGGGCCTCGC | AGCCCTCTCG | 19500 |
| GAGCAGGGCT | GGTGCCTGTG | TGGGGCGGCC | CAGCCCTCCA | GTGCCTCCTT | TGCCTGCCTG | 19560 |
| TCCCTCTGCT | CCGGCCCCCC | GCCCCCTCCT | GCCCCACCT | GTAGGGCCC | CACCCTCCTC | 19620 |
| CAGTCACGTC | TTCCCTGCCT | CCCCAGGGGC | CACCCTGGTG | GGGCCCACG | GACCTTCTGC | 19680 |
| CTCTGGCCAG | CTAGCAGCCT | TCCACATCGC | TGCCCCGCTC | CCTGTCACTG | CCACACGCTG | 19740 |
| GGACTTCGGA | AGTAGCTCCG | CCGAGGTGGA | TGCCGCTGGG | CCGGCTGCCT | CGCATCGCTA | 19800 |
| TGTGCTGCCT | GGGCGCTATC | ACGTGACGGC | CGTGCTGCCC | TGGGGGCCGG | CTCAGCCCTG | 19860 |
| CGGGGGAAAA | AATTTCAGGG | GAAGGGCACC | CGCCGTCCCT | GGGAGCTCGT | GTGCCCGTCC | 19920 |
| TCGGTGCAGA | GTGACGAGAG | CCTCGACCTC | AGCATCCAGA | ACCGCGGTGG | TTCAGGCCTG | 19980 |
| GAGGCCGCCT | ACAGCATCGT | GGCCCTGGGC | GAGGAGCCGG | CCCGAGGTGA | GTGTCTGCTG | 20040 |
| CCCACTCCCC | TTCCTCCCCA | GGGCCATCCA | GATGGGGCAG | AGCCTGGTAC | CCCCGTCTTG | 20100 |
| GGCCCACACT | GACCGTTGAC | ACCCTCGTTC | CCACCGGTCT | CCAGCGGTGC | ACCCGCTCTG | 20160 |
| CCCCTCGGAC | ACGGAGATCT | TCCCTGGCAA | CGGGCACTGC | TACCGCCTGG | TGGTGGAGAA | 20220 |
| GGCGGCCTGG | CTGCAGGCGC | AGGAGCAGTG | TCAGGCCTGG | GCCGGGCCG | CCCTGGCAAT | 20280 |
| GGTGGAACAG | TCCCGCCGTG | CAGCGCTTCC | CTGGTCTCCC | GGGTCACCAG | GTGCCTGCCC | 20340 |
| CCACCCCCCG | AGGGGCCATA | GGTTGGGAGA | TCTCTGAAGC | ACTGGGGCAC | AGACTGCGGC | 20400 |
| TGGGGAGTCT | CAGGAGGAAG | GAGGTGGGAG | CTGGGCCGGC | CCTGGTGAGC | AGGTGGCGCC | 20460 |
| GGCCGGTGGG | GCCGTTCCTG | TCAGCTCTGC | AGATGCAGAG | GTGGACATGA | GCTGGGGCA | 20520 |
| GCCTCCGGAC | ACTCCTGGGC | ACGCCATACG | GGAGGTGGCC | TGCACGGGGA | TCCCTGCCGG | 20580 |
| TACCCACAGG | CCCCGTGGGT | GGGTGCTGCT | GTGAGCCTGG | GCTGGTGGGC | CCTGGTCTCC | 20640 |
| GGGCTCTGAG | CCTCAGTTTC | CCCATCTGGA | AAGGGGACA | GTGATGGGGC | TCCCAGCGGG | 20700 |
| CTGCTGTGAG | GGTGGGAGGA | TGGAGGAGTG | CCCTGAGCCC | CCTGCCATCC | CACACCCGCC | 20760 |
| CCCAGGAGCC | TAGACGTGTG | GATCGGCTTC | TCGACTGTGC | AGGGGGTGGA | GGTGGGCCCA | 20820 |
| GCGCCGCAGG | GCGAGGCCTT | CAGCCTGGAG | AGCTGCCAGA | ACTGGCTGCC | CGGGGAGCCA | 20880 |
| CACCCAGCCA | CAGCCGAGCA | CTGCGTCCGG | CTCGGGCCCA | CCGGGTGGTG | TAACACCGAC | 20940 |
| CTGTGCTCAG | CGCCGCACAG | CTACGTCTGC | GAGCTGCAGC | CCGGAGGTGT | GCGGGGGGCC | 21000 |
| AGGCAGGGC | CTGAGACGCT | GGCTGTGGTT | AGGGGCCTGC | CGAGCGCCCG | CGGTGGAGCC | 21060 |
| TGGGCTGAGG | AGGAGGGGCT | GGTGGGGGGG | TTTTCGGGCG | GCTCGGCTCC | CCAGTCTGTT | 21120 |
| CGTCCTGGTG | TCCTGGGCCC | TGGCCCGGCG | CCTCACTGTG | CACTCGCCAC | CCCAGGCCA | 21180 |
| GTGCAGGATG | CCGAGAACCT | CCTCGTGGGA | GCGCCAGTG | GGGACCTGCA | GGGACCCCTG | 21240 |
| ACGCTCTCTG | GCACAGCAGG | ACGGCCTCTC | AGCCCCGCAC | GAGCCCGTGG | AGGTAGTCGG | 21300 |
| CCCCCCACGT | TCTACAACCT | GCCCTCCTGC | CTGCCCCTGG | AGGCCTTGCC | TGCCCTGCCC | 21360 |
| ACTGTGGGTC | TCGCCAAAAA | ACTTGGGGGC | CTTAATGTTG | CTTGTGCCCA | GTGAAGATGG | 21420 |
| TTGGGAAAAT | CCAGAGTGCA | GAGAGGAAAG | CGTTTACTCA | CATTACCTCC | AGGCCTTTTC | 21480 |
| TCTGAGCGTG | TGTGAGTTAT | TCCTGAAAGG | CAGGTCAGGG | GTCCTGCCCC | CCATGGACAG | 21540 |
| TTTCCACCGG | AGTCTTCCTC | TCGAGCGACA | GGAGCCAGGC | CTGTGGGGT | CTGATGGCTC | 21600 |
| GCTCTCCTTC | CCTCCCCTCT | TCCTGGGAAG | TTCGGGTAGG | GGAGTCTGG | GCTTCAGGCT | 21660 |
| GGGATGGGGT | CTGTGGAGCT | GAGGCGGCCC | CCTGCCCACC | AGGTCATGGT | ATTCCCGGGC | 21720 |

```
CTGCGTCTGA GCCGTGAAGC CTTCCTCACC ACGGCCGAAT TTGGGACCCA GGAGCTCCGG    21780
CGGCCCGCCC AGCTGCGGCT GCAGGTGTAC CGGCTCCTCA GCACAGCAGG TGGGACTCTG    21840
GGTGGTGGGT GGTGGGTGGT GGGCGCCGCA GGACTCGGGG TGGCCTCTCT GAGCTTTCAC    21900
GTCTGCTGGT CCTGTGGCCA CCAGAGTGGT TCCCAGTCTT AGGTGGACAG AGCAGGGGTT    21960
CCAGAGACAC CAGCTCATTC CAGGTGTCCT GGGGGTGGAT GGGTGGGGC CTGCCTGGGG     22020
GCCGGCCTGG GTCAGTCGGC TGGCCGGAGA CGGACGCAGC ACTGGGCTGG GAGTGCTGCC    22080
CAGGTGGGGA GACCTGTCCT CACAGCAAGG CCAGGATTGC TGGTGCAGGC AGTTGGGCAT    22140
CTCTGACGGT GGCCTGTGGG CAAATCAGGG CCCCAACACC CTCCCCTCCT CACAGGGACC    22200
CCGGAGAACG GCAGCGAGCC TGAGAGCAGG TCCCCGGACA ACAGGACCCA GCTGGCCCCC    22260
GCGTGCATGC CAGGGGGACG CTGGTGCCCT GGAGCCAACA TCTGCTTGCC GCTGGACGCC    22320
TCCTGCCACC CCCAGGCCTG CGCCAATGGC TGCACGTCAG GGCCAGGGCT ACCCGGGGCC    22380
CCCTATGCGC TATGGAGAGA GTTCCTCTTC TCCGTTCCCG CGGGGCCCCC CGCGCAGTAC    22440
TCGGTGTGTG GCCCTGACCT GGGTCTGTTC CCTGCATCTC CTCAGGCCAC CTTCCTGTCT    22500
GCTGCCCAGG GTCTGGGTCT GTGCACCAGA CACACCCAGC CTGCAGGCCC CTCCCACGTC    22560
CTTGCCACCT CTGACCTCCG ACCTCTGCAG TGCCCTCGGC CCTCTCCCAG TGGGAGAAGC    22620
TCTCGCCTGG CCCTTGGCAC GAGCTGTGCT CCTCTTCCTC TCTCCAGCA CAGCTGCTCC     22680
TTCCTGTCTG CCAGGTCTTG GCCTGTGTCC TCTCCCCGTG TGTCCCCCGG TCTGCAACTG    22740
TCCTGCCTGT CCTTGTCACG AGCACTGTGG GGAGGCTCCT TGAGGTGTGG CTGACGAAGC    22800
GGGGAGCCCT GCGTCGTCCA CCCTCATCCG TCGTGCGGGG GTCCACGGGC CATGACCGTG    22860
AGGACGTGAT GCAGCCCTGC CTCCCTCTCC ACAGGTCACC CTCCACGGCC AGGATGTCCT    22920
CATGCTCCCT GGTGACCTCG TTGGCTTGCA GCACGACGCT GGCCNTGGCG CCCTCCTGCA    22980
CTGNTCGCCG GNTCCCGGCC ACCCTGGTCC CCGGGCCCCG TACCTCTCCG CCAACGCCTC    23040
GTCATGGCTG CCCCACTTGC NAGCCCAGCT GGAGGGCACT TGGGCCTGCC CTGCCTGTGC    23100
CCTGCGGCTG CTTGCAGCCA CGGAACAGCT CACCGTGCTG CTGGGCTTGA GGCCCAACCC    23160
TGGACTGCGG CTGCCTGGGC GCTATGAGGT CCGGGCAGAG GTGGGCAATG GCGTGTCCAG    23220
GCACAACCTC TCCTGCAGCT TTGACGTGGT CTCCCCAGTG GCTGGGCTGC GGGTCATCTA    23280
CCCTGCCCCC CGCGACGGCC GCCTCTACGT GCCCACCAAC GGCTCAGCCT TGGTGCTCCA    23340
GGTGGACTCT GGTGCCAACG CCACGGCCAC GGCTCGCTGG CCTGGGGGCA GTGTCAGCGC    23400
CCGCTTTGAG AATGTCTGCC CTGCCCTGGT GGCCACCTTC GTGCCCGGCT GCCCCTGGGA    23460
GACCAACGAT ACCCTGTTCT CAGTGGTAGC ACTGCCGTGG CTCAGTGAGG GGGAGCACGT    23520
GGTGGACGTG GTGGTGGAAA ACAGCGCCAG CCGGGCCAAC CTCAGCCTGC GGGTGACGGC    23580
GGAGGAGCCC ATCTGTGGCC TCCGCGCCAC GCCCAGCCCC GAGGCCCGTG TACTGCAGGG    23640
AGTCCTAGTG GTGAGTATGG CCGAGGCTCC ACCACCAGCC CCAGGCAGG TGCCTGCAGA     23700
CAGGGTGCTC ACACAGGGCG TGAGGCCTGG CTTCCCAGTG AGGGCAGCAG CCCAGTTACT    23760
GGGGACGTCG GCCCCGGGCA GGTCCTGCTG GCTGGCTCCT CGGGCTACCT GGTGGGCTTT    23820
AAATTCCTGG AAAGTCACGG CTCTGACAGT GGCTCCGCTA ACTCATTCCA CTGTCTCATT    23880
TCACAAAATG AATTTAAAAC TCTGCTCCCT GACCTCACAC GAGCCCCGT GAGTCTCTCA     23940
CGCCCTCTGC TGTGTTCTCG CCTGGCTAAA GCGAGTGGCT TTGAGGTGG AGTCTGAACC     24000
CCTGATGGGA AACTGCGGGC TGCCCGCGGT GCCACCATGC TGGGTACATG GGGGACAGGG    24060
CTGTCTCCAT CTTGCGGGTA CCTGCCTCTT CACCAGGGGC CTTGGGAGGG GCCATCAGAA    24120
```

```
ATGGCGTGAC CTGTGCAGCC TGTCCTGGGT TCTGTAAGCC AGTGTAGGTG CCTCCCCTCA    24180
CTGCTCCGAG CTCTCTGGGT GAGGAGCTGG GGCAAGAGCG CCGGGAGGGT CTGAGAAGAC    24240
TCAGAGAGAG GTGGACTCTT TGTAGCTGGT ACTAGGTTTG CTTTACAGAT GGGGAAACTG    24300
AGGCACAGAG AGGTTGAGGC ATTAGTAGTA CTACATGGCT GGCTGGAGAG CCGGACAGTG    24360
AGTGTCCCAG CCCGGGCTTG CTCCCATGG  CATGCAGAGC CCCGGGCACC TCCTCTCCTC    24420
TGTGCCCCGC GTGGGACTCT CCAGCCCGAC GGGAGGTGTG TCCAGGAGGC GACAGGCTAA    24480
GGGCAGAGTC CTCCACAGAG CCCAGGCTGA CACCATTCCC CCCGCAGAGG TACAGCCCCG    24540
TGGTGGAGGC CGGCTCGGAC ATGGTCTTCC GGTGGACCAT CAACGACAAG CAGTCCCTGA    24600
CCTTCCAGAA CGTGGTCTTC AATGTCATTT ATCAGAGCGC GGCGGTCTTC AAGCTCTCAG    24660
TAGGTGGGCG GGGGTGGGGA GGGGAGGGGA TGGGGCGGGG CAGGGCGGGG GCGGGCTCCA    24720
CCTTCACCTC TGCCTTCTGC TCTGCTTCAT GCTGCCCGAG GACGCTGCCA TGGCTGTGGG    24780
TGAGTGGAGG GAGGGACGCC AATCAGGGCC AGGCCTCTCA CCTGCCACCT GGGCTCACTG    24840
ACGCCTGTCC CTGCAGCTGA CGGCCTCCAA CCACGTGAGC AACGTCACCG TGAACTACAA    24900
CGTAACCGTG GAGCGGATGA ACAGGATGCA GGGTCTGCAG GTCTCCACAG TGCCGGCCGT    24960
GCTGTCCCCC AATGCCACGC TAGCACTGAC GGCGGGCGTG CTGGTGGACT CGGCCGTGGA    25020
GGTGGCCTTC CTGTGAGTGA CTCGGGGGCC GGTTTGGGGT GGGCACCAGG CTCTTGTCCC    25080
AGCCCCAGCC TCAGCCGAGG GACCCCCACA TCACGGGGTT GCTTTTCTGA GCCTCGGTTT    25140
CCCTGTCTGT TGGGAGGTAA CTGGGTGCAC AGGAGCCCTG AGGCTGCACG GGAGCCGGGA    25200
GAGGCCTCAG CACAGCCGGG TGGGCCCTGA ATGGAGGCCC GGGGCGTGAC TGCAGAGTGG    25260
AGCCTCGGCT GGGTCCAAG  CACCCCCTGC CCGCCACCG  CCCACCCCTG TCCCGGTTCA    25320
CTCACTGCGT CCCACCGCCC CGGGAGGTGG ACCTTTGGGG ATGGGGAGCA GGCCCTCCAC    25380
CAGTTCCAGC CTCCGTACAA CGAGTCTTCC AGTTCAGACC CTCGTGCCAG GTGCTGGTGG    25440
AGCACATGTC ACGCACACCT ACGCTGCCCN NACTGGGTNA GGNAGGGCCN AGNNTGGGG    25500
GNGTGGACAG GAAGGTGGGC CCTGAACTGT GCTTTCCGCC CTCCCCGGGC CTGGCTCTTG    25560
CTGCTCTGCT GCCCCGAGTG CAGCTGCACT TGGAGGCGGT GCCGTCCTCG CCAGGCAGCC    25620
CTCAGTGCTG CTACACCTGT GCTCCGTCCC GCACGTGGCT TGGGAGCCTG GGACCCTTAA    25680
GGCTGGGCCG CAGGTGCAGC CGTTCACCCC GGGCTCCTCA GGCGGGGGGC TTCTGCCGAG    25740
CGGGTGGGGA GCAGGTGGGG GTGCCGCGGC TGCCCCACTC GGGCCTGTCC CCACAGGTGA    25800
GTACCTCCTG ACCGTGCTGG CATCTAATGC CTTCGAGAAC CTGACGCAGC AGGTGCCTGT    25860
GAGCGTGCGC GCCTCCCTGC CCTCCGTGGC TGTGGGTGTG AGTGACGGCG TCCTGGTGGC    25920
CGGCCGGCCC GTCACCTTCT ACCCGCACCC GCTGCCCTCG CCTGGGGGTG TTCTTTACAC    25980
GTGGGACTTC GGGGACGGCT CCCCTGTCCT GACCCAGAGC CAGCCGGCTG CCAACCACAC    26040
CTATGCCTCG AGGGGCACCT ACCACGTGCG CCTGGAGGTC AACAACACGG TGAGCGGTGC    26100
GGCGGCCCAG GCGGATGTGC GCGTCTTTGA GGAGCTCCGC GGACTCAGCG TGGACATGAG    26160
CCTGGCCGTG GAGCAGGGCG CCCCCGTGGT GGTCAGCGCC GCGGTGCAGA CGGGCGACAA    26220
CATCACGTGG ACCTTCGACA TGGGGGACGG CACCGTGCTG TCGGGCCCGG AGGCAACAGT    26280
GGAGCATGTG TACCTGCGGG CACAGAACTG CACAGTGACC GTGGGTGCGG CCAGCCCCGC    26340
CGGCCACCTG GCCCGGAGCC TGCACGTGCT GGTCTTCGTC CTGGAGGTGC TGCGCGTTGA    26400
ACCCGCCGCC TGCATCCCCA CGCAGCCTGA CGCGCGGCTC ACGGCCTACG TCACCGGGAA    26460
CCCGGCCCAC TACCTCTTCG ACTGGACCTT CGGGGATGGC TCCTCCAACA CGACCGTGCG    26520
```

```
GGGGTGCCCG ACGGTGACAC ACAACTTCAC GCGGAGCGGC ACGTTCCCCC TGGCGCTGGT     26580
GCTGTCCAGC CGCGTGAACA GGGCGCATTA CTTCACCAGC ATCTGCGTGG AGCCAGAGGT     26640
GGGCAACGTC ACCCTGCAGC CAGAGAGGCA GTTTGTGCAG CTCGGGGACG AGGCCTGGCT     26700
GGTGGCATGT GCCTGGCCCC CGTTCCCCTA CCGCTACACC TGGGACTTTG GCACCGAGGA     26760
AGCCGCCCCC ACCCGTGCCA GGGCCCTGA GGTGACGTTC ATCTACCGAG ACCCAGGCTC     26820
CTATCTTGTG ACAGTCACCG CGTCCAACAA CATCTCTGCT GCCAATGACT CAGCCCTGGT     26880
GGAGGTGCAG GAGCCCGTGC TGGTCACCAG CATCAAGGTC AATGGCTCCC TTGGGCTGGA     26940
GCTGCAGCAG CCGTACCTGT TCTCTGCTGT GGGCCGTGGG CGCCCCGCCA GCTACCTGTG     27000
GGATCTGGGG GACGGTGGGT GGCTCGAGGG TCCGGAGGTC ACCCACGCTT ACAACAGCAC     27060
AGGTGACTTC ACCGTTAGGT GGCCGGCTGG AATGAGGTGA GCCGCAGCGA GGCCTGGCTC     27120
AATGTGACGG TGAAGCGGCG CGTGCGGGGG CTCGTCGTCA ATGCAAGCCC CACGGTGGTG     27180
CCCCTGAATG GGAGCGTGAG CTTCAGCACG TCGCTGGAGG CCGGCAGTGA TGTGCGCTAT     27240
TCCTGGGTGC TCTGTGACCG CTGCACGCCC ATCCCTGGGG GTCCTACCAT CTCTTACACC     27300
TTCCGCTCCG TGGGCACCTT CAATATCATC GTCACGGCTG AGAACGAGGT GGGCTCCGCC     27360
CAGGACAGCA TCTTCGTCTA TGTCCTGCAG CTCATAGAGG GGCTGCAGGT GGTGGGCGGT     27420
GGCCGCTACT TCCCCACCAA CCACACGGTA CAGCTGCAGG CCGTGGTTAG GGATGGCACC     27480
AACGTCTCCT ACAGCTGGAC TGCCTGGAGG GACAGGGGCC CGGCCCTGGC CGGCAGCGGC     27540
AAAGGCTTCT CGCTCACCGT GCTCGAGGCC GGCACCTACC ATGTGCAGCT GCGGGCCACC     27600
AACATGCTGG GCAGCGCCTG GCCGACTGC ACCATGGACT TCGTGGAGCC TGTGGGGTGG     27660
CTGATGGTGG CCGCCTCCCC GAACCCAGCT GCCGTCAACA CAAGCGTCAC CCTCAGTGCC     27720
GAGCTGGCTG GTGGCAGTGG TGTCGTATAC ACTTGGTCCT TGGAGGAGGG GCTGAGCTGG     27780
GAGACCTCCG AGCCATTTAC CACCCATAGC TTCCCCACAC CCGGCCTGCA CTTGGTCACC     27840
ATGACGGCAG GGAACCCGCT GGGCTCAGCC AACGCCACCG TGGAAGTGGA TGTGCAGGTG     27900
CCTGTGAGTG GCCTCAGCAT CAGGGCCAGC GAGCCCGGAG GCAGCTTCGT GGCGGCCGGG     27960
TCCTCTGTGC CCTTTTGGGG GCAGCTGGCC ACGGGCACCA ATGTGAGCTG GTGCTGGGCT     28020
GTGCCGGCGG CAGCAGCAAG CGTGGCCCTC ATGTCACCAT GGTCTTCCCG GATGCTGGCA     28080
CCTTCTCCAT CCGGCTCAAT GCCTCCAACG CAGTCAGCTG GTCTCAGCC ACGTACAACC     28140
TCACGGCGGA GGAGCCCATC GTGGGCCTGG TGCTGTGGGC CAGCAGCAAG GTGGTGGCGC     28200
CCGGGCAGCT GGTCCATTTT CAGATCCTGC TGGCTGCCGG CTCAGCTGTC ACCTTCCGCC     28260
TGCAGGTCGG CGGGGCCAAC CCCGAGGTGC TCCCCGGGCC CCGTTTCTCC CACAGCTTCC     28320
CCCGCGTCGG AGACCACGTG GTGAGCGTGC GGGGCAAAAA CCACGTGAGC TGGGCCCAGG     28380
CGCAGGTGCG CATCGTGGTG CTGGAGGCCG TGAGTGGGCT GCAGGTGCCC AACTGCTGCG     28440
AGCCTGGCAT CGCCACGGGC ACTGAGAGGA ACTTCACAGC CCGCGTGCAG CGGNCTCTCG     28500
GGTCGCCTAC GCCTGGTACT TCTCGCTGCA GAAGGTCCAG GGCGACTCGC TGGTCATCCT     28560
GTCGGGCCGC GACGTCACCT ACACGCCCGT GGCCGCGGGG CTGTTGGAGA TCCAGGTGCG     28620
CGCCTTCAAC GCCCTGGGCA GTGAGAACCG CACGCTGGTG CTGGAGGTTC AGGACGCCGT     28680
CCAGTATGTG GCCCTGCAGA GCGGCCCCTG CTTCACCAAC CGCTCGGCGC AGTTTGAGGC     28740
CGCCACCAGC CCCAGCCCCC GGCGTGTGGC CTACCACTGG GACTTTGGGG ATGGGTCGCC     28800
AGGGCAGGAC ACAGATGAGC CCAGGGCCGA GCACTCCTAC CTGAGGCCTG GGGACTACCG     28860
CGTGCAGGTG AACGCCTCCA ACCTGGTGAG CTTCTTCGTG GCGCAGGCCA CGGTGACCGT     28920
```

```
CCAGGTGCTG GCCTGCCGGG AGCCGGAGGT GGACGTGGTC CTGCCCCTGC AGGTGCTGAT    28980
GCGGCGATCA CAGCGCAACT ACTTGGAGGC CCACGTTGAC CTGCGCGACT GCGTCACCTA    29040
CCAGACTGAG TACCGCTGGG AGGTGTATCG CACCGCCAGC TGCCAGCGGC CGGGGCGCCC    29100
AGCGCGTGTG GCCCTGCCCG GCGTGGACGT GAGCCGGCCT CGGCTGGTGC TGCCGCGGCT    29160
GGCGCTGCCT GTGGGGCACT ACTGCTTTGT GTTTGTCGTG TCATTTGGGG ACACGCCACT    29220
GACACAGAGC ATCCAGGCCA ATGTGACGGT GGCCCCGAG CGCCTGGTGC CCATCATTGA     29280
GGGTGGCTCA TACCGCGTGT GGTCAGACAC ACGGGACCTG GTGCTGGATG GGAGCGAGTC    29340
CTACGACCCC AACCTGGAGG ACGGCGACCA GACGCCGCTC AGTTTCCACT GGGCCTGTGT    29400
GGCTTCGACA CAGGTCAGTG CGTGGCAGGG CCGTCCTCCA TGCCCCTCAC CCGTCCACAC    29460
CCATGAGCCC AGAGAACACC CAGCTTGCCA CCAGGGCTGG CCCGTCCTCA GTGCCTGGTG    29520
GGCCCCGTCC CAGCATGGGG AGGGGTCTC CCGCGCTGTC TCCTGGGCCG GGCTCTGCTT     29580
TAAAACTGGA TGGGGCTCTC AGGCCACGTC GCCCCTTGTT CTCGGCCTGC AGAGGGAGGC    29640
TGGCGGGTGT GCGCTGAACT TTGGGCCCCG CGGGAGCAGC ACGGTCACCA TTCCACGGGA    29700
GCGGCTGGCG GCTGGCGTGG AGTACACCTT CAGCCTGACC GTGTGGAAGG CCGGCCGCAA    29760
GGAGGAGGCC ACCAACCAGA CGGTGGGTGC CGCCCGCCCC TCGGCCACTT GCCTTGGACA    29820
GCCCAGCCTC CCTGGTCATC TACTGTTTTC CGTGTTTTAG TGCTGGTGGA GGCCGCACGC    29880
TCTCCCCTCT CTGTTTCTGA TGCAAATTCT ATGTAACACG ACAGCCTGCT TCAGCTTTGC    29940
TTCCTTCCAA ACCTGCCACA GTTCCACGTA CAGTCTTCAA GCCACATATG CTCTAGTGGC    30000
AAAAGCTACA CAGTCCCCTA GCAATACCAA CAGTGAGGAA GAGCCCCTTC CCACCCCAGA    30060
GGTAGCCACT GTCCCCAGCC CATGTCCCTG TTGCTGGATG TGGTGGGCCG GTTCTCACCC    30120
TCACGNTCCC TCTCTGGACC GGCCAGGAGG CTTGGTGACC CTGAGCCCGT GGTGGCTGNN    30180
NNNNNNNNNN NNNNAGGGCG GNCTGATTGG GGGTCTTCCC AGAGGGGTCG TCTGAGGGA     30240
GGGTGTGGGA GCAGGTTCCA TCCCAGCTCA GCCTCCTGAC CCAGGCCCTG GCTAAGGGCT    30300
GCAGGAGTCT GTGAGTCAGG CCTACGTGGC AGCTGCGGTC CTCACACCCA CACATACGTC    30360
TCTTCTCACA CGCATCCCCC CAGGGGCCCT CAGTGAGCAT GCCTGCCTC CTGCTAGGGT     30420
CCAGCTGGGT CCAGTACACC AGAACGCACA CTCCAGTGTC CTCTGCCCTG TGTATGCCCT    30480
TCCGCCGTCC AAGTTGGAAG GTGGCAAACC GGATGAGTAT CCTGGGAGGG AGTGAGCTCA    30540
CCGGCAGTGG CCAGGCCCCT GGGAAACCTG GAGTTTGGGA GCAGCATCCT CCATGGGTCC    30600
CCCAGTCCTT CCAGCAGGCC AAATAGACCT GTGTTGGAGG TAACCCCACT CCCACGCCAG    30660
GTGCTGATCC GGNGTGGCGG GNTGCCNATT GNNNNNNNNN NNNTAGGGC GAGTGTGTGT     30720
CCTGCAAGCA CAGGCCGTGT ACGAAGTGAG CCGCAGCTCC TACGTGTACT TGGAGGGCCG    30780
CTGCCTCAAT TGCAGCAGCG GCTCCAAGCG AGGGGTGAGT GTTGAGCGGG GTGTGGGCGG    30840
GCTGGGGATG GGTCCCATGG CCGAGGGGAC GGGGCCTGCA GGCAGAAGTG GGGCTGACAG    30900
GGCAGAGGGT TGCGCCCCCT CACCACCCCT TCTGCCTGCA GCGGTGGGCT GCACGTACGT    30960
TCAGCAACAA GACGCTGGTG CTGGATGAGA CCACCACATC CACGGGCAGT GCAGGCATGC    31020
GACTGGTGCT GCGGCGGGGC GTGCTGCGGG ACGGCGAGGG ATACACCTTC ACGCTCACGG    31080
TGCTGGGCCG CTCTGGCGAG GAGGAAGGCT GCGCCTCCAT CCGCCTGTCC CCCAACCGCC    31140
CGCCGCTGGG GGGCTCTTGC CGCCTCTTCC CACTGGGCGC TGTGCACGCC CTCACCACCA    31200
AGGTGCACTT CGAATGCACG GGTGAGTGCA GGCCTGCGTG GGGGAGCAG CGGGATCCCC     31260
CGACTCTGTG ACGTCACGGA GCCCTCCCGT GATGCCGTGG GGACCGTCCC TCAGGCTGGC    31320
```

| | | | | | |
|---|---|---|---|---|---|
| ATGACGCGGA | GGATGCTGGC | GCCCCGCTGG | TGTACTNCCT | GCTGCTGCGG | CGCTGTCGCC | 31380 |
| AGGGCCACTG | CGAGGAGTTC | TGTGTCTACA | AGGGCAGCCT | CTCCAGCTAC | GGAGCCGTGC | 31440 |
| TGCCCCCGGG | TTTCAGGCCA | CACTTCGAGG | TGGGCCTGGC | CGTGGTGGTG | CAGGACCAGC | 31500 |
| TGGGAGCCGC | TGTGGTCGCC | CTCAACAGGT | GAGCCAGGCC | GTGGGAGGGC | GCCCCGAGA | 31560 |
| CTGCCACCTG | C | | | | | 31571 |

( 2 ) INFORMATION FOR SEQ ID NO:2:

( i ) SEQUENCE CHARACTERISTICS:
        ( A ) LENGTH: 894 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:2:

| | | | | | |
|---|---|---|---|---|---|
| GGTGTGAGGG | GTAGGGGCAG | GGTGGGAGGT | GGGCTCGCGG | GTGGGCTGGG | GTCATGAAGG | 60 |
| GCCTCAGGCG | CTCTGCTATT | GGGTTCCAAG | GCTATCCTGA | GAACAGGGGT | GAGGGGGGAT | 120 |
| TGCCGTGGGG | GGTTAAAGCC | TTGTCATGTT | CGCTTTCGGG | AGATAAAAAC | AACAGGTGGC | 180 |
| CTTTATGGAG | ACGCTGCCCA | GAGCCAGGTC | TGTGCCAGGC | TCCTGTTGGG | GGTCGTCATG | 240 |
| CGGAATCCTG | ACTCTGACCA | TCCGAGGCAT | AGGGACCGTG | GAGATTTGCA | TTTCACAGAT | 300 |
| GAGGAAACAG | GTTTGGAGAG | GTGACACGAC | CTGTCCCAGG | CATCACAGCC | GGGATGTGCA | 360 |
| TAGCAGGGGT | TTGGAACTAT | GAGGTGCCCA | GGACCCAGGG | TTGGATTGAA | AAGGGCGGAG | 420 |
| GGGACTAAGA | TAAGCAGACA | GTTGTCCCCA | GCGCTGGGGA | GAGTCTTGGG | ACCAGTCTGA | 480 |
| TGCCTTGTAT | TTCCCAGGCT | CCAGGCTCCT | CGCCGGGACA | GTGTCTCCTT | GGGTGCGTGC | 540 |
| TGGATCCCTG | GGGGACGTGG | CACATCCCCA | GGCTTGCTAA | ACATTGGGTG | GGTTCTGGCA | 600 |
| TTTGGTTTTG | TAACGTTTCT | GGGTCACTCC | CGCCTGTGGC | CACCCTTCCT | TAGGGGAGCC | 660 |
| GTGTGTCCTT | GGGGCTTTGC | TGGGTGGTCT | CGAGGGTGGG | AGAAGAATGG | GTTCTCCTGG | 720 |
| ACCAATGGAG | CCCGTGCCCC | TCGGGGCCAC | ATTGCTCCTG | CGCTCCCTGA | CTGCGGACGC | 780 |
| GTGTGTCTCG | CGGCTGTCTC | TGTGGAGATG | GCCTCCTCCT | GCCTGGCAAC | AGCACCCACA | 840 |
| GAATTGCATC | AGACCTACCC | CACCCGTTGT | TTGTGATGCT | GTAGCTGAGG | GCTC | 894 |

( 2 ) INFORMATION FOR SEQ ID NO:3:

( i ) SEQUENCE CHARACTERISTICS:
        ( A ) LENGTH: 160 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens
        ( B ) STRAIN: PKD1 HOMOLOGUE 5'

( x i ) SEQUENCE DESCRIPTION: SEQ ID NO:3:

| | | | | | |
|---|---|---|---|---|---|
| GGAAACAGGT | TTGGAGAGGT | GACACGACCT | GTCCCAGGCA | TCACAGCCAG | GACAGGACCT | 60 |
| GTCCAGGCAT | CACAGCCGGG | ATGTGCATAG | CAGGGGTTTG | GAACTATGAG | GTGCCCAGGA | 120 |
| CCCAGGGTTG | GATTGAAAAG | GGCGCAGGGG | ACTAAGATAA | | | 160 |

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PKD1 Forward Primer"

( x i ) SEQUENCE DESCRIPTION: SEQ ID NO:4:

CAGGACCTGT CCCAGGCAT     19

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PKD1 Reverse Primer 1"

( x i ) SEQUENCE DESCRIPTION: SEQ ID NO:5:

CTGGCGGGCG AGGAGAT     17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PKD1 Reverse Primer 2"

( x i ) SEQUENCE DESCRIPTION: SEQ ID NO:6:

CTTTGACAAG CACATCT     17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PKD1 Reverse Primer 3"

( x i ) SEQUENCE DESCRIPTION: SEQ ID NO:7:

CAACTGGCTG GACAACA     17

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PKD1 Blocking
            Oligonucleotide"

( x i ) SEQUENCE DESCRIPTION: SEQ ID NO:8:

AGGACCTGTC CAGGCATC 18